(12) United States Patent
Bacon et al.

(10) Patent No.: US 8,153,667 B2
(45) Date of Patent: Apr. 10, 2012

(54) TRICYCLIC AROMATIC AND BIS-PHENYL SULFINYL DERIVATIVES

(75) Inventors: Edward R. Bacon, Audubon, PA (US); Sankar Chatterjee, Wynnewood, PA (US); Derek Dunn, Coatesville, PA (US); Rabindranath Tripathy, Churchville, PA (US)

(73) Assignee: Cephalon, Inc., Frazer, PA (US)

( * ) Notice: Subject to any disclaimer, the term of this patent is extended or adjusted under 35 U.S.C. 154(b) by 162 days.

(21) Appl. No.: 11/901,150

(22) Filed: Sep. 14, 2007

(65) Prior Publication Data

US 2008/0070956 A1 Mar. 20, 2008

Related U.S. Application Data

(62) Division of application No. 11/103,958, filed on Apr. 12, 2005, now Pat. No. 7,314,875.

(60) Provisional application No. 60/568,952, filed on May 7, 2004.

(30) Foreign Application Priority Data

Apr. 13, 2004 (EP) .................................... 04290981

(51) Int. Cl.
- A61K 31/4196 (2006.01)
- A61K 31/40 (2006.01)
- A61K 31/381 (2006.01)
- A61K 31/34 (2006.01)
- A61K 31/10 (2006.01)
- C07D 249/08 (2006.01)
- C07D 207/00 (2006.01)
- C07D 333/00 (2006.01)
- C07D 307/00 (2006.01)
- C07C 317/00 (2006.01)

(52) U.S. Cl. ...................... 514/360; 548/267.8; 548/541; 549/78; 549/497; 568/27; 514/438; 514/461; 514/424; 514/708

(58) Field of Classification Search .................. 514/360, 514/424, 438, 461, 708; 548/267.8, 541; 549/78, 497; 568/27
See application file for complete search history.

(56) References Cited

U.S. PATENT DOCUMENTS

| | | | |
|---|---|---|---|
| 2,618,637 A | 11/1952 | Archer et al. | |
| 4,066,686 A | 1/1978 | Lafon | |
| 4,127,722 A | 11/1978 | Lafon | |
| 4,177,290 A | 12/1979 | Lafon | |
| 4,744,812 A | 5/1988 | Parg et al. | |
| 4,927,855 A | 5/1990 | Lafon | |
| 4,935,240 A | 6/1990 | Nakai et al. | |
| 4,964,893 A | 10/1990 | Brannigan et al. | |
| 4,980,372 A | 12/1990 | Nakai et al. | |
| 5,162,537 A | 11/1992 | Brannigan et al. | |
| 5,180,745 A | 1/1993 | Lafon | |
| 5,321,000 A | 6/1994 | Brannigan et al. | |
| 5,391,576 A | 2/1995 | Lafon | |
| 5,401,776 A | 3/1995 | Laurent | |
| 5,563,169 A | 10/1996 | Yoshida et al. | |
| 5,612,379 A | 3/1997 | Laurent | |
| 5,719,168 A | 2/1998 | Laurent | |
| 5,827,856 A * | 10/1998 | Andersen et al. | 514/297 |
| 6,346,548 B1 | 2/2002 | Miller et al. | |
| 6,455,588 B1 | 9/2002 | Scammell et al. | |
| 6,472,414 B1 | 10/2002 | Biller et al. | |
| 6,488,164 B2 | 12/2002 | Miller et al. | |
| 6,492,396 B2 | 12/2002 | Bacon et al. | |
| 6,566,404 B2 | 5/2003 | Esteve et al. | |
| 6,670,358 B2 | 12/2003 | Bacon et al. | |
| 6,919,367 B2 | 7/2005 | Bacon et al. | |
| 6,924,314 B2 | 8/2005 | Sharma et al. | |
| 7,041,695 B2 | 5/2006 | Cole | |
| 7,067,538 B2 * | 6/2006 | Bratton et al. | 514/343 |
| 7,119,214 B2 | 10/2006 | Lesur et al. | |
| 7,268,132 B2 | 9/2007 | Bacon et al. | |
| 7,297,817 B2 | 11/2007 | Lesur et al. | |
| 7,423,176 B2 | 9/2008 | Bacon et al. | |
| 7,449,481 B2 | 11/2008 | Bacon et al. | |
| 7,476,690 B2 | 1/2009 | Lesur et al. | |
| 2002/0045629 A1 | 4/2002 | Bacon et al. | |

FOREIGN PATENT DOCUMENTS

| | | |
|---|---|---|
| CA | 1199916 | 1/1986 |
| CA | 1215393 | 12/1986 |
| CA | 1091679 | 12/2008 |
| EP | 528172 | 2/1993 |
| GB | 1 223 548 | 2/1971 |
| GB | 2 271 112 | 6/1994 |
| JP | 04059754 | 3/2008 |
| WO | WO 95/01171 | 1/1995 |

(Continued)

OTHER PUBLICATIONS

Annis et al., Peptides—Frontiers of Peptide Science: Proceedings of the Fifteenth American Peptide Symposium, Kluwer Academic Publishers, The Netherlands, 1999, 343-344.

Bordwell et al., Acidities of benzyl phenyl sulfones and of the corresponding radical cations. Homolytic bond dissociation energies (BDEs) of α-C—H bonds in benzyl phenylsulfones, J. of Physical Organic Chemistry, 1988, vol. 1, 225-239.

Edgar et al., Modafinil Induces Wakefulness Without Intensifying Motor Activity or Subsequent Rebound Hypersomnolence in the Rat, J. of Pharmacology and Experimental Therapeutics, 1997, 283(2), 757-769.

(Continued)

Primary Examiner — Rebecca Anderson
Assistant Examiner — Samantha Shterengarts

(57) ABSTRACT

The present invention provides compounds of the structure:

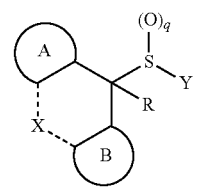

wherein the constituent members are defined herein, including pharmaceutical compositions thereof and methods of treating diseases therewith.

22 Claims, No Drawings

FOREIGN PATENT DOCUMENTS

| | | | | |
|---|---|---|---|---|
| WO | WO 96/26205 | | 8/1996 | |
| WO | WO 97/26240 | | 7/1997 | |
| WO | WO 01/87830 | | 11/2001 | |
| WO | WO 02/10125 | | 2/2002 | |
| WO | WO 03/031420 | * | 4/2003 | 548/206 |
| WO | WO 03/037853 | | 5/2003 | |
| WO | WO 03/066035 | * | 8/2003 | 548/267 |
| WO | WO 2004014847 | * | 2/2004 | 549/200 |

OTHER PUBLICATIONS

El-Sakka et al., Reactions with Thiaxanthen-9-ol: New Thiaxanthene Derivatives with Molluscicidal and Nematocidal Activity, *Arch. Pharm.*, 1994, 327, 133-135.

Han et al., Novel *S*-Xanthenyl Protecting Groups for Cysteine and Their Applications for the $N^\alpha$-9-Fluorenylmethyloxycarbonyl (Fmoc) Strategy of Peptide Synthesis[1-3], *J. Org. Chem.*, 1997, 62, 3841-3848.

Panckeri et al., Modafinil Decreases Hypersomnolence in the English Bulldog, a Natural Animal Model of Sleep-Disordered Breathing, *Sleep*, 1996, 19(8), 626-631.

Shelton et al., Comparative Effects of Modafinil and Amphetamine on Daytime Sleepiness and Cataplexy of Narcoleptic Dogs, *Sleep*, 1995, 18(10), 817-826.

Touret et al., Awakening Properties of Modafinil Without Paradoxical Sleep Rebound: Comparative Study with Amphetamine in the Rat, *Neuroscience Letters*, 1995, 189, 43-46.

Dostert et al., Composes tricycliques portent une chaine alkylaminoalkylthio Synthese et activite pharmacologique, *Eur. J. Med. Chem.*, 1974, 9(3), 259-262.

Saenz et al., New Compounds: Amides Derived from [(10,11-Dihydro-*5H*-dibenzo[a-d]cyclohepten-5-yl)thio]acetic Acid, *J. Pharm. Sci.*, 1972, 61(6), 978-980.

Portevin et al., New Prolyl Endopeptidase Inhibitors: In Vitro and in Vivo Activities of Azabicyclo[2.2.2]octane, Azabicyclo[2.2.1]heptane, and Perhydroindole Derivatives, *J. Med. Chem.*, 1996, 39, 2379-2391.

Klenk et al., The Preparation and Properties of Some Benzohydryl Sulfones, *J. Amer. Chem. Soc.*, 1948, 70, 3846-50.

Schwan et al., 1-Alkenesulfinyl Chlorides: Synthesis, Characterization, and Some Substitution Reactions, *J. Org. Chem.*, 1998, 63(22), 7825-7832.

Carceller et al., Synthesis and Structure-Activity Relationships of 1-Acyl-4-((2-methyl-3-pyridyl)cyanomethyl)piperazines as PAF Antagonists, *J. Med. Chem.*, 1993, 36(20), 2984-97.

Davis et al., New Psychotropic Agents. VII. 5H-Dibenzo[a,d]cycloheptenyl Sulfones, *J. Med. Chem.*, 1966, 9(6), 860-4.

Hiskey et al., Chemistry of Aliphatic Disulfides. XIV. The Preparation of Disulfide Sulfoxides by Selective Oxidation, *J. Org. Chem.*, 1967, 32(10), 3191-4.

Bavin, P.M.G., Aliphatic Chemistry of Fluorene Part IV. Preparation and Alkylation of Some Sulphides and Sulphones, *CA J. Chem.*, 1960, 38, 917-922.

Bavin, P.M.G., Aliphatic Chemistry of Fluorene Part VIII. Benzyl 9-Fluorenyl Sulphoxide and Some 9-Fluorenyl Sulphides, *CA J. Chem.*, 1962, 40, 220-223.

Bartle et al., High-resolution Proton Magnetic Resonance Spectra of Fluorene and its Derviatives. Part III. 9-Substituted Fluorenes, *J. Chem. Soc.*, 1971, (B), 388-396.

Khait et al., The Photochemistry of Sulphoxides. A CIDNP Study of Carbon-Sulphur Bond Cleavage Paths, *J. Chem. Soc. Perk. Trans.*, 1981, 2(11), 1417-1429.

Bordwell et al., Polarizability Effects of Alkyl Groups in $RCH_2$, R, RS, $RSO_2$, RO, and $R_2N$ Moieties in Families of Weak Acids on the Stabilities of Adjacent Anions and Radicals in DMSO Solution, *J. Am. Chem.*, 1994, 116, 973-976.

Ohno et al., Development of Dual-Acting Benzofurans for Thromboxane $A_2$ Receptor Antagonist and Prostacyclin Receptor Agonist: Synthesis, Structure-Activity Relationship, and Evaluation of Benzofuran Derivatives, *J. Org. Chem.*, 2005, 48, 5279-5294.

Venier et al., A New Synthesis of α-Chloro Sulfoxides. The Reaction of Diazo Compounds with Sulfinyl Chlorides, *J. Org. Chem.*, 1973, 38(1), 17-19.

Venier et al., Reaction of Trichloromethyl Anion with 9-Thiofluorenone *S*-Oxide (Fluorenylidenesulfine), *J. Org. Chem.*, 1974, 39(4), 501-504.

Bordwell et al., Stabilization of Carbanions by Polarization of Alkyl Groups on Nonadjacent Atoms, *J. Org. Chem.*, 1982, 47, 2504-2510.

Kice et al., Rates of H/D Exchange of 9-Fluorenyl Sulfoxides: Evidence for an Irreversible E1cB Mechanism for Base-Induced Sulfine Formation from Methyl Diarylmethanesulfinates, *J. Org. Chem.*, 1988, 53, 3593-3597.

* cited by examiner

TRICYCLIC AROMATIC AND BIS-PHENYL SULFINYL DERIVATIVES

REFERENCE TO RELATED APPLICATIONS

The present application is a divisional of U.S. application Ser. No. 11/103,958 filed Apr. 12, 2005, which claims priority to U.S. Provisional Application Ser. No. 60/568,952, filed May 7, 2004 and European Patent Application No. 04290981.2, filed Apr. 13, 2004. The disclosure of each of these applications and patents is hereby incorporated herein by reference in their entireties.

FIELD OF THE INVENTION

The present invention is related to chemical compositions, processes for the preparation thereof and uses of the composition. Particularly, the present invention relates to compositions that include substituted thioacetamides, and their use in the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

BACKGROUND OF THE INVENTION

The compounds disclosed herein are related to the biological and chemical analogs of modafinil. Modafinil, $C_{15}H_{15}NO_2S$, also known as 2-(benzhydrylsulfinyl)acetamide, or 2-[(diphenylmethyl)sulfinyl]acetamide, a synthetic acetamide derivative with wake-promoting activity, has been described in French Patent No. 78 05 510 and in U.S. Pat. No. 4,177,290 ("the '290 patent"). It has been approved by the United States Food and Drug Administration for use in the treatment of excessive daytime sleepiness associated with narcolepsy. Methods for preparing modafinil and several derivatives are described in the '290 patent. The levorotatory isomer of modafinil, along with additional modafinil derivatives are described in U.S. Pat. No. 4,927,855, and are reported to be useful for treatment of hypersomnia, depression, Alzheimer's disease and to have activity towards the symptoms of dementia and loss of memory, especially in the elderly.

Modafinil has also been described as a useful agent in the treatment of Parkinson's disease (U.S. Pat. No. 5,180,745); in the protection of cerebral tissue from ischemia (U.S. Pat. No. 5,391,576); in the treatment of urinary and fecal incontinence (U.S. Pat. No. 5,401,776); and in the treatment of sleep apneas and disorders of central origin (U.S. Pat. No. 5,612,379). In addition, modafinil may be used in the treatment of eating disorders, and to promote weight gain or stimulate appetite in humans or animals (U.S. Pat. No. 6,455,588), and in the treatment of attention deficit hyperactivity disorder (U.S. Pat. No. 6,346,548), and fatigue, especially fatigue associated with multiple sclerosis (U.S. Pat. No. 6,488,164). U.S. Pat. No. 4,066,686 describes various benzhydrylsulphinyl derivatives as being useful in therapy for treating disturbances of the central nervous system.

Several published patent applications describe derivative forms of modafinil and the use of modafinil derivatives in the treatment of various disorders. For example, PCT publication WO 99/25329 describes various substituted phenyl analogs of modafinil as being useful for treating drug-induced sleepiness, especially sleepiness associated with administration of morphine to cancer patients. U.S. Pat. No. 5,719,168 and PCT Publication No. 95/01171 describes modafinil derivatives that are useful for modifying feeding behavior. PCT Publication No. 02/10125 describes several modafinil derivatives of modafinil, along with various polymorphic forms of modafinil.

Additional publications describing modafinil derivatives include U.S. Pat. No. 6,492,396, and PCT Publ. No. WO 02/10125.

Terauchi, H, et al. described nicotinamide derivatives useful as ATP-ase inhibitors (Terauchi, H, et al, *J. Med. Chem.*, 1997, 40, 313-321). In particular, several N-alkyl substituted 2-(Benzhydrylsulfinyl) nicotinamides are described.

U.S. Pat. Nos. 4,980,372 and 4,935,240 describe benzoylaminophenoxybutanoic acid derivatives. In particular, sulfide derivatives of modafinil containing a phenyl and substituted phenyl linker between the sulfide and carbonyl, and a substituted aryl in the terminal amide position, are disclosed.

Other modafinil derivatives have been disclosed wherein the terminal phenyl groups are constrained by a linking group. For example, in U.S. Pat. No. 5,563,169, certain xanthenyl and thiaxanthenyl derivatives having a substituted aryl in the terminal amide position are reported.

Other xanthenyl and thiaxanthenyl derivatives are disclosed in Annis, I; Barany, G. *Pept. Proc. Am. Pept. Symp.* $15^{th}$ (Meeting Date 1997) 343-344, 1999 (preparation of a xanthenyl derivative of Ellman's Reagent, useful as a reagent in peptide synthesis); Han, Y.; Barany, G. *J. Org. Chem.*, 1997, 62, 3841-3848 (preparation of S-xanthenyl protected cysteine derivatives, useful as a reagent in peptide synthesis); and El-Sakka, I. A., et al. *Arch. Pharm.* (Weinheim), 1994, 327, 133-135 (thiaxanthenol derivatives of thioglycolic acid).

Thus, there is a need for novel classes of compounds that possess the beneficial properties similar to that of modafinil. It has been discovered that a class of compounds, referred to herein as substituted thioacetamides, are useful as agents for treating or preventing various diseases or disorders disclosed herein.

SUMMARY OF THE INVENTION

The present invention in one aspect is directed to novel compounds which are useful in the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

These compounds have the structure:

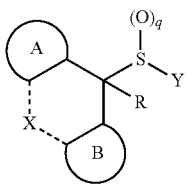

and its stereoisomeric forms, mixtures of stereoisomeric forms, or pharmaceutically acceptable salt forms thereof, wherein the constituent members are defined infra.

In another aspect, the present invention is directed to a pharmaceutical composition which comprises a pharmaceutically acceptable carrier and a therapeutically effective amount of a compound of the present invention.

In yet another aspect, the present invention is directed to methods of preventing or treating the diseases or disorders disclosed herein.

DETAILED DESCRIPTION OF THE INVENTION

In one aspect of the present invention there are provided compounds of formula (A) for the utilities provided herein:

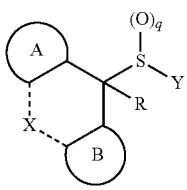

(A)

wherein
rings A and B, together with the carbon atoms to which they are attached, are each independently selected from:
  a) a 6-membered aromatic carbocyclic ring in which from 1 to 3 carbon atoms may be replaced by hetero atoms selected from oxygen, nitrogen and sulfur; and
  b) a 5-membered aromatic carbocyclic ring in which either:
    i) one carbon atom may be replaced with an oxygen, nitrogen, or sulfur atom;
    ii) two carbon atoms may be replaced with a sulfur and a nitrogen atom, an oxygen and a nitrogen atom, or two nitrogen atoms; or
    iii) three carbon atoms may be replaced with three nitrogen atoms, one oxygen and two nitrogen atoms, or one sulfur and two nitrogen atoms;
  wherein said rings are optionally substituted with one to three $R^{20}$ groups;
X is not present, is a bond, O, $S(O)_y$, $NR^{10}$, $C_2$ alkylene, $C_{2-3}$ alkenylene, $C(=O)$, $C(R^{21})_2NR^{10}$, $C(R^{21})=N$, $N=C(R^{21})$, $C(=O)N(R^{10})$, or $NR^{10}C(=O)$; wherein said alkylene and alkenylene groups are optionally substituted with one to three $R^{20}$ groups;
R is H, $C_1$-$C_6$ alkyl, $C_6$-$C_{10}$ aryl, 5-6 membered heteroaryl, $C_3$-$C_7$ cycloalkyl, or 3-7 membered heterocycloalkyl; with the proviso that R cannot be H when $R^1$ is $C(=O)NR^{12}R^{13}$;
Y is $C_1$-$C_9$ alkylene-$R^1$, wherein one or two carbon atoms can be replaced by one or two O, $NR^{10}$, or $S(O)_y$ groups, or a carbon atom can be replaced by a $C_6$-$C_{10}$ arylene, 5-10 membered heteroarylene, $C_3$-$C_6$ cycloalkylene, or 3-6 membered heterocycloalkylene group; $C_2$-$C_6$ alkenylene-$R^1$; or $C_2$-$C_6$ alkynylene-$R^1$; wherein said alkylene, alkenylene, alkynylene, arylene, heteroarylene, cycloalkylene, and heterocycloalkylene groups are optionally substituted with one to three $R^{20}$ groups;
$R^1$ is selected from H, $NR^{12}R^{13}$, $NR^{21}C(=O)R^{14}$, $C(=)R^{15}$, $CO_2R^{11}$, $OC(=O)R^{11}$, $C(=O)NR^{12}R^{13}$, $C(=O)NR^{21}OR^{14}$, $C(=NR^{11})NR^{12}R^{13}$, $NR^{21}S(O)_2R^{11}$, $S(O)_2NR^{12}R^{13}$, $NR^{21}S(O)_2NR^{12}R^{13}$, and $PO(OR^{21})_2$;
$R^{10}$ and $R^{10A}$ at each occurrence are independently selected from H, $C_1$-$C_6$ alkyl, $C_6$-$C_{10}$ aryl, $C(=O)R^{15}$, and $S(O)_y R^{14}$; wherein said alkyl and aryl groups are optionally substituted with one to three $R^{20}$ groups;
$R^{11}$ at each occurrence is independently selected from H, and $C_1$-$C_6$ alkyl; wherein said alkyl is optionally substituted with one to three $R^{20}$ groups;
$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocycloalkyl ring;
  wherein said alkyl and aryl groups and heterocycloalkyl ring are optionally substituted with one to three R20 groups;
$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;
$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;
$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $=O$, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_y R^{22}$;
$R^{21}$ at each occurrence is independently selected from H and $C_1$-$C_6$ alkyl;
$R^{22}$ at each occurrence is independently selected from $C_1$-$C_6$ alkyl, and $C_6$-$C_{10}$ aryl;
$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocycloalkyl ring;
$R^{25}$ at each occurrence is independently the residue of an amino acid after the hydroxyl group of the carboxyl group is removed;
q is 0, 1, or 2;
y is 0, 1, or 2;
with the proviso that when R=H and Y is ($C_1$-$C_6$ alkylene)-$C(=O)NR^{12}R^{13}$, then the alkylene group must be substituted with a spirocycloalkyl group;
with the additional proviso that when Y is ($C_1$-$C_4$ alkylene)$_m$-Z—($C_1$-$C_4$ alkylene)$_n$-$C(=O)NR^{12}R^{13}$, then R must be $C_1$-$C_6$ alkyl;
and the stereoisomeric forms, mixtures of stereoisomeric forms or pharmaceutically acceptable salts forms thereof.

In an additional aspect of the present invention there are provided compounds of formula (I):

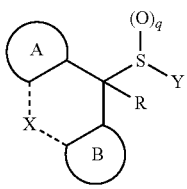

(I)

wherein
rings A and B, together with the carbon atoms to which they are attached, are each independently selected from:
  a) a 6-membered aromatic carbocyclic ring in which from 1 to 3 carbon atoms may be replaced by hetero atoms selected from oxygen, nitrogen and sulfur; and
  b) a 5-membered aromatic carbocyclic ring in which either:
    i) one carbon atom may be replaced with an oxygen, nitrogen, or sulfur atom;
    ii) two carbon atoms may be replaced with a sulfur and a nitrogen atom, an oxygen and a nitrogen atom, or two nitrogen atoms; or
    iii) three carbon atoms may be replaced with three nitrogen atoms, one oxygen and two nitrogen atoms, or one sulfur and two nitrogen atoms;
  wherein said rings are optionally substituted with one to three $R^{20}$ groups;
X is not present, is a bond, O, S(O)$_y$, NR$^{10}$, C$_2$ alkylene, C$_{2-3}$ alkenylene, C(=O), C(R$^{21}$)$_2$NR$^{10}$, C(R$^{21}$)=N, N=C(R$^{21}$), C(=O)N(R$^{10}$), or NR$^{10}$C(=O); wherein said alkylene and alkenylene groups are optionally substituted with one to three $R^{20}$ groups;
R is H or C$_1$-C$_6$ alkyl;
Y is selected from:
  a) C$_1$-C$_6$alkylene-R$^1$;
  b) C$_1$-C$_6$ alkylene-R$^2$;
  c) (C$_1$-C$_4$ alkylene)$_m$-Z—(C$_1$-C$_4$ alkylene)$_n$-R$^1$;
  d) C$_1$-C$_6$ alkylene-O(CH$_2$)$_p$OR$^{21}$,
  e) C$_1$-C$_6$ alkyl substituted with one or two OR$^{21}$ groups; provided that Y cannot be (CH$_2$)$_{1-4}$OR$^{21}$; and
  f) CH$_2$CR$^{21}$=C(R$^{21}$)$_2$ except when X is a bond and q is 2;
  wherein said alkyl and alkylene groups are optionally substituted with one to three $R^{20}$ groups;
Z is O, NR$^{10A}$, S(O)$_y$, CR$^{21}$=CR$^{21}$, C=C(R$^{21}$)$_2$, C≡C, C$_6$-C$_{10}$ arylene, 5-10 membered heteroarylene, C$_3$-C$_6$ cycloalkylene, or 3-6 membered heterocycloalkylene; wherein said arylene, heteroarylene, cycloalkylene, and heterocycloalkylene groups are optionally substituted with one to three $R^{20}$ groups;
R$^1$ is selected from NR$^{12}$R$^{13}$, NR$^{21}$C(=O)R$^{14}$, C(=O)R$^{15}$, CO$_2$R$^{11}$, OC(=O)R$^{11}$, C(=O)NR$^{12}$R$^{13}$, C(=O)NR$^{21}$OR$^{14}$, C(=NR$^{11}$)NR$^{12}$R$^{13}$, NR$^{21}$S(O)$_2$R$^{11}$, S(O)$_2$NR$^{12}$R$^{13}$, NR$^{21}$S(O)$_2$NR$^{12}$R$^{13}$, and PO(OR$^{21}$)$_2$;
R$^2$ is a 5-6 membered heteroaryl, wherein said heteroaryl group is optionally substituted with one to three $R^{20}$ groups;
R$^{10}$ and R$^{10A}$ at each occurrence are independently selected from H, C$_1$-C$_6$ alkyl, C$_6$-C$_{10}$ aryl, C(=O)R$^{15}$, and S(O)$_y$R$^{14}$; wherein said alkyl and aryl groups are optionally substituted with one to three $R^{20}$ groups;
R$^{11}$ at each occurrence is independently selected from H and C$_1$-C$_6$ alkyl; wherein said alkyl is optionally substituted with one to three $R^{20}$ groups;
R$^{12}$ and R$^{13}$ at each occurrence are each independently selected from H, C$_1$-C$_6$ alkyl, and C$_6$-C$_{10}$ aryl, or R$^{12}$ and R$^{13}$, together with the nitrogen to which they are attached, form a 3-7 membered heterocycloalkyl ring;
  wherein said alkyl and aryl groups and heterocycloalkyl ring are optionally substituted with one to three $R^{20}$ groups;
R$^{14}$ at each occurrence is independently selected from C$_1$-C$_6$ alkyl, C$_6$-C$_{10}$ aryl, and arylalkyl; wherein said alkyl, aryl and arylalkyl groups are optionally substituted with one to three $R^{20}$ groups;
R$^{15}$ at each occurrence is independently selected from C$_1$-C$_6$ alkyl, C$_6$-C$_{10}$ aryl, arylalkyl, and heteroaryl; wherein said alkyl, aryl, arylalkyl, and heteroaryl groups are optionally substituted with one to three $R^{20}$ groups;
R$^{20}$ at each occurrence is independently selected from F, Cl, Br, I, OR$^{21}$, OR$^{21}$, NR$^{23}$R$^{24}$, NHOH, NO$_2$, CN, CF$_3$, C$_1$-C$_6$ alkyl, C$_3$-C$_6$ spirocycloalkyl, C$_2$-C$_6$ alkenyl, C$_2$-C$_6$ alkynyl, C$_3$-C$_7$ cycloalkyl, 3-7 membered heterocycloalkyl, phenyl, 5 or 6 membered heteroaryl, arylalkyl, =O, C(=O)R$^{22}$, CO$_2$R$^{21}$, OC(=O)R$^{22}$, C(=O)NR$^{23}$R$^{24}$, NR$^{21}$C(=O)R$^{22}$, NR$^{21}$CO$_2$R$^{22}$, OC(=O)NR$^{23}$R$^{24}$, NR$^{21}$C(=O)R$^{22}$, NR$^{21}$C(=S)R$^{22}$, and S(O)$_y$R$^{22}$;
R$^{21}$ at each occurrence is independently selected from H and C$_1$-C$_6$ alkyl;
R$^{22}$ at each occurrence is independently selected from C$_1$-C$_6$ alkyl and C$_6$-C$_{10}$ aryl;
R$^{23}$ and R$^{24}$ at each occurrence are each independently selected from H, C$_1$-C$_6$ alkyl, and C$_6$-C$_{10}$ aryl, or R$^{23}$ and R$^{24}$, together with the nitrogen to which they are attached, form a 3-7 membered heterocycloalkyl ring;
R$^{25}$ at each occurrence is independently the residue of an amino acid after the hydroxyl group of the carboxyl group is removed;
m is 0 or 1;
n is 0 or 1;
p is 1, 2, 3, or 4;
q is 0, 1, or 2;
y is 0, 1, or 2;
with the following provisos:
  1) when Y is (C$_1$-C$_4$ alkylene)$_m$-Z—(C$_1$-C$_4$ alkylene)$_n$-C(=O)NR$^{12}$R$^{13}$, then R must be C$_1$-C$_6$ alkyl;
  2) Y cannot be

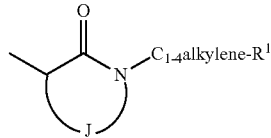

wherein J is C$_2$-C$_4$ alkylene or C$_1$-C$_3$ alkylene-CO—;
  3) when R=H, Y is (C$_1$-C$_6$ alkylene)-R$^1$, and R$^1$ is CO$_2$R$^{11}$, C(=O)NR$^{12}$R$^{13}$, or C(=NR$^{11}$)NR$^{12}$R$^{13}$, then the C$_1$-C$_6$ alkylene group must be substituted with a spirocycloalkyl group;
  4) when X is not present, then Y cannot be C$_1$-C$_6$ alkyl-NR$^{12}$R$^{13}$, or —CH=CHCO$_2$R$^{11}$;
  5) when X is a bond and Y is C$_1$-C$_6$ alkylene-NR$^{12}$R$^{13}$, then R$^{12}$ and R$^{13}$ are each independently selected from H, C$_1$-C$_6$ alkyl, and C$_6$-C$_{10}$ aryl;
and the stereoisomeric forms, mixtures of stereoisomeric forms or pharmaceutically acceptable salts forms thereof.

Other embodiments of compounds of formula (I), when X is not present, or is a bond, then Y cannot be C$_1$-C$_6$ alkylene-NR$^{12}$R$^{13}$. In another aspect, when X is not present, then R$^1$ cannot be NR$^{12}$R$^{13}$. In an additional aspect, R$^1$ does not include $C(=O)NR^{21}OR^{14}$. In a further aspect, when X is not present, R is H and Y is $C_1$-$C_6$ alkylene-$C(=O)NR^{12}R^{13}$, then $R^{12}$ and $R^{13}$ do not include alkyl substituted with $OR^{21}$ or $NR^{23}R^{24}$; and in other aspects $R^{12}$ and $R^{13}$ do not include substituted alkyl.

In yet another embodiment of the present invention there are provided compounds of formula (II):

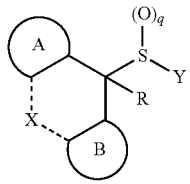

(II)

wherein rings A and B, together with the carbon atoms to which they are attached, are each independently selected from phenylene, pyridylene, thienylene, or a 5-membered aromatic ring in which one or two carbon atoms may be replaced with a nitrogen atom;
   wherein said rings are optionally substituted with one to three $R^{20}$ groups;

X is not present, is a bond, O, $S(O)_y$, $NR^{10}$, $C_2$ alkylene, or $C_2$ alkenylene, wherein said alkylene and alkenylene groups are optionally substituted with one to three $R^{20}$ groups;

R is H or $C_1$-$C_6$ alkyl;

Y is selected from:
  a) $C_1$-$C_6$ alkylene-$R^1$;
  b) $C_1$-$C_6$ alkylene-$R^2$;
  c) $(C_1$-$C_4$ alkylene$)_m$-$Z^1$—$(C_1$-$C_4$ alkylene$)_n$-$R^1$, or $C_1$-$C_4$ alkylene-$Z^2$—$C_1$-$C_4$ alkylene-$R^1$;
  d) $C_1$-$C_6$ alkylene-$O(CH_2)_pOR^{21}$,
  e) $C_1$-$C_6$ alkyl substituted with one or two $OR^{21}$ groups; provided that Y cannot be $(CH_2)_{1-4}OR^{21}$;
  f) $CH_2CR^{21}=C(R^{21})_2CH_2CR^{21}=C(R^{21})_2$ except when X is a bond and q is 2;
   wherein said alkyl and alkylene groups are optionally substituted with one to three $R^{20}$ groups;

$Z^1$ is $CR^{21}=CR^{21}$, $C=C(R^{21})_2$, $C\equiv C$, phenylene, 5-6 membered heteroarylene, $C_3$-$C_6$ cycloalkylene, or 5-6 membered heterocycloalkylene; wherein said phenylene, heteroarylene, cycloalkylene, and heterocycloalkylene groups are optionally substituted with one to three $R^{20}$ groups;

$Z^2$ is O, $NR^{10A}$, $S(O)_y$;

$R^1$ is selected from $NR^{12}R^{13}$, $NR^{21}C(=O)R^{14}$, $C(=O)R^{15}$, $CO_2R^{11}$, $OC(=O)R^{11}$, $C(=O)NR^{12}R^{13}$, $C(=O)NR^{21}OR^{14}$, $C(=NR^{11})NR^{12}R^{13}$, $NR^{21}S(O)_2R^{11}$, $S(O)_2NR^{12}R^{13}$, $NR^{21}S(O)_2NR^{12}R^{13}$, and $PO(OR^{21})_2$;

$R^2$ is a 5-6 membered heteroaryl, wherein said heteroaryl group is optionally substituted with one to three $R^{20}$ groups;

$R^{10}$ and $R^{10A}$ at each occurrence are independently selected from H, $C_1$-$C_6$ alkyl, $C_6$-$C_{10}$ aryl, $C(=O)R^{15}$, and $S(O)_yR^{14}$; wherein said alkyl and aryl groups are optionally substituted with one to three $R^{20}$ groups;

$R^{11}$ at each occurrence is independently selected from H, and $C_1$-$C_6$ alkyl; wherein said alkyl is optionally substituted with one to three $R^{20}$ groups;

$R^{12}$ and $R^{13}$ at each occurrence are independently selected from H, $C_1$-$C_6$ alkyl, and $C_6$-$C_{10}$ aryl, or $R^{12}$ and $R^{13}$, together with the nitrogen to which they are attached, form a 3-7 membered heterocycloalkyl ring;

wherein said alkyl and aryl groups and heterocycloalkyl ring are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;

$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocycloalkyl ring;

$R^{25}$ at each occurrence is independently the residue of an amino acid after the hydroxyl group of the carboxyl group is removed;

m is 0 or 1;
n is 0 or 1;
p is 1, 2, 3, or 4;
q is 0, 1, or 2;
y is 0, 1, or 2;
with the following provisos:
1) when Y is $(C_1$-$C_4$ alkylene$)_m$-$Z^1$—$(C_1$-$C_4$ alkylene$)_n$-$C(=O)NR^{12}R^{13}$ or $C_1$-$C_4$alkylene-$Z^2$—$C_1$-$C_4$alkylene-$C(=O)NR^{12}R^{13}$, then R must be $C_1$-$C_6$ alkyl;
2) Y cannot be

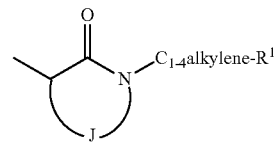

wherein J is $C_2$-$C_4$ alkylene or $C_1$-$C_3$ alkylene-CO—;
3) when R=H, Y is $(C_1$-$C_6$ alkylene)-$R^1$, and $R^1$ is $CO_2R^{11}$, $C(=O)NR^{12}R^{13}$, or $C(=NR^{11})NR^{12}R^{13}$, then the $C_1$-$C_6$ alkylene group must be substituted with a spirocycloalkyl group;
4) when X is not present, then Y cannot be $C_1$-$C_6$ alkyl-$NR^{12}R^{13}$, or —$CH=CHCO_2R^{11}$;
5) when X is a bond and Y is $C_1$-$C_6$ alkylene-$NR^{12}R^{13}$, then $R^{12}$ and $R^{13}$ are each independently selected from H, $C_1$-$C_6$ alkyl, and $C_6$-$C_{10}$aryl;

and the stereoisomeric forms, mixtures of stereoisomeric forms or pharmaceutically acceptable salts forms thereof.

Other embodiments of compounds of formula (II), when X is not present, or is a bond, then Y cannot be $C_1$-$C_6$ alkylene-$NR^{12}R^{13}$. In another aspect, when X is not present, then $R^1$ cannot be $NR^{12}R^{13}$. In an additional aspect, $R^1$ does not include $C(=O)NR^{21}OR^{14}$. In a further aspect, when X is not present, R is H and Y is $C_1$-$C_6$ alkylene-C(=O)$NR^{12}R^{13}$, then $R^{12}$ and $R^{13}$ do not include alkyl substituted with $OR^{21}$ or $NR^{23}R^{24}$; and in other aspects $R^{12}$ and $R^{13}$ do not include substituted alkyl.

In yet another embodiment of the present invention there are provided compounds of formula (III):

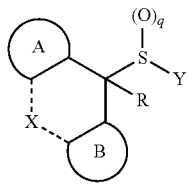

(III)

wherein rings A and B, together with the carbon atoms to which they are attached, are each independently selected from phenylene, pyridylene, furylene, thienylene, or a 5-membered aromatic ring in which 1-3 carbon atoms may be replaced with a nitrogen atom;
  wherein said rings are optionally substituted with one to three $R^{20}$ groups;

X is not present, is a bond, O, $S(O)_y$, or $NR^{10}$, wherein said alkylene and alkenylene groups are optionally substituted with one to three $R^{20}$ groups;

R is H or $C_1$-$C_4$ alkyl;

Y is selected from:
  a) $C_1$-$C_6$ alkylene-$R^1$;
  b) $C_1$-$C_6$ alkylene-$R^2$;
  c) $(C_1$-$C_4$alkylene$)_m$-$Z^1$—$(C_1$-$C_4$alkylene$)_n$-$R^1$, or $C_1$-$C_4$ alkylene-$Z^2$—$C_1$-$C_4$ alkylene-$R^1$;
  d) $C_1$-$C_6$ alkylene-O$(CH_2)_p OR^{21}$,
  e) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, and
  f) $CH_2CR^{21}=C(R^{21})_2$, or $CH_2CR^{21}=C(R^{21})_2$ except when X is a bond and q is 2;
    wherein said alkyl and alkylene groups are optionally substituted with one to three $R^{20}$ groups;

$Z^1$ is $CR^{21}=CR^{21}$, $C=C(R^{21})_2$, $C\equiv C$, or phenylene; wherein said phenylene group is optionally substituted with one to three $R^{20}$ groups;

$Z^2$ is O, $NR^{10A}$, or $S(O)_y$;

$R^1$ is selected from $NR^{12}R^{13}$, $NR^{21}C(=O)R^{14}$, $C(=O)R^{15}$, $CO_2R^{11}$, $C(=O)NR^{12}R^{13}$, $C(=O)NR^{21}OR^{14}$, $NR^{21}S(O)_2R^{11}$, $S(O)_2NR^{12}R^{13}$, and $PO(OR^{21})_2$;

$R^2$ is pyridyl, furyl, thienyl, or a 5-membered heteroaryl group containing 1-3 nitrogen atoms; wherein said heteroaryl group is optionally substituted with one to three $R^{20}$ groups;

$R^{10}$ and $R^{10A}$ at each occurrence are independently selected from H, $C_1$-$C_6$ alkyl, $C_6$-$C_{10}$ aryl, $C(=O)R^{15}$, and $S(O)_y R^{14}$; wherein said alkyl and aryl groups are optionally substituted with one to three $R^{20}$ groups;

$R^{11}$ at each occurrence is independently selected from H, and $C_1$-$C_6$ alkyl; wherein said alkyl is optionally substituted with one to three $R^{20}$ groups;

$R^{12}$ and $R^{13}$ at each occurrence are each independently selected from H and $C_1$-$C_6$ alkyl, or $R^{12}$ and $R^{13}$, together with the nitrogen to which they are attached, form a 5-6 membered heterocycloalkyl;
  wherein said alkyl and heterocycloalkyl groups are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{15}$ at each occurrence is independently selected from $C_1$-$C_6$ alkyl, $C_6$-$C_{10}$ aryl, arylalkyl, and heteroaryl; wherein said alkyl, aryl, arylalkyl, and heteroaryl groups are optionally substituted with one to three $R^{20}$ groups;

$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_y R^{22}$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

m is 0 or 1;

n is 0 or 1;

p is 1, 2, 3, or 4;

q is 0, 1, or 2;

y is 0, 1, or 2;

with the following provisos:
  1) when Y is $(C_1$-$C_4$ alkylene$)_m$-$Z^1$—$(C_1$-$C_4$ alkylene$)_n$-C(=O)$NR^{12}R^{13}$ or $C_1$-$C_4$ alkylene-$Z^2$—$C_1$-$C_4$ alkylene-C(=O)$NR^{12}R^{13}$, then R must be $C_1$-$C_6$ alkyl;
  2) when R=H, Y is $(C_1$-$C_6$ alkylene)-$R^1$, and $R^1$ is $CO_2R^{11}$ or C(=O)$NR^{12}R^{13}$, then the $C_1$-$C_6$ alkylene group must be substituted with a spirocycloalkyl group;
  3) when X is not present, then Y cannot be $C_1$-$C_6$ alkyl-$NR^{12}R^{13}$, or —CH=CHCO$_2R^{11}$;
  4) when X is a bond and Y is $C_1$-$C_6$ alkylene-$NR^{12}R^{13}$, then $R^{12}$ and $R^{13}$ are each independently selected from H or $C_1$-$C_6$ alkyl;

and the stereoisomeric forms, mixtures of stereoisomeric forms or pharmaceutically acceptable salts forms thereof.

Other embodiments of compounds of formula (III), when X is not present, or is a bond, then Y cannot be $C_1$-$C_6$ alkylene-$NR^{12}R^{13}$. In another aspect, when X is not present, then $R^1$ cannot be $NR^{12}R^{13}$. In an additional aspect, $R^1$ does not include C(=O)$NR^{21}OR^{14}$. In a further aspect, when X is not present, R is H and Y is $C_1$-$C_6$ alkylene-C(=O)$NR^{12}R^{13}$, then $R^{12}$ and $R^{13}$ do not include alkyl substituted with $OR^{21}$ or $NR^{23}R^{24}$; and in other aspects $R^{12}$ and $R^{13}$ do not include substituted alkyl.

In a further embodiment of the present invention there are provided compounds of formula (IV):

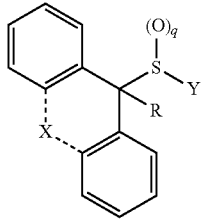

(IV)

wherein
the phenylene rings are each independently optionally substituted with one to three R20 groups;
X is not present or is a bond;
R is H or $C_1$-$C_4$ alkyl;
Y is selected from:
a) $C_1$-$C_6$ alkylene-$R^1$;
b) $C_1$-$C_6$ alkylene-$R^2$;
c) $C_1$-$C_4$ alkylene-O$(CH_2)_p$OR$^{21}$,
d) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, and
e) $CH_2CR^{21}\!=\!C(R^{21})_2CH_2CR^{21}\!=\!C(R^{21})_2$ except when X is a bond and q is 2;
wherein said alkylene groups optionally substituted with an $R^{20}$ group;
$R^1$ is selected from pyrrolidinyl, piperidinyl, morpholinyl, $NR^{21}C(\!=\!O)R^{14}$, $C(\!=\!O)R^{15}$, $CO_2R^{11}$, $C(\!=\!O)NR^{12}R^{13}$, $C(\!=\!O)NR^{21}OR^{14}$, $NR^{21}S(O)_2R^{11}$, $S(O)_2NR^{12A}R^{13A}$, and $PO(OR^{21})_2$;
$R^2$ is furyl, thienyl, a 5-membered heteroaryl group containing 1-2 nitrogen atoms, or triazolyl;
wherein said $R^2$ groups are optionally substituted with an $R^{20}$ group;
$R^{11}$ at each occurrence is independently $C_1$-$C_6$ alkyl;
$R^{12}$ and $R^{13}$ at each occurrence are each independently selected from H and $C_1$-$C_6$ alkyl, or $R^{12}$ and $R^{13}$, together with the nitrogen to which they are attached, form a 5-6 membered heterocycloalkyl;
wherein said alkyl and heterocycloalkyl groups are optionally substituted with an $R^{20}$ group;
$R^{12A}$ and $R^{13A}$ at each occurrence are each independently selected from H and $C_1$-$C_6$ alkyl;
$R^{14}$ at each occurrence is independently $C_1$-$C_6$ alkyl;
$R^{15}$ at each occurrence is independently selected from $C_1$-$C_6$ alkyl, and 5-membered heteroaryl;
$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, $=\!O$, $C(\!=\!O)R^{22}$, $CO_2R^{21}$, $OC(\!=\!O)R^{22}$, $C(\!=\!O)NR^{23}R^{24}$, $NR^{21}C(\!=\!O)R^{22}$, $NR^{21}CO_2R^{22}$, $OC(\!=\!O)NR^{23}R^{24}$, $NR^{21}C(\!=\!O)R^{22}$, $NR^{21}C(\!=\!S)R^{22}$, and $S(O)_yR^{22}$;
$R^{21}$ at each occurrence is independently selected from H and $C_1$-$C_6$ alkyl;
$R^{22}$ at each occurrence is independently selected from $C_1$-$C_6$ alkyl, and phenyl;
$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;
p is 1, 2, 3, or 4;
q is 1 or 2;
y is 0, 1, or 2;
with the following provisos:
1) when R=H, Y is $(C_1$-$C_6$ alkylene)-$R^1$, and $R^1$ is $CO_2R^{11}$ or $C(\!=\!O)NR^{12}R^{13}$, then the $C_1$-$C_6$ alkylene group must be substituted with a spirocycloalkyl group;
2) when X is not present, then Y cannot be $C_1$-$C_6$ alkyl-$NR^{12}R^{13}$, wherein $NR^{12}R^{13}$ is pyrrolidinyl, piperidinyl, or morpholinyl;
and the stereoisomeric forms, mixtures of stereoisomeric forms or pharmaceutically acceptable salts forms thereof.

Other embodiments of compounds of formula (IV), when X is not present, or is a bond, then Y cannot be $C_1$-$C_6$ alkyl-$NR^{12}R^{13}$, wherein $NR^{12}R^{13}$ is pyrrolidinyl, piperidinyl, or morpholinyl. In another aspect, when X is not present, then $R^1$ cannot be pyrrolidinyl, piperidinyl, morpholinyl, or $C(\!=\!O)NR^{21}OR^{14}$. In a further aspect, when X is not present, R is H and Y is $C_1$-$C_6$ alkylene-$C(\!=\!O)NR^{12}R^{13}$, then $R^{12}$ and $R^{13}$ do not include alkyl substituted with $OR^{21}$ or $NR^{23}R^{24}$; and in other aspects $R^{12}$ and $R^{13}$ do not include substituted alyl.

A further aspect of the present invention includes compounds of formula (IV) wherein Y is selected from:
a) $C_1$-$C_4$ alkylene-$R^1$;
b) $C_1$-$C_4$ alkylene-$R^2$;
c) $C_1$-$C_4$ alkylene-O$(CH_2)_p$OR$^{21}$,
d) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$,
e) $CH_2CH\!=\!CH_2$, or $CH_2C(\!=\!C)CH_3$ except when X is a bond and q is 2;
wherein said alkylene groups are optionally substituted with an $R^{20}$ group;
$R^1$ is selected from pyrrolidinyl, piperidinyl, morpholinyl, $NR^{21}C(\!=\!O)R^{14}$, $C(\!=\!O)R^{15}$, $CO_2R^{11}$, $C(\!=\!O)NR^{12}R^{13}$, $C(\!=\!O)NR^{21}OR^{14}$, $NR^{21}S(O)_2R^{11}$, $S(O)_2NR^{12A}R^{13A}$, and $PO(OR^{21})_2$;
$R^2$ is furyl, thienyl, or triazolonyl;
wherein said $R^2$ groups are optionally substituted with an $R^{20}$ group;
$R^{11}$ at each occurrence is independently $C_1$-$C_4$ alkyl;
$R^{12}$ and $R^{13}$ at each occurrence are each independently selected from H and $C_1$-$C_4$ alkyl, optionally substituted with $C(\!=\!O)NR^{12A}R^{13A}$, or $R^{12}$ and $R^{13}$, together with the nitrogen to which they are attached, form a pyrrolidinyl or piperidinyl ring;
$R^{12A}$ and $R^{13A}$ at each occurrence are each independently selected from H and $C_1$-$C_4$ alkyl;
$R^{14}$ at each occurrence is independently $C_1$-$C_4$ alkyl;
$R^{15}$ at each occurrence is independently selected from $C_1$-$C_4$ alkyl, and thienyl;
$R^{20}$ at each occurrence is independently selected from F, Cl, Br, I, $OR^{21}$, $OR^{25}$, $NR^{23}R^{24}$, NHOH, $NO_2$, CN, $CF_3$, $=\!O$, $C(\!=\!O)R^{22}$, $CO_2R^{21}$, $C(\!=\!O)NR^{23}R^{24}$, or $NR^{21}C(\!=\!O)R^{22}$;
$R^{21}$ at each occurrence is independently selected from H and $C_1$-$C_4$ alkyl;
$R^{22}$ at each occurrence is independently $C_1$-$C_4$ alkyl;
$R^{23}$ and $R^{24}$ at each occurrence are each independently selected from H and $C_1$-$C_4$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

p is 1, 2, 3, or 4;

q is 0, 1, or 2.

In a further embodiment of the present invention there are provided compounds of formula (V):

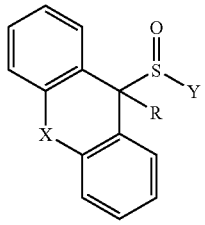

wherein the phenylene rings are each independently optionally substituted with one to three $R^{20}$ groups;

X is a bond, O, $S(O)_y$, $NR^{10}$, $C_2$ alkylene, or $C_2$ alkenylene, wherein said alkylene and alkenylene groups are optionally substituted with an $R^{20}$ group;

R is H or $C_1$-$C_4$ alkyl;

Y is selected from:
a) $C_1$-$C_6$ alkylene-$R^1$;
b) $CH_2CR^{21}$=$C(R^{21})_2CH_2CR^{21}$=$C(R^{21})_2$ except when X is a bond and q is 2;

$R^1$ is selected from pyrrolidinyl, piperidinyl, morpholinyl, $NR^{21}C(=O)R^{14}$, $C(=O)NR^{12}R^{13}$, and $NR^{21}S(O)_2R^{11}$;

$R^{10}$ is independently selected from H, $C_1$-$C_6$ alkyl, $C_6$-$C_{10}$ aryl, $C(=O)R^{14}$, and $S(O)_yR^{14}$; wherein said alkyl and aryl groups are optionally substituted with one to three $R^{20}$ groups;

$R^{11}$ at each occurrence is independently $C_1$-$C_6$ alkyl;

$R^{12}$ and $R^{13}$ at each occurrence are each independently selected from H and $C_1$-$C_6$ alkyl, or $R^{12}$ and $R^{13}$, together with the nitrogen to which they are attached, form a 5-6 membered heterocycloalkyl;

wherein said alkyl and heterocycloalkyl groups are optionally substituted with an $R^{20}$ group;

$R^{14}$ at each occurrence is independently $C_1$-$C_6$ alkyl;

$R^{20}$ at each occurrence is independently selected from F, Cl, Br, I, OR21, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

y is 0, 1, or 2;

with the proviso that when R=H, Y is ($C_1$-$C_6$ alkylene)-$C(=O)NR^{12}R^{13}$, then the $C_1$-$C_6$ alkylene group must be substituted with a spirocycloalkyl group;

and the stereoisomeric forms, mixtures of stereoisomeric forms or pharmaceutically acceptable salts forms thereof.

A further aspect of the present invention includes compounds of formula (V) wherein X is a bond; R is $C_1$-$C_4$ alkyl, Y is $C_1$-$C_6$ alkyl-$C(=O)NR^{12}R^{13}$.

Another aspect includes compounds of formula (V) wherein X is a bond; R is H, Y is $C_1$-$C_6$ alkyl-$R^1$, and $R^1$ is selected from pyrrolidinyl, piperidinyl, morpholinyl, $NR^{21}C(=O)R^{14}$, or $NR^{21}S(O)_2R^{11}$.

A further aspect includes compounds of formula (V) wherein X is a bond and Y is $CH_2CR^{21}$=$C(R^{21})_2$ $CH_2CR^{21}$=$C(R^{21})_2$.

In yet another aspect, there are included compounds of formula (V) wherein Y is $CH_2CH$=$CH_2$, or $CH_2C(=C)CH_3$.

An additional aspect includes compounds of formula (V) wherein the phenylene rings are each independently optionally substituted with one to three $R^{20}$ groups;

q is 1;

X is a bond;

Y is selected from:
a) $C_1$-$C_4$ alkylene-$R^1$;
b) $CH_2CH$=$CH_2$, or $CH_2C(=C)CH_3$ except when X is a bond and q is 2;

$R^1$ is selected from pyrrolidinyl, piperidinyl, morpholinyl, $NR^{21}C(=O)R^{14}$, $C(=O)NR^{12}R^{13}$, and $NR^{21}S(O)_2R^{11}$;

$R^{11}$ at each occurrence is independently $C_1$-$C_4$ alkyl;

$R^{12}$ and $R^{13}$ at each occurrence are each independently selected from H and $C_1$-$C_4$ alkyl, optionally substituted with $C(=O)NR^{12A}R^{13A}$, or $R^{12}$ and $R^{13}$, together with the nitrogen to which they are attached, form a pyrrolidinyl or piperidinyl ring;

$R^{12A}$ and $R^{13A}$ at each occurrence are each independently selected from H and $C_1$-$C_4$ alkyl;

$R^{14}$ at each occurrence is independently $C_1$-$C_4$ alkyl;

$R^{20}$ at each occurrence is independently selected from F, Cl, Br, I, $OR^{21}$, $OR^{25}$, $NR^{23}R^{24}$, NHOH, $NO_2$, CN, $CF_3$, =O, $C(=O)R^{22}$, $CO_2R^{21}$, $C(=O)NR^{23}R^{24}$, or $NR^{21}C(=O)R^{22}$;

$R^{21}$ at each occurrence is independently selected from H and $C_1$-$C_4$ alkyl;

$R^{22}$ at each occurrence is independently $C_1$-$C_4$ alkyl;

$R^{23}$ and $R^{24}$ at each occurrence are each independently selected from H and $C_1$-$C_4$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed.

In yet another embodiment of the present invention there are provided compounds of formula (VI):

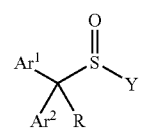

wherein $Ar^1$ and $Ar^2$ are each independently phenyl optionally substituted with one to three $R^{20}$ groups;

R is H or $C_1$-$C_4$ alkyl;

Y is selected from:
  a) $C_1$-$C_6$ alkylene-$R^1$;
  b) $C_1$-$C_6$ alkylene-$R^2$;
  c) $C_1$-$C_6$ alkylene-$O(CH_2)_pOR^{21}$,
  d) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$;

$R^1$ is selected from $C(=O)R^{15}$, $CO_2R^{11}$, $C(=O)NR^{12}R^{13}$, $C(=O)NR^{21}OR^{14}$, $S(O)_2NR^{12A}R^{13A}$, and $PO(OR^{21})_2$;

$R^2$ is furyl, thienyl, or triazolyl; wherein said $R^2$ groups are optionally substituted with an $R^{20}$ group;

$R^{11}$ at each occurrence is independently $C_1$-$C_6$ alkyl;

$R^{12}$ and $R^{13}$ at each occurrence are each independently selected from H and $C_1$-$C_6$ alkyl, or $R^{12}$ and $R^{13}$, together with the nitrogen to which they are attached, form a 5-6 membered heterocycloalkyl;

$R^{12A}$ and $R^{13A}$ at each occurrence are each independently selected from H and $C_1$-$C_6$ alkyl;

$R^{14}$ at each occurrence is independently $C_1$-$C_6$ alkyl;

$R^{15}$ at each occurrence is independently selected from $C_1$-$C_6$ alkyl, and 5-membered heteroaryl;

$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;

$R^{21}$ at each occurrence is independently selected from H and $C_1$-$C_6$ alkyl;

$R^{22}$ at each occurrence is independently selected from $C_1$-$C_6$ alkyl, and phenyl;

$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

p is 1, 2, 3, or 4;
y is 0, 1, or 2;
with the proviso that when R=H, Y is ($C_1$-$C_6$ alkylene)-$R^1$, and $R^1$ is $CO_2R^{11}$ or $C(=O)NR^{12}R^{13}$, then the $C_1$-$C_6$ alkylene group must be substituted with a spirocycloalkyl group;
and the stereoisomeric forms, mixtures of stereoisomeric forms or pharmaceutically acceptable salts forms thereof.

A further aspect of the present invention includes compounds of formula (VI) wherein R is $C_1$-$C_4$ alkyl, and Y is $C_1$-$C_6$ alkyl-$C(=O)NR^{12}R^{13}$. In another aspect, $R^1$ is $C(=O)R^{15}$, $CO_2R^{11}$, $C(=O)NR^{12}R^{13}$, $S(O)_2NR^{12A}R^{13A}$, or $PO(OR^{21})_2$.

Another aspect includes compounds of formula (VI) wherein R is H, and Y is $C_1$-$C_6$ alkyl-$R^1$, wherein said alkyl is substituted with spirocycloalkyl, and $R^1$ is $CO_2R^{11}$, or $C(=O)NR^{12}R^{13}$.

A further aspect includes compounds of formula (VI) wherein $R^1$ is $C(=O)NR^{12}R^{13}$.

In yet another aspect, there are included compounds of formula (VI) wherein $R^1$ is selected from $C(=O)R^{15}$, $C(=O)NR^{21}OR^{14}$, $S(O)_2NR^{21A}R^{13A}$, and $PO(OR^{21})_2$.

An additional aspect includes compounds of formula (VI) wherein Y is $C_1$-$C_6$ alkylene-$O(CH_2)_pOR^{21}$.

In a further aspect, there are compounds of formula (VI) wherein Y is $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$.

In an additional aspect, there are compounds of formula (VI) wherein $Ar^1$ and $Ar^2$ are each independently phenyl optionally substituted with one to three $R^{20}$ groups;

R is H or $C_1$-$C_4$ alkyl;
Y is selected from:
  a) $C_1$-$C_4$ alkylene-$R^1$;
  b) $C_1$-$C_4$ alkylene-$R^2$;
  c) $CH_2CH_2O(CH_2)_2OCH_3$,
  d) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, $R^1$ is selected from $C(=O)R^{15}$, $CO_2R^{11}$, $C(=O)NR^{12}R^{13}$, $C(=O)NR^{21}OR^{14}$, $S(O)_2NR^{12A}R^{13A}$, and $PO(OR^{21})_2$;

$R^2$ is furyl, thienyl, or triazolonyl;

$R^{11}$ at each occurrence is independently $C_1$-$C_4$ alkyl;

$R^{12}$ and $R^{13}$ at each occurrence are each independently selected from H and $C_1$-$C_4$ alkyl;

$R^{12A}$ and $R^{13A}$ at each occurrence are each independently selected from H and $C_1$-$C_4$ alkyl;

$R^{14}$ at each occurrence is independently $C_1$-$C_4$ alkyl;

$R^{15}$ at each occurrence is independently selected from $C_1$-$C_4$ alkyl, and thienyl;

$R^{20}$ at each occurrence is independently selected from F, Cl, Br, I, $OR^{21}$, $OR^{25}$, $NR^{23}R^{24}$, NHOH, $NO_2$, CN, $CF_3$, $C_3$-$C_6$ spirocycloalkyl, =O, $C(=O)R^{22}$, $CO_2R^{21}$, $C(=O)NR^{23}R^{24}$, and $NR^{21}C(=O)R^{22}$;

$R^{21}$ at each occurrence is independently selected from H and $C_1$-$C_4$ alkyl;

$R^{22}$ at each occurrence is independently $C_1$-$C_4$ alkyl;

$R^{23}$ and $R^{24}$ at each occurrence are each independently selected from H and $C_1$-$C_4$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

with the following proviso:
  1) when R=H, Y is ($C_1$-$C_4$ alkylene)-$R^1$, and $R^1$ is $CO_2R^{11}$ or $C(=O)NR^{12}R^{13}$, then the alkylene group must be substituted with a spirocycloalkyl group.

In still more aspects, there are compounds of formula (VI) wherein R is H; or $R^1$ selected from $C(=O)R^{15}$, $CO_2R^{11}$, $C(=O)NR^{12}R^{13}$, $C(=O)NR^{21}OR^{14}$, $S(O)_2NR^{12A}R^{13A}$, and $PO(OR^{21})_2$; or Y is $C_1$-$C_4$ alkylene-$R^1$.

In additional aspects of the present invention there are included compounds of any of the preceding formulas wherein q is 1 or 2. In certain aspects, q is 0. In other aspects q is 1. In further aspects, q is 2.

In other aspects of the present invention, there are included compounds of any of the preceding formulas wherein q can be any moieties of the previous embodiments, and R can be selected as follows. In one aspect, R is H. In other aspects, R is $C_1$-$C_6$ alkyl. In additional aspects, R is $C_1$-$C_4$ alkyl, preferably methyl or ethyl, and more preferably methyl.

In certain aspects of the present invention, there are included compounds of any of the preceding formulas wherein q and R can be any moieties of the previous embodiments, and rings A and B can be selected as follows. In one aspect, rings A and B are phenylene. In other aspects, rings A and B are each independently selected from: a) a 6-membered aromatic carbocyclic ring in which from 1 to 3 carbon atoms may be replaced by nitrogen atoms, preferably pyridylene, pyrazinylene, or pyrimidinylene; and b) a 5-membered aromatic carbocyclic ring in which either: i) one carbon atom may be replaced with an oxygen, nitrogen, or sulfur atom; ii) two carbon atoms may be replaced with a sulfur and a nitrogen atom, an oxygen and a nitrogen atom, or two nitrogen atoms; or iii) three carbon atoms may be replaced with three nitrogen atoms, one oxygen and two nitrogen atoms, or one sulfur and two nitrogen atoms. In an additional aspect, rings A and B are each independently selected from phenylene, pyridylene, thienylene, or a 5-membered aromatic ring in which one or two carbon atoms may be replaced with a nitrogen atom. In a further aspect, rings A and B are each independently selected from phenylene, pyridylene, pyrazinylene, pyrimidinylene, pyrrolylene, pyrazolylene, imidazolylene, furylene, and thienylene.

In another aspect of the present invention, there are included compounds of any of the preceding formulas wherein q, R, and rings A and B can be any moieties of the previous embodiments, and X can be selected as follows. In one aspect, X is not present, is a bond, O, $C_2$ alkylene, or $C(=O)$. In a further aspect, X is not present or is a bond. In another aspect, X is not present, and preferably the A-B—X moiety is $Ph_2CH$. In an additional aspect, X is a bond, and preferably the tricyclic A-B—X moiety is fluorenyl. In another aspect, X is O, $S(O)_y$, $NR^{10}$, and preferably O. Another aspect includes X as $C_2$ alkylene. In a further aspect, X is $C_{2-3}$ alkenylene, $C(=O)$, $C(R^{21})_2NR^{10}$, $C(R^{21})=N$, $N=C(R^{21})$, $C(=O)N(R^{10})$, or $NR^{10}C(=O)$.

In certain aspects of the present invention, there are included compounds of any of the preceding formulas wherein q, R, rings A and B, X and Y can be any moieties of the previous embodiments, and Y is $C_1$-$C_6$ alkylene-$R^1$, particularly those where Y is $C_1$-$C_4$ alkylene-$R^1$, or Y is $CH_2$—$R^1$ or Y is $CH_2CH_2$—$R^1$.

Other aspects of the present invention include compounds of any of the preceding formulas wherein q, R, rings A and B, and X can be any moieties of the previous embodiments, and Y can be selected as follows. One aspect is where Y is $C_1$-$C_6$ alkylene-$R^2$, particularly those where $R^2$ is furyl, thienyl or triazinyl, or 2-triazolonyl. In another aspect, Y is $C_1$-$C_6$ alkylene-$O(CH_2)_pOR^{21}$, particularly those where Y is $CH_2CH_2O(CH_2)_2OCH_3$. In a further aspect, Y is $C_6$ alkyl substituted with one or two $OR^{21}$ groups, wherein said alkyl group is further optionally substituted with 1-3 $R^{20}$ groups, and in particular Y is $CH_2C(OH)(CH_3)_2$, or $CH_2C(CH_3)_2OH$, or $CH_2C(OH)_2CF_3$, or $CH_2C(OH)(C=CH)_2$, or $CH_2CH(OH)CH_3$. In an additional aspect, Y is $CH_2CR^{21}=C(R^{21})_2$, and in particular Y is $CH_2CH=CH_2$, or $CH_2C(=C)CH_3$.

Additional aspects of the present invention include compounds of any of the preceding formulas wherein q, R, rings A and B, X and Y can be any moieties of the previous embodiments, and Y is $(C_1$-$C_4$ alkylene$)_m$-$Z^1$—$(C_1$-$C_4$ alkylene$)_n$-$R^1$, particularly those where Y is $C_1$-$C_4$ alkylene-$Z^1$—$R^1$, or Y is $Z^1$—$C_1$-$C_4$ alkylene-$R^1$, or Y is $C_1$-$C_4$ alkylene-$Z^1$—$C_1$-$C_4$ alkylene-$R^1$.

Further aspects of the present invention include compounds of any of the preceding formulas wherein q, R, rings A and B, X, and Y can be any moieties of the previous embodiments, and $Z^1$ can be selected as follows. In one aspect, $Z^1$ is $CR^{21}=CR^{21}$, $C=C(R^{21})$, $C≡C$, or phenylene, or more particularly where $Z^1$ is $CR^{21}=CR^{21}$ or $Z^1$ is phenylene. Other aspects include compounds where $Z^1$ is $CR^{21}=CR^{21}$, or $C≡C$. Other aspects include compounds where $Z^1$ is $C_3$-$C_6$ cycloalkylene, and in particular, cyclopentylene or cyclohexylene. Other aspects include compounds where $Z^1$ is 5-10 membered heteroarylene, in particular 5-6 membered heteroarylenes containing nitrogen, preferably containing 1 or 2 nitrogen atoms. Additional aspects include compounds where $Z^1$ is 3-6 membered heterocycloalkylene.

Further aspects of the present invention include compounds of any of the preceding formulas wherein q, R, rings A and B, X and Y can be any moieties of the previous embodiments, and Y is $C_1$-$C_4$ alkylene-$Z^2$—$C_1$-$C_4$ alkylene or Y is $C_1$-$C_4$ alkylene-$Z^2$, wherein $Z^2$ is O, $NR^{10A}$, or $S(O)_y$, particularly those where $Z^2$ is O. Additional aspects include any of the above embodiments of Y wherein $Z^2$ is $NR^{10A}$.

Further aspects of the present invention include compounds of any of the preceding formulas wherein q, R, rings A and B, X, Y, $Z^1$, and $Z^2$ can be any moieties of the previous embodiments, and $R^1$ can be any moiety selected from the following enumerated paragraphs:

1. $NR^{12}R^{13}$, particularly those wherein $R^{12}$ and $R^{13}$ at each occurrence are each independently selected from H and $C_1$-$C_6$ alkyl, or those where $R^{12}$ and $R^{13}$, together with the nitrogen to which they are attached, form a 5-6 membered heterocycloalkyl, particularly pyrrolidinyl, piperidinyl, or morpholinyl.
2. $NR^{21}C(=O)R^{14}$.
3. $C(=O)R^{15}$, particularly those where $R^{15}$ is $C_1$-$C_4$ alkyl, or thienyl.
4. $CO_2R^{11}$, particularly those where $R^{11}$ is $C_1$-$C_4$ alkyl.
5. $OC(=O)R^{11}$.
6. $C(=O)NR^{12}R^{13}$.
7. $C(=O)NR^{12}OR^{14}$.
8. $C(=NR^{11})NR^{12}R^{13}$.
9. $NR^{21}S(O)_2R^{11}$.
10. $S(O)_2NR^{12}R^{13}$.
11. $NR^{21}S(O)_2NR^{12}R^{13}$.
12. $PO(OR^{21})_2$.

Other additional aspects of the present invention include compounds of any of the preceding formulas wherein q, R, rings A and B, X, Y, $Z^1$, and $Z^2$ can be any moieties of the previous embodiments, and $R^1$ can be a combination of the values selected from the previous enumerated paragraphs. The preceding enumerated paragraphs may be combined to further define additional preferred embodiments of compounds of any of the preceding formulas. For example, one such combination includes $NR^{12}R^{13}$, $NR^{21}C(=O)R^{14}$, $C(=O)R^{15}$, $CO_2R^{11}$, $OC(=O)R^{11}$, $C(=O)NR^{12}R^{13}$, $C(=NR^{11})NR^{12}R^{13}$, $NR^{21}S(O)_2R^{11}$, $S(O)_2NR^{12}R^{13}$, $NR^{21}S(O)_2NR^{12}R^{13}$, or $PO(OR^{21})_2$. An additional combination includes $NR^{12}R^{13}$, $NR^{21}C(=O)R^{14}$, $C(=O)NR^{12}R^{13}$, $C(=NR^{11})NR^{12}R^{13}$, $NR^{21}S(O)_2R^{11}$, $S(O)_2NR^{12}R^{13}$, $NR^{21}S(O)_2NR^{12}R^{13}$, or $PO(OR^{21})_2$.

A third such combination includes $NR^{12}R^{13}$, $NR^{21}C(=O)R^{14}$, $C(=O)R^{15}$, $C(=O)NR^{12}R^{13}$, $C(=O)NR^{21}OR^{14}$, $NR^{21}S(O)_2R^{11}$, $S(O)_2NR^{12}R^{13}$, and $PO(OR^{21})_2$.

A fourth such combination includes $NR^{12}R^{13}$, $NR^{21}C(=O)R^{14}$, $C(=O)NR^{12}R^{13}$, $NR^{21}S(O)_2R^{11}$, or $S(O)_2NR^{12}R^{13}$.

A fifth such combination includes $NR^{12}R^{13}$, $NR^{21}C(=O)R^{14}$, $C(=O)R^{15}$, $C(=O)NR^{21}OR^{14}$, $NR^{21}S(O)_2R^{11}$, $S(O)_2NR^{12}R^{13}$, and $PO(OR^{21})_2$.

A sixth such combination includes $C(=O)R^{15}$, $C(=O)NR^{21}OR^{14}$, $S(O)_2NR^{12A}R^{13A}$, and $PO(OR^{21})_2$.

A seventh such combination includes $C(=O)R^{15}$, $C(=O)NR^{12}R^{13}$, $C(=O)NR^{21}OR^{14}$, $S(O)_2NR^{12A}R^{13A}$, and $PO(OR^{21})_2$.

An eighth such combination includes $NR^{21}C(=O)R^{14}$, $C(=O)NR^{12}R^{13}$, $NR^{21}S(O)_2R^{11}$, and $S(O)_2NR^{12}R^{13}$.

Further aspects of the present invention include compounds of any of the preceding formulas wherein q, R, rings A and B, X, y, $Z^1$, $Z^2$, and $R^1$ can be any moieties of the previous embodiments, and $R^{12}$ and $R^{13}$ are independently H or $C_1$-$C_6$ alkyl, or where $R^{12}$ and $R^{13}$, together with the nitrogen to which they are attached, form a 3-7 membered heterocycloalkyl ring. In another aspects, $R^{12}$ and $R^{13}$, together with the nitrogen to which they are attached, form a 5-6 membered heterocycloalkyl ring containing from 1 to 2 nitrogen atoms, or more preferably form pyrrolidinyl, piperidinyl, or morpholinyl. In certain aspects the heterocycloalkyl rings can be substituted with one $R^{20}$ group, and in other aspects, the heterocycloalkyl rings are unsubstituted.

The following terms and expressions contained herein are defined as follows:

As used herein, the term "about" refers to a range of values from ±10% of a specified value. For example, the phrase "about 50 mg" includes ±10% of 50, or from 45 to 55 mg.

As used herein, a range of values in the form "x-y" or "x to y", or "x through y", include integers x, y, and the integers therebetween. For example, the phrases "1-6", or "1 to 6" or "1 through 6" are intended to include the integers 1, 2, 3, 4, 5, and 6. Preferred embodiments include each individual integer in the range, as well as any subcombination of integers. For example, preferred integers for "1-6" can include 1, 2, 3, 4, 5, 6, 1-2, 1-3, 1-4, 1-5, 2-3, 2-4, 2-5, 2-6, etc.

As used herein "stable compound" or "stable structure" refers to a compound that is sufficiently robust to survive isolation to a useful degree of purity from a reaction mixture, and preferably capable of formulation into an efficacious therapeutic agent. The present invention is directed only to stable compounds.

As used herein, the term "alkyl" refers to a straight-chain, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, 3-methylpentyl, 2,2-dimethylbutyl, 2,3-dimethylbutyl, hexyl, octyl, etc. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. A designation such as "$C_1$-$C_4$ alkyl" refers to an alkyl radical containing from 1 to 4 carbon atoms.

As used herein, the term "alkenyl" refers to a straight chain, or branched hydrocarbon chains of 2 to 8 carbon atoms having at least one carbon-carbon double bond. A designation "$C_2$-$C_8$ alkenyl" refers to an alkenyl radical containing from 2 to 8 carbon atoms. Examples of alkenyl groups include ethenyl, propenyl, isopropenyl, 2,4-pentadienyl, etc.

As used herein, the term "alkynyl" refers to a straight chain, or branched hydrocarbon chains of 2 to 8 carbon atoms having at least one carbon-carbon triple bond. A designation "$C_2$-$C_8$ alkynyl" refers to an alkynyl radical containing from 2 to 8 carbon atoms. Examples include ethynyl, propynyl, isopropynyl, 3,5-hexadiynyl, etc.

As used herein, the term "alkylene" refers to a substituted or unsubstituted, branched or straight chained hydrocarbon of 1 to 8 carbon atoms, which is formed by the removal of two hydrogen atoms. A designation such as "$C_1$-$C_4$ alkylene" refers to an alkylene radical containing from 1 to 4 carbon atoms. Examples include methylene (—$CH_2$—), propylidene ($CH_3CH_2CH$═), 1,2-ethandiyl (—$CH_2CH_2$—), etc.

As used herein, the term "phenylene" refers to a phenyl group with an additional hydrogen atom removed, i.e. a moiety with the structure of:

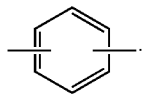

As used herein, the terms "carbocycle", "carbocyclic" or "carbocyclyl" refer to a substituted or unsubstituted, stable monocyclic or bicyclic hydrocarbon ring system which is saturated, partially saturated or unsaturated, and contains from 3 to 10 ring carbon atoms. Accordingly the carbocyclic group may be aromatic or non-aromatic, and includes the cycloalkyl and aryl compounds defined herein. The bonds connecting the endocyclic carbon atoms of a carbocyclic group may be single, double, triple, or part of a fused aromatic moiety.

As used herein, the term "cycloalkyl" refers to a saturated or partially saturated mono- or bicyclic alkyl ring system containing 3 to 10 carbon atoms. A designation such as "$C_5$-$C_7$ cycloalkyl" refers to a cycloalkyl radical containing from 5 to 7 ring carbon atoms. Preferred cycloalkyl groups include those containing 5 or 6 ring carbon atoms. Examples of cycloalkyl groups include such groups as cyclopropyl, cyclobutyl, cyclopentyl, cyclohexl, cycloheptyl, cyclooctyl, pinenyl, and adamantanyl.

As used herein, the term "aryl" refers to a substituted or unsubstituted, mono- or bicyclic hydrocarbon aromatic ring system having 6 to 12 ring carbon atoms. Examples include phenyl and naphthyl. Preferred aryl groups include unsubstituted or substituted phenyl and naphthyl groups. Included within the definition of "aryl" are fused ring systems, including, for example, ring systems in which an aromatic ring is fused to a cycloalkyl ring. Examples of such fused ring systems include, for example, indane, indene, and tetrahydronaphthalene.

As used herein, the terms "heterocycle", "heterocyclic" or "heterocyclyl" refer to a substituted or unsubstituted carbocyclic group in which the ring portion includes at least one heteroatom such as O, N, or S. The nitrogen and sulfur heteroatoms may be optionally oxidized, and the nitrogen may be optionally substituted in non-aromatic rings. Heterocycles are intended to include heteroaryl and heterocycloalkyl groups.

As used herein, the term "heterocycloalkyl" refers to a cycloalkyl group in which one or more ring carbon atoms are replaced by at least one hetero atom such as —O—, —N—, or —S—. Examples of heterocycloalkyl groups include pyrrolidinyl, pyrrolinyl, imidazolidinyl, imidazolinyl, pyrazolidinyl, pyrazolinyl, pyrazalinyl, piperidyl, piperazinyl, morpholinyl, thiomorpholinyl, tetrahydrofuranyl, dithiolyl, oxathiolyl, dioxazolyl, oxathiazolyl, pyranyl, oxazinyl, oxathiazinyl, and oxadiazinyl.

As used herein, the term "heteroaryl" refers to an aromatic group containing 5 to 10 ring carbon atoms in which one or more ring carbon atoms are replaced by at least one hetero atom such as —O—, —N—, or —S—. Examples of heteroaryl groups include pyrrolyl, furyl, thienyl, pyrazolyl, imidazolyl, thiazolyl, isothiazolyl, isoxazolyl, oxazolyl, oxathiolyl, oxadiazolyl, triazolyl (including 1,2,3 triazolyl, 1,2,4 triazolyl, and 3-oxo-1,2,4 triazolyl), oxatriazolyl, furazanyl, tetrazolyl, pyridyl, pyrazinyl, pyrimidinyl, pyridazinyl, triazinyl, picolinyl, indolyl, isoindolyl, indazolyl, benzofuranyl, isobenzofuranyl, purinyl, quinazolinyl, quinolyl, isoquinolyl, benzoimidazolyl, benzothiazolyl, benzothiophenyl, thianaphthenyl, benzoxazolyl, benzisoxazolyl, cinnolinyl, phthalazinyl, naphthyridinyl, and quinoxalinyl. Included within the definition of "heteroaryl" are fused ring systems, including, for example, ring systems in which an aromatic ring is fused to a heterocycloalkyl ring. Examples of such fused ring systems include, for example, phthalamide, phthalic anhydride, indoline, isoindoline, tetrahydroisoquinoline, chroman, isochroman, chromene, and isochromene.

As used herein, the term "arylalkyl" refers to an alkyl group that is substituted with an aryl group. Examples of arylalkyl groups include, but are not limited to, benzyl, bromobenzyl, phenethyl, benzhydryl, diphenylmethyl, triphenylmethyl, diphenylethyl, naphthylmethyl, etc.

As used herein, the term "spirocycloalkyl" refers to a cycloalkyl group bonded to a carbon chain or carbon ring moiety by a carbon atom common to the cycloalkyl group and the carbon chain or carbon ring moiety. For example, a $C_3$ alkyl group substituted with an R group wherein the R group is spirocycloalkyl containing 5 carbon atoms refers to:

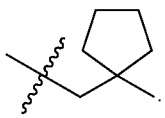

As used herein, the term "amino acid" refers to a group containing both an amino group and a carboxyl group. Embodiments of amino acids include α-amino, β-amino, γ-amino acids. The α-amino acids have a general formula HOOC—CH(side chain)-NH$_2$. In certain embodiments, substituent groups for the compounds of the present invention include the residue of an amino acid after removal of the hydroxyl moiety of the carboxyl group thereof; i.e., groups of formula —C(=O)CH(NH$_2$)-(side chain). The amino acids can be in their D, L or racemic configurations. Amino acids include naturally-occurring and non-naturally occurring moieties. The naturally-occurring amino acids include the standard 20 α-amino acids found in proteins, such as glycine, serine, tyrosine, proline, histidine, glutamine, etc. Naturally-occurring amino acids can also include non-α-amino acids (such as β-alanine, γ-aminobutyric acid, homocysteine, etc.), rare amino acids (such as 4-hydroxyproline, 5-hydroxylysine, 3-methylhistidine, etc.) and non-protein amino acids (such as citrulline, ornithine, canavanine, etc.). Non-naturally occurring amino acids are well-known in the art, and include analogs of natural amino acids. See Lehninger, A. L. *Biochemistry*, 2$^{nd}$ ed.; Worth Publishers: New York, 1975, pp. 71-77, the disclosure of which is incorporated herein by reference. Non-naturally occurring amino acids also include α-amino acids wherein the side chains are replaced with synthetic derivatives. Representative side chains of naturally occurring and non-naturally occurring α-amino acids are shown below in Table A.

TABLE A

| | | |
|---|---|---|
| H | CH$_3$ | CH(CH$_3$)$_2$ |
| CH$_2$CH(CH$_3$)$_2$ | CH(CH$_3$)CH$_2$CH$_3$ | CH$_2$OH |
| CH$_2$SH | CH(OH)CH$_3$ | CH$_2$CH$_2$SCH$_3$ |
| CH$_2$C$_6$H$_5$ | (CH$_2$)$_4$NH$_2$ | (CH$_2$)$_3$NHC(=NH)NH$_2$ |
| CH$_2$COOH | CH$_2$CH$_2$COOH | CH$_2$CONH$_2$ |
| CH$_2$CH$_2$CONH$_2$ | CH$_2$CH$_3$ | CH$_2$CH$_2$CH$_3$ |
| CH$_2$CH$_2$CH$_2$CH$_3$ | CH$_2$CH$_2$SH | CH$_2$CH$_2$OH |
| CH$_2$CH$_2$SCH$_3$ | (CH$_2$)$_3$NH$_2$ | (CH$_2$)$_2$CH(OH)CH$_2$NH$_2$ |
| (CH$_2$)$_3$NHC(=O)NH$_2$ | (CH$_2$)$_2$ONHC(=NH)NH$_2$ | CH$_2$C(=O)NHCH$_2$COOH |

As used herein, the term "subject" refers to a warm blooded animal such as a mammal, preferably a human, or a human child, which is afflicted with, or has the potential to be afflicted with one or more diseases and conditions described herein.

As used herein, a "therapeutically effective amount" refers to an amount of a compound of the present invention effective to prevent or treat the symptoms of particular disorder. Such disorders include, but are not limited to, those pathological and neurological disorders associated with the aberrant activity described herein, wherein the treatment or prevention comprises inhibiting, inducing, or enhancing the activity thereof by contacting the receptor with a compound of the present invention.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

As used herein, the term "unit dose" refers to a single dose which is capable of being administered to a patient, and which can be readily handled and packaged, remaining as a physically and chemically stable unit dose comprising either the active compound itself, or as a pharmaceutically acceptable composition, as described hereinafter.

All other terms used in the description of the present invention have their meanings as is well known in the art.

In another aspect, the present invention is directed to pharmaceutically acceptable salts of the compounds described above. As used herein, "pharmaceutically acceptable salts" includes salts of compounds of the present invention derived from the combination of such compounds with non-toxic acid or base addition salts.

Acid addition salts include inorganic acids such as hydrochloric, hydrobromic, hydroiodic, sulfuric, nitric and phosphoric acid, as well as organic acids such as acetic, citric, propionic, tartaric, glutamic, salicylic, oxalic, methanesulfonic, para-toluenesulfonic, succinic, and benzoic acid, and related inorganic and organic acids.

Base addition salts include those derived from inorganic bases such as ammonium and alkali and alkaline earth metal hydroxides, carbonates, bicarbonates, and the like, as well as salts derived from basic organic amines such as aliphatic and aromatic amines, aliphatic diamines, hydroxy alkamines, and the like. Such bases useful in preparing the salts of this invention thus include ammonium hydroxide, potassium carbonate, sodium bicarbonate, calcium hydroxide, methylamine, diethylamine, ethylenediamine, cyclohexylamine, ethanolamine and the like.

In addition to pharmaceutically-acceptable salts, other salts are included in the invention. They may serve as intermediates in the purification of the compounds, in the preparation of other salts, or in the identification and characterization of the compounds or intermediates.

The pharmaceutically acceptable salts of compounds of the present invention can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent. Such solvates are within the scope of the present invention.

The present invention also encompasses the pharmaceutically acceptable prodrugs of the compounds disclosed herein. As used herein, "prodrug" is intended to include any compounds which are converted by metabolic processes within the body of a subject to an active agent that has a formula within the scope of the present invention. Since prodrugs are known to enhance numerous desirable qualities of pharmaceuticals (e.g., solubility, bioavailability, manufacturing, etc.) the compounds of the present invention may be delivered in prodrug form. Conventional procedures for the selection and preparation of suitable prodrug derivatives are described, for example, in *Prodrugs*, Sloane, K. B., Ed.; Marcel Dekker: New York, 1992, which is incorporated herein by reference in its entirety.

It is recognized that compounds of the present invention may exist in various stereoisomeric forms. As such, the compounds of the present invention include all stereoisomeric forms, such as the diastereomeric and enantiomeric forms. The compounds are normally prepared as racemates and can conveniently be used as such, but individual stereoisomers can be isolated or synthesized by conventional techniques if so desired. Such stereoisomeric forms are included in the present invention, including the racemates, individual enantiomers and diastereomers, and mixtures thereof.

It is well known in the art how to prepare and isolate such optically active forms. Specific stereoisomers can be prepared by stereospecific synthesis using enantiomerically pure or enantiomerically enriched starting materials. The specific stereoisomers of either starting materials or products can be resolved and recovered by techniques known in the art, such as resolution of racemic forms, normal, reverse-phase, and chiral chromatography, recrystallization, enzymatic resolution, or fractional recrystallization of addition salts formed by reagents used for that purpose. Useful methods of resolving and recovering specific stereoisomers described in Eliel, E. L.; Wilen, S. H. *Stereochemistry of Organic Compounds*; Wiley: New York, 1994, and Jacques, J, et al. *Enantiomers, Racemates, and Resolutions*; Wiley: New York, 1981, each incorporated by reference herein in their entireties.

It is further recognized that functional groups present on the compounds of the present invention may contain protecting groups. For example, the amino acid side chain substituents of the compounds of the present invention can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred groups for protecting lactams include silyl groups such as t-butyldimethylsilyl ("TBDMS"), dimethoxybenzhydryl ("DMB"), acyl, benzyl ("Bn"), and methoxybenzyl groups. Preferred groups for protecting hydroxy groups include TBS, acyl, benzyl, benzyloxycarbonyl ("CBZ"), t-butyloxycarbonyl ("Boc"), and methoxymethyl. Many other standard protecting groups employed by one skilled in the art can be found in Greene, T. W. and Wuts, P. G. M., "Protective Groups in Organic Synthesis" 2d. Ed., Wiley & Sons, 1991.

SYNTHESIS AND EXAMPLES

The compounds of the present invention may be prepared in a number of methods well known to those skilled in the art, including, but not limited to those described below, or through modifications of these methods by applying standard techniques known to those skilled in the art of organic synthesis. The reagents and starting materials are commercially available, or readily synthesized by well-known techniques by one of ordinary skill in the arts. All substituents in the synthetic schemes, unless otherwise indicated, are as previously defined. All processes disclosed in association with the present invention are contemplated to be practiced on any scale, including milligram, gram, multigram, kilogram, multikilogram or commercial industrial scale.

Illustrative of compounds encompassed by the present invention that are useful in the utilities disclosed herein include those set forth in the following tables. This list is meant to be representative only and is not intended to limit the scope of the invention in any way.

TABLE 1

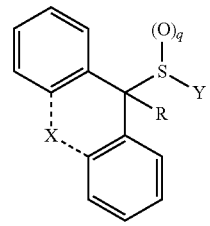

| Compound No. | q | X | R | Y | MS |
|---|---|---|---|---|---|
| I-1 | 0 | bond | CH$_3$ | CH$_2$CONH$_2$ | 292 (M + Na) |
| I-2 | 0 | bond | CH$_3$ | CH$_2$CON(CH$_3$)$_2$ | 298 (M + H) |
| I-3 | 0 | bond | CH$_3$ | CH$_2$CONH-(s)-CH(Me)CONH$_2$ | 341 (M + H) |

TABLE 1-continued

| Compound No. | q | X | R | Y | MS |
|---|---|---|---|---|---|
| I-4 | 0 | bond | CH₃ | CH₂CON(pyrrolidinyl) | 346 (M + Na) |
| I-5 | 0 | bond | C₂H₅ | CH₂CONH₂ | 306 (M + Na) |
| I-6 | 0 | bond | C₂H₅ | CH₂CON(pyrrolidinyl) | 360 (M + Na) |
| I-7 | 1 | bond | CH₃ | CH₂CONH₂ | 308 (M + Na) |
| I-8 | 1 | bond | C₂H₅ | CH₂CONH₂ | 322 (M + Na) |
| I-9 | 1 | bond | CH₃ | CH₂CON(CH₃)₂ | 314 (M + H) |
| I-10 | 1 | bond | CH₃ | CH₂CONHCH(CH₃)CONH₂ | 357 (M + H) |
| I-11 | 1 | bond | CH₃ | CH₂CON(pyrrolidinyl) | 362 (M + Na) |
| I-12 | 1 | bond | C₂H₅ | CH₂CON(pyrrolidinyl) | 376 (M + Na) |
| I-13 | 1 | not present | CH₃ | CH₂CONH₂ | 310 (M + Na) |
| II-1 | 0 | bond | H | (CH₂)₂-N-morpholinyl | 312 (M + H) |
| II-2 | 1 | bond | H | (CH₂)₂-N-morpholinyl | 328 (M + H) |
| II-3 | 1 | bond | H | (CH₂)₂-N-pyrrolidinyl | 312 (M + H) |
| II-4 | 1 | bond | H | (CH₂)₂-N-piperidinyl | 326 (M + H) |
| II-5 | 0 | bond | H | (CH₂)₂NH₂ | 242 (M + H) |
| II-6 | 0 | bond | H | (CH₂)₂NHSO₂CH₃ | 320 (M + H) |
| II-7 | 1 | bond | H | (CH₂)₂NHSO₂CH₃ | 336 (M + H) |
| II-8 | 1 | bond | H | (CH₂)₂NHCOCH₃ | 300 (M + H) |
| II-9 | 1 | bond | H | CH₂CH=CH₂ | 255 (M + H) |
| II-10 | 1 | bond | H | CH₂C(Me)=CH₂ | 269 (M + H) |
| II-11 | 0 | bond | H | CH₂CH(CH₃)₂ | 255 (M + H) |
| II-12 | 1 | bond | H | CH₂CH(CH₃)₂ | 271 (M + H) |
| II-13 | 0 | bond | H | C₃H₇ | 241 (M + H) |
| II-14 | 1 | bond | H | C₃H₇ | 257 (M + H) |
| II-15 | 1 | bond | H | CH₃ | 229 (M + H) |
| II-16 | 1 | not present | H | CH₃ | 231 (M + H) |
| II-17 | 1 | bond | H | CH₂CN | 254 (M + H) |
| II-18 | 0 | bond | CH₃ | CH₃ | 227 (M + H) |
| II-19 | 1 | bond | CH₃ | CH₃ | 243 (M + H) |

Compounds of the present invention can be generated following various synthetic protocols as shown below.

General Scheme A

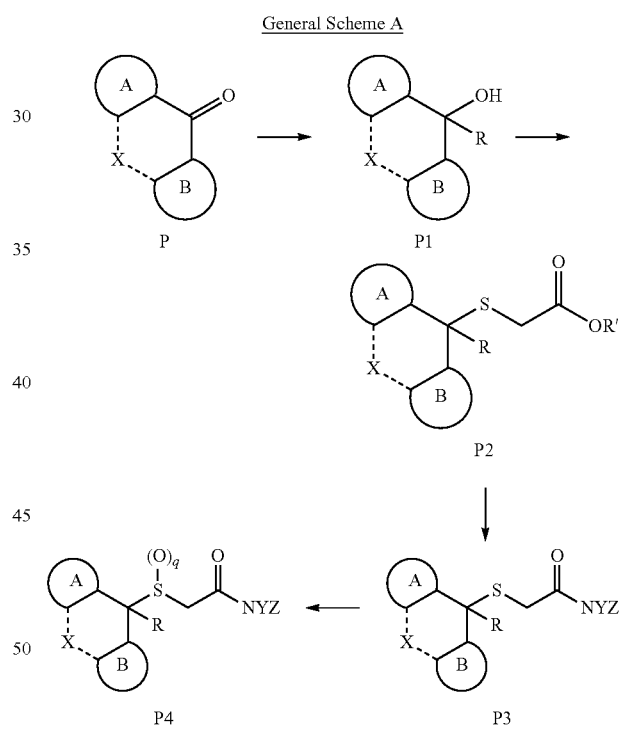

General Synthetic Procedure For Compounds P2, P3, and P4

Synthesis of compound P4 could be initiated from compound P. Thus, compound P is converted to corresponding hydroxyl compound P1 by reaction with an alkyl magnesium halide (RMgX) reagent. Compound P1 could then be reacted with a thiol compound (containing a terminal carbalkoxy group), in presence of an organic acid, e.g. trifluoroacetic acid, to generate compound P2. Conversion of compound P2 to compound P3 via the intermediacy of a carboxylic acid moiety could be affected by basic hydrolysis with LiOH followed by amidation reaction. Oxidation of compound P3 by an appropriate agent e.g. hydrogen peroxide in acidic medium or m-chloroperbenzoic acid in an organic solvent produces compound P4.

Scheme I

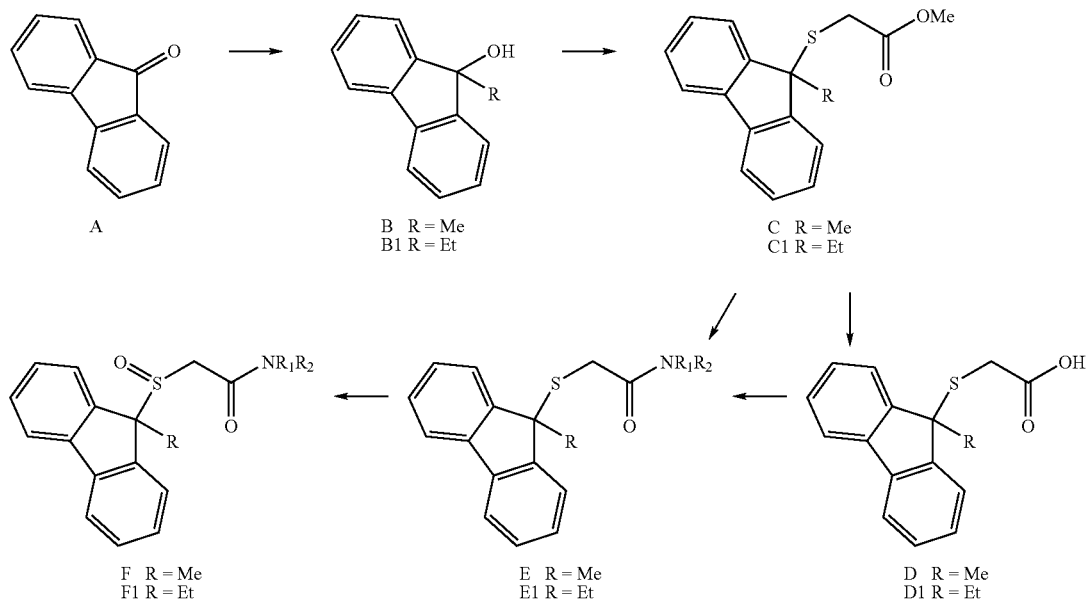

Preparation of Compound B

To a stirring solution of compound A (5 g, 27.7 mmol) in dry THF (60 mL) at 0° C., under $N_2$, was added MeMgBr (3M in diethyl ether, 9.24 mL). The cooling bath was removed and the mixture was stirred for an additional 1.5 h. More MeMgBr (0.8 ml) was added to the reaction mixture followed by additional stirring for another 3 h. The reaction was carefully quenched with ice-water and extracted into ethyl acetate (3×100 mL). The combined organic layers were washed with brine (1×50 mL), dried ($MgSO_4$), and concentrated to yield compound B (4.76 g): $^1$H-NMR (DMSO-$d_6$) δ 7.73 (d, 2H), 7.53 (dd, 2H), 7.36-7.28 (m, 4H), 5.51 (s, 1H), 1.57 (s, 3H).

Preparation of Compound B1

This compound was prepared following the similar procedure as described previously for the synthesis of compound B, except that EtMgBr was used in place of MeMgBr. Thus, starting with 5 g of compound A, 2.69 g of compound B1 was obtained: $^1$H-NMR (DMSO-$d_6$) δ 7.73 (d, 2H), 7.47 (d, 2H), 7.36-7.27 (m, 4H), 5.51 (s, 3H), 2.02 (q, 2H), 0.42 (t, 3H).

Preparation of Compound C

A mixture of compound B (1.5 g, 7.6 mmol), methyl thioglycolate (0.68 mL, 7.6 mmol) and trifluoroacetic acid (0.58 mL, 7.6 mmol) in $CH_2Cl_2$ (15 mL) was stirred at room temperature for 18 h, quenched with sat. sodium bicarbonate and extracted into $CH_2Cl_2$ (3×50 mL). The combined organic layers were washed with brine (1×50 mL), dried ($MgSO_4$) and concentrated to give a crude product that was purified by silica gel column chromatography (hexane:ethyl acetate::8:1) to yield 1.8 g of product as a pale yellow solid: $^1$H-NMR (DMSO-$d_6$) δ 7.84-7.82 (m, 2H), 7.57-7.55 (m, 2H), 7.41-7.34 (m, 4H), 3.21 (s, 3H), 2.58 (s, 2H), 1.71 (s, 3H).

Preparation of Compound C1

This compound was prepared following the similar procedure as described previously for the synthesis of compound C, except that compound B1 was used in place of compound B. Thus, starting with 2.68 g of compound B1, 3.7 g of product was obtained: $^1$H-NMR (DMSO-$d_6$) δ 7.84-7.82 (m, 2H), 7.51-7.49 (m, 2H), 7.41-7.34 (m, 4H), 3.21 (s, 3H), 2.58 (s, 2H), 2.23 (q, 2H), 0.35 (t, 3H).

Preparation of Compound D

To a solution of compound C (0.5 g, 1.75 mmol) in methanol (6 mL) at room temperature was added LiOH.$H_2O$ (0.088 g, 2.1 mmol) in water (2 mL). The reaction mixture was stirred at this temperature for 3 h and then at 60° C. for 1 h. It was then concentrated, diluted with water (20 mL), washed with diethyl ether (2×15 mL), acidified (pH ~2) with 2N HCl and extracted with ethyl acetate (2×50 mL). The combined organic layers were washed with brine (1×20 ml), dried ($MgSO_4$) and concentrated in vacuo to give 0.41 g of product: $^1$H-NMR (CDCl$_3$): δ 9.30 (bs, 1H), 7.70 (d, 2H), 7.60 (d, 2H), 7.30 (m, 4H), 2.50 (s, 2H), 1.80 (s, 3H).

Example I-1

Synthesis of Compound I-1 (Compound E, Wherein $NR_1R_2$=$NH_2$)

To a refluxing solution of compound D (2.35 g, 8.6 mmol) in benzene (18 mL) was added thionyl chloride (2.6 mL, 34.7 mmol) dropwise. The reaction mixture was heated for 1 h, concentrated in vacuo, dissolved in dichloromethane (50 mL) and treated with 28% $NH_4OH$ (10 mL) at room temperature. The mixture was vigorously stirred for 1 h and the layers were separated. The aqueous layer was extracted with dichloromethane (1×50 mL). The combined organic layers were washed with water (2×20 mL), brine (1×20 ml), dried ($MgSO_4$), and concentrated to give a residue that on trituration with ether generated 1.54 g of product: $^1$H-NMR (CDCl$_3$): δ 7.70 (d, 2H), 7.60 (d, 2H), 7.30 (m, 4H), 5.80 (bs, 1H), 5.10 (bs, 1H), 2.50 (s, 2H), 1.80 (s, 3H).

Example I-2

Synthesis of Compound I-2 (Compound E, Wherein $NR_1R_2$=$NMe_2$)

This compound was prepared following the similar procedure as described in Example I-1 wherein dimethylamine gas was used in place of 28% $NH_4OH$ in the amidation step and the final product was purified by silica gel column chromatography (ethyl acetate:hexanes::1:1). Thus, starting from 2.3 g of compound D, 1.8 g of product was obtained: $^1$H-NMR (CDCl$_3$): δ 7.70-7.60 (m, 4H), 7.30 (m, 4H), 2.70 (s, 3H), 2.60 (s, 3H), 2.50 (s, 2H), 1.80 (s, 3H).

Example I-3

Synthesis of Compound I-3 (Compound E, Wherein NR$_1$R$_2$=NH-(s)-CH(Me)CONH$_2$)

To a solution of compound D (2 g, 7.35 mmol) in DMF (10 mL) at room temperature was successively added 2-(1H-benzotriazol-1-yl)-1,1,3,3-tetramethyluronium tetrafluoroborate ("TBTU")(1.2 eqv) and N-methylmorpholine ("NMM")(1 mL). The mixture was stirred for 10 min, treated dropwise with a mixture of alanine hydrochloride (1.37 g, 11 mmol) and NMM (2 mL) in DMF (15 ml) and stirred overnight. The reaction mixture was then diluted with water and extracted with ethyl acetate (3×50 mL). The combined organic layers were washed with water (3×20 mL), brine (1×20 mL), dried (MgSO$_4$) and concentrated to give a crude solid that, on trituration with ether, generated 2.50 g of product: $^1$H-NMR (DMSO-d$_6$): δ 7.60-7.10 (m, 8H), 7.00 (s, 1H), 6.80 (s, 1H), 3.70 (m, 1H), 2.30 (m, 2H), 2.20 (s, 1H), 1.50 (s, 3H), 0.80 (d, 3H).

Example I-4

Synthesis of Compound I-4 (Compound E, Wherein NR$_1$R$_2$=N-pyrrolidinyl)

A mixture of compound C (1.76 g, 6.2 mmol), pyrrolidine (2.58 mL, 31 mmol) and methanol (10 mL) was stirred at room temperature for 65 h and concentrated to generate a crude product that was purified by silica gel column chromatography (hexane:ethyl acetate::1:1) to yield 1.32 g of product: $^1$H-NMR (DMSO-d$_6$) δ 7.85-7.83 (m, 2H), 7.62-7.60 (m, 2H), 7.42-7.35 (m, 4H), 3.00 (t, 2H), 2.83 (t, 2H), 2.54 (s, 2H), 1.72 (s, 3H), 1.69-1.59 (m, 4H).

Example I-5

Synthesis of Compound I-5 (Compound E1, Wherein NR$_1$R$_2$=NH$_2$)

A mixture of compound C1 (1.24 g, 4.2 mmol), methanol (5 mL) and NH$_3$ gas was maintained at 50° C. in a sealed tube for 20 h, cooled to room temperature, recharged with NH$_3$ gas and kept at 50° C. for an additional 20 h. The reaction mixture was then concentrated and triturated with ether to yield 0.94 g of product. This material was used in the next step without any further purification: $^1$H-NMR (DMSO-d$_6$) δ 7.86-7.82 (m, 2H), 7.65-7.52 (2H), 7.42-7.35 (m, 4H), 7.12 (br s, 1H), 6.83 (br s, 1H), 2.48 (s, 2H), 2.25 (q, 2H), 0.35 (t, 3H).

Example I-6

Synthesis of Compound I-6 (Compound E1, Wherein NR$_1$R$_2$=N-pyrrolidinyl)

This compound was prepared following the similar procedure as described previously in Example I-5 wherein pyrrolidine was used in place of 28% NH$_4$OH in the amidation step that was carried out at room temperature and the final product was purified by silica gel column chromatography (ethyl acetate:hexanes::1:1). Thus, starting from 1.29 g of compound I-2, 1.38 g of product was obtained: $^1$H-NMR (DMSO-d$_6$) δ 7.86-7.83 (m, 2H), 7.56-7.54 (m, 2H), 7.41-7.35 (m, 4H), 3.01 (t, 2H), 2.84 (t, 2H), 2.24 (q, 2H), 2.50 (m, 2H), 1.68-1.59 (m, 4H), 0.37 (t, 3H).

Example I-7

Synthesis of Representative Compound I-7 (Compound F, Wherein NR$_1$R$_2$=NH$_2$)

A mixture of compound I-1 (1.18 g, 4.3 mmol) in gl. acetic acid (10 mL) and 50% aqueous H$_2$O$_2$ (1.1 eqv) was stirred at room temperature 2 h, treated with additional peroxide (0.2 eqv) and stirred for another 1 h. It was then diluted with water (20 mL) and extracted with ethyl acetate (3×75 mL). The combined organic layers were washed with 2% aq. sodium bicarbonate (2×10 mL), water (1×10 mL), and brine (1×10 mL), dried (MgSO$_4$), and concentrated to give a crude solid that on trituration with ether generated 1.09 g of product: $^1$H-NMR (DMSO-d$_6$): δ 7.80 (t, 2H), 7.50-7.30 (m, 7H), 6.90 (b, 1H), 2.10-1.90 (q, 2H), 1.80 (s, 3H).

Example I-8

Synthesis of Compound I-8 (Compound F1, wherein NR$_1$R$_2$=NH$_2$)

Compound I-5 was oxidized to give the product following the same procedure as described in Example I-7; $^1$H-NMR (DMSO-d$_6$): δ 8.00 (m, 2H), 7.50 (m, 6H), 7.40 (d, 1H), 7.10 (d, 1H), 2.50 (m, 2H), 2.20 (dd, 2H), 0.50 (t, 3H).

Example I-9

Synthesis of Compound I-9 (Compound F, Wherein NR$_1$R$_2$=NMe$_2$)

Compound I-2 was oxidized to give the product following the same procedure as described in Example I-7; $^1$H-NMR (DMSO-d$_6$): δ 8.20-7.50 (series of m, 8H), 2.80 (s, 3H), 2.50 (s, 3H), 2.60-2.30 (2 d, 2H), 2.10 (s, 3H).

Example I-10

Synthesis of Compound I-10 (Compound F, Wherein NR$_1$R$_2$=NH-(s)-CH(Me)CONH$_2$)

Compound I-3 was oxidized to give the product (mixture of diastereomers) following the same procedure as described in Example I-7; $^1$H-NMR (DMSO-d$_6$): δ 8.40-7.50 (m, 8H), 7.40-6.80 (2 sets of d, 2H), 4.00 (m, 1H), 3.20 (q, 1H), 2.50-2.30 (m, 2H), 1.80 (s, 3H), 1.10 (m, 3H).

Example I-11

Synthesis of Compound I-11 (Compound F, Wherein NR$_1$R$_2$=N-pyrrolidinyl)

Compound I-4 was oxidized to give the product following the same procedure as described in Example I-7; $^1$H-NMR (DMSO-d$_6$): δ 8.00 (m, 2H), 7.50 (m, 6H), 3.10-2.70 (series of m, 4H), 2.20 (dd, 2H), 1.90 (s, 3H), 1.70 (m, 4H).

Example I-12

Synthesis of Compound I-12 (Compound F1, wherein NR$_1$R$_2$=N-pyrrolidinyl)

Compound I-6 was oxidized to give the product following the same procedure as described in Example I-7; $^1$H-NMR (DMSO-d$_6$): δ 8.00 (m, 2H), 7.50 (m, 6H), 3.10 (m, 2H), 2.70 (m, 4H), 2.20 (dd, 2H), 1.70 (m, 4H), 0.50 (t, 3H).

Example I-13

Synthesis of Compound I-13

Starting with benzophenone in place of compound A in Scheme I, the product was prepared following the same multistep synthetic sequence as described in the previous examples; $^1$H-NMR (DMSO-d$_6$): δ 7.50 (b, 1H), 7.40-7.20 (m, 10H), 7.10 (b, 1H), 2.80 (dd, 2H), 1.80 (s, 3H).

General Scheme B

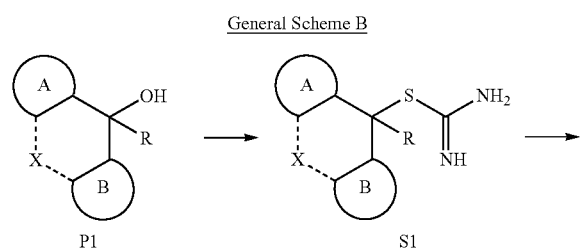

General Synthetic Procedure For Compounds In General Scheme B:

Synthesis of various compounds can be initiated from compound P1. Thus, compound P1 is converted to corresponding compound S1 by reaction with thiourea in an acidic medium e.g. HBr. Compound S1 could then be hydrolyzed to corresponding thiol compound T1 in a basic hydrolysis step. In situ alkylation of compound T1 by an appropriate alkylating agent containing a terminal amino group generates compound U1 that could further be derivatized in the amino position in subsequent steps. Oxidation of compound U1 by an appropriate agent e.g. hydrogen peroxide in acidic medium or m-chloroperbenzoic acid produces compound V1.

Scheme II

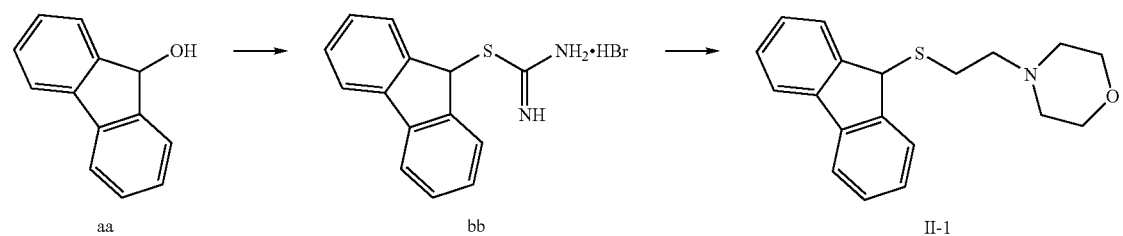

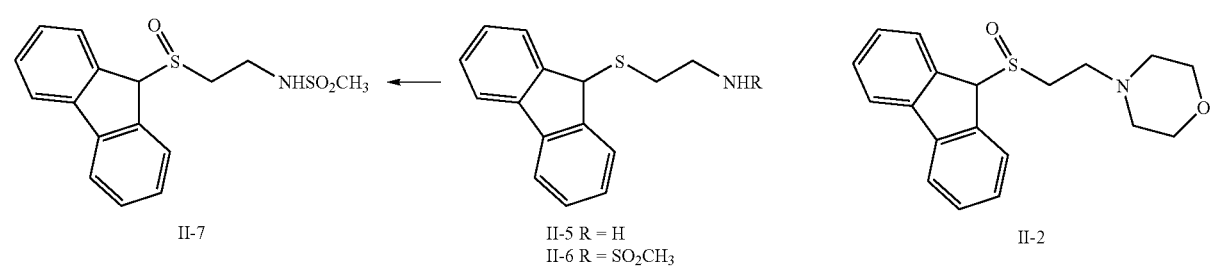

-continued

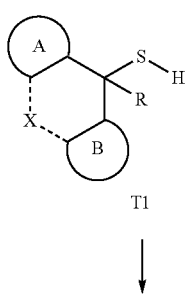

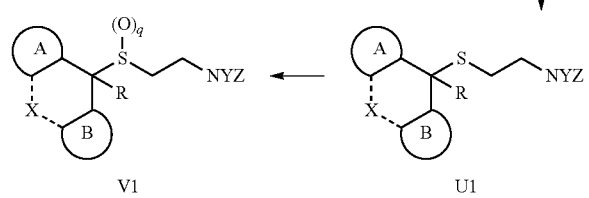

Preparation of Compound bb

Synthesis of compound bb had been disclosed in U.S. Pat. No. 6,492,396 which is incorporated herein by reference in its entirety.

Example II-1

Synthesis of Compound II-1

To a mixture of compound bb (2.13 g, 6.89 mmol) in water (5 mL) at 70° C. was added a mixture of 4-(2-chloroethyl)morpholine hydrochloride (1.53 g, 8.2 mmol) in water (5 mL) and 10N NaOH (3 mL). The reaction mixture was heated at 110° C. for 1 h, cooled and extracted into ether (3×50 mL). The combined organic layers were washed with water (1×15 mL), brine (1×15 ml), dried (MgSO$_4$) and concentrated to generate a crude product that was purified by flash chromatography (silica gel; solvent: ethyl acetate:hexane::2:3) to yield 1.48 g of compound II-1: $^1$H-NMR (CDCl$_3$): δ 7.70 (m, 4H), 7.30 (m, 4H), 4.90 (s, 1H), 3.50 (m, 4H), 2.20-1.90 (m, 8H).

Example II-2

Synthesis of Compound II-2

To a cooled (−15° C.) solution of compound II-1 (1.45 g, 4.66 mmol) in dichloromethane (15 mL) was added m-chloroperbenzoic acid (77%, 0.8 g, 4.66 mmol) in portions. The reaction mixture was stirred for 1 h, quenched with 2% aq. sodium bicarbonate (50 ml), and diluted with dichloromethane (100 ml). The separated organic layers were washed with 2% aq. sodium bicarbonate (2×20 ml), water (1×20 mL), and brine (1×20 ml), dried (MgSO$_4$), filtered and concentrated to give a crude product. It was purified by flash chromatography (silica gel; ethyl acetate followed by methanol:dichloromethane::5:95) to yield an oil that on trituration with ether generated 0.067 g of compound II-2: $^1$H-NMR (CDCl$_3$): δ 7.90-7.70 (m, 3H), 7.60-7.30 (m, 5H), 5.40 (s, 1H), 3.60 (m, 3H), 2.50 (m, 1H), 2.30-2.20 (m, 5H), 1.80-1.60 (m, 3H).

Example II-3

Synthesis of Compound II-3

This compound was prepared following the same procedure as described in Examples II-1 and II-2, except that terminal morpholinyl group was replaced by a pyrrolidinyl group; $^1$H-NMR (CDCl$_3$): δ 8.00-7.30 (series of m, 8H), 5.60 (s, 1H), 3.20-2.40 (series of broad m, 8H), 1.70 (broad, 4H).

Example II-4

Synthesis of Compound II-4

This compound was prepared following the same procedure as described in Examples II-1 and II-2, except that terminal morpholinyl group was replaced by a piperidinyl group; $^1$H-NMR (CDCl$_3$): δ 8.10-7.30 (series of m, 8H), 5.60 (s, 1H), 3.20-2.40 (series of broad m, 8H), 1.70 (broad, 4H), 1.60 (broad, 2H).

Example II-5

Synthesis of Compound II-5

This compound was prepared following the same procedure as described in Example II-1 wherein 2-chloroethylamine hydrochloride was used in place of 4-(2-chloroethyl) morpholine hydrochloride as one of the reactants. This material was directly used in the next step.

Example II-6

Synthesis of Compound II-6

To a mixture of compound II-5 (0.73 g, 3.04 mmol) and triethylamine (0.47 ml, 3.4 mmol) in dichloromethane (10 mL) at 0° C. was added methanesulfonyl chloride (0.26 mL, 3.35 mmol). The cooling bath was removed and the reaction mixture was stirred at room temperature for 1 h, treated with 2N HCl (20 mL) and extracted into dichloromethane (2×25 mL). The combined organic layers were washed with water (1×10 mL), brine (1×10 mL), dried (MgSO$_4$) and concentrated to give 0.97 g of compound II-6 that was immediately taken into next step.

Example II-7

Synthesis of Compound II-7

To a mixture of compound II-6 (0.97 g, 3.03 mmol) in glacial acetic acid (10 mL) at room temperature was added H$_2$O$_2$ (50% in water, 0.247 mL). The mixture was stirred for 0.5 h, diluted with ice-water (100 mL) and stirred for an additional 0.5 h. The separated solid was filtered and washed several times with water and ether successively, and dried under high vacuum to generate 0.56 g of compound II-7: $^1$H-NMR (DMSO-d$_6$): δ 7.80 (t, 2H), 7.60 (d, 1H), 7.50 (d, 1H), 7.30 (m, 2H), 7.20 (m, 3H), 5.50 (s, 1H), 2.90 (m, 2H), 2.60 (s, 3H), 1.90 (m, 2H).

Example II-8

Synthesis of Compound II-8

This compound was prepared following the same synthetic scheme as described in Examples II-6 and II-7 except that an acetamido group was employed at the terminus; $^1$H-NMR (DMSO-d$_6$): δ 8.10-7.30 (series of m, 8H), 5.60 (s, 1H), 3.30 (s, 1H), 3.20 (m, 2H), 2.10 (m, 2H), 1.80 (s, 3H).

General Scheme C

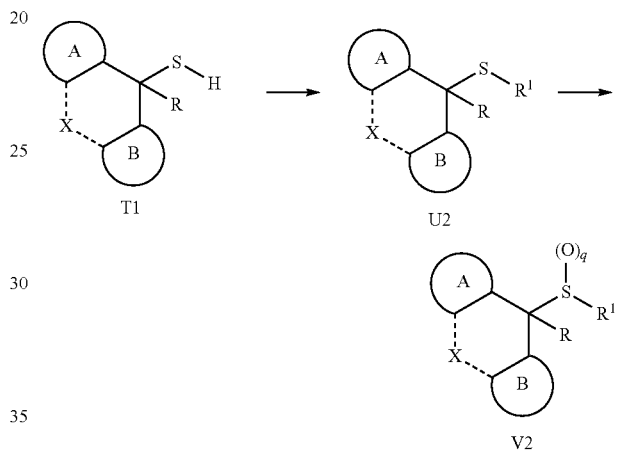

General Synthetic Procedure For Compounds in General Scheme C

Synthesis of compound V2 could be initiated from compound T1. Thus, alkylation of compound T1 by an appropriate alkylating agent in presence of a base generates compound U2 that on oxidation by an appropriate agent e.g. hydrogen peroxide in acidic medium or m-chloroperbenzoic acid produces compound V2.

Scheme IIA

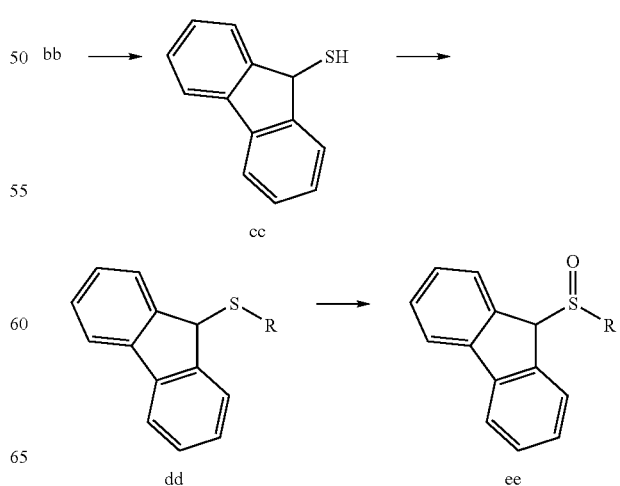

Example II-9

Synthesis of Compound II-9 (Compound ee Wherein R=—CH$_2$CH=CH$_2$)

A mixture of compound bb (14.12 g, 44 mmol), 10 N NaOH (14.9 mL) and water (109 mL) was heated at 70° C. for 0.5 h, cooled, diluted with ice-water, acidified (pH ~2) and extracted into ethyl acetate (3×100 mL). The combined organic layers were washed with water (1×50 mL) and brine (1×50 mL), dried (MgSO$_4$) and concentrated to yield 9.45 g of compound cc that was directly taken into next step without any further purification; $^1$H-NMR (DMSO-d$_6$) δ 7.89 (d, 2H), 7.76 (d, 2H), 7.43 (m, 4H), 5.21 (d, 1H), 3.55 (d, 1H).

Thus, a mixture of compound cc (2 g, 10.1 mmol) in methanol (16 mL) and sodium methoxide (0.5 M in methanol, 20.2 mL) was heated at 60° C. for 0.5 h, treated with allyl iodide (4.66 mL, 50.5 mmol), continued heating for an additional 0.5 h, cooled, and quenched with ice-water. It was then acidified (pH ~2) and extracted into ethyl acetate (3×50 mL). The combined organic layers were washed with water (1×50 mL) and brine (1×50 mL), dried (MgSO$_4$) and concentrated to yield a crude material. This material was stirred in pet. ether (20 mL) and filtered. The filtrate, upon concentration, provided 1.97 g of compound dd (R=—CH$_2$CH=CH$_2$) which was oxidized by 50% H$_2$O$_2$ to give compound II-9 following the previously described procedure in Example I-10; $^1$H-NMR (DMSO-d$_6$) δ 8.00-7.20 (series of m, 8H), 5.60 (s, 1H), 5.50 (m, 1H), 5.50 (m, 2H), 2.90 (m, 2H).

Example II-10

Synthesis of Compound II-10 (Compound ee Wherein R=—CH$_2$C(Me)=CH$_2$)

This compound was prepared following the same scheme as in Example II-9, except that a 2-methyl propylene group was employed at the terminus; $^1$H-NMR (DMSO-d$_6$) δ 8.00-7.20 (series of m, 8H), 5.60 (s, 1H), 4.90 (s, 1H), 4.60 (s, 1H), 2.60 (dd, 2H), 1.50 (s, 3H).

Example II-11

Synthesis of Compound II-11 (Compound dd Wherein R=—CH$_2$CHMe$_2$)

A mixture of compound cc (2 g, 10.1 mmol) in methanol (16 mL) and sodium methoxide (0.5 M in methanol, 20.2 mL) was heated at 60° C. for 0.5 h, treated with 1-iodo-2-methylpropane (6 mL, 50.5 mmol), heated for an additional 0.5 h, cooled, and quenched with ice-water. It was then acidified (pH ~2) and extracted into ethyl acetate (3×50 mL). The combined organic layers were washed with water (1×50 mL) and brine (1×50 mL), dried (MgSO$_4$) and concentrated to yield a crude material. This material was stirred in pet. ether (20 mL) and filtered. The filtrate, upon concentration, provided 2.21 g of compound II-11 that was directly used in the next step: $^1$H-NMR (DMSO-d$_6$) δ 7.86 (d, 2H), 7.64 (d, 2H), 7.42 (m, 4H), 5.13 (s, 1H), 1.90 (d, 2H), 1.36 (m, 1H), 0.74 (s, 3H), 0.72 (s, 3H).

Example II-12

Synthesis of Compound II-12 (Compound ee Wherein R=—CH$_2$CHMe$_2$)

To a cooled (ice-bath) solution of compound II-11 (1 g, 3.9 mmol) in gl. acetic acid (4 mL) was added 50% H$_2$O$_2$ (0.27 mL). The reaction mixture was stirred for 1 h, diluted with ethyl acetate and concentrated to give a crude product that was purified by flash chromatography (silica, solvent-gradient: hexane:ethyl acetate::4:1 to ethyl acetate) to generate 0.71 g of compound II-12: $^1$H-NMR (DMSO-d$_6$) δ 7.97 (t, 2H), 7.73 (d, 1H), 7.63 (d, 1H), 7.52 (m, 2H), 7.38 (m, 2H), 5.60 (s, 1H), 1.89 (dd, 1H), 1.76 (m, 1H), 1.66 (dd, 1H), 0.78 (d, 3H), 0.76 (d, 3H).

Example II-13

Synthesis of Compound II-13 (Compound dd Wherein R=C$_3$H$_7$)

This compound was prepared following the same procedure as described before for the synthesis of compound II-11, except that n-propyl iodide was utilized as an alkylating agent. It was immediately used in the synthesis of compound II-14.

Example II-14

Synthesis of Compound II-14 (Compound ee Wherein R=C$_3$H$_7$)

Utilizing compound II-13, this compound was prepared following the same procedure as described before for the synthesis of compound II-12; $^1$H-NMR (DMSO-d$_6$) δ 8.00-7.20 (series of m, 8H), 5.60 (s, 1H), 1.90 (2 sets of m, 2H), 1.50 (m, 2H), 0.80 (t, 3H).

Example II-15

Synthesis of Compound II-15 (Compound ee Wherein R=CH$_3$)

This compound had been described by: Kice, J. L., Lotey, H. *J. Org. Chem.* 1988, 53, 3593; this reference has been included herein in its entirety.

Example II-16

Synthesis of Compound II-16

This compound had been described by Mizuno, H., Matsuda, M., Ino, M. *J. Org. Chem.* 1981, 46, 520; this reference has been included herein in its entirety.

Example II-17

Synthesis of Compound II-14 (Compound ee Wherein R=CH$_2$CN)

This compound had been described by: Kice, J. L., Lotey, H. *J. Org. Chem.* 1988, 53, 3593; this reference has been included herein in its entirety.

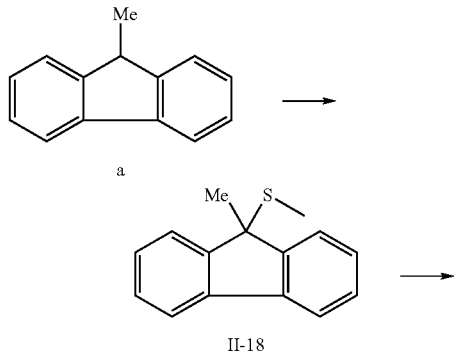

Scheme IIB

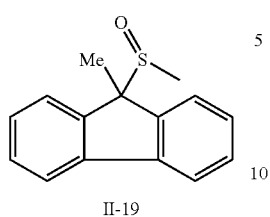

II-19

Example II-18

Synthesis of Compound II-18

To a cooled (−78° C.) solution of compound a (3.43 g, 19 mmol) in anhydrous THF (60 mL) was added n-butyl lithium in hexanes (2.5 M, 9.1 mL, 23 mmol). The reaction mixture was stirred for an additional 0.5 h, treated with dimethyl disulfide (2.54 mL, 29 mmol) in two portions over a period of 0.5 h, and stirred for another 0.5 h. It was then quenched with ice-water (50 mL) and extracted into ethyl acetate (2×50 mL). The combined organic layers were washed with brine (1×50 mL), dried (MgSO$_4$) and concentrated to give a crude material that was purified by silica-gel column chromatography (solvent: hexanes) to yield 3.33 g of compound II-18 (yellow solid): $^1$H-NMR (DMSO-d$_6$) δ 7.85-7.82 (m, 2H), 7.58-7.55 (m, 2H), 7.40-7.35 (m, 4H), 1.72 (s, 3H), 1.32 (s, 3H). The method was an adaptation from a procedure previously described in *J Med Chem* 1986, 29, 1577, which is incorporated herein by reference in its entirety.

Example II-19

Synthesis of Compound II-19

To a cooled (−78° C.) solution of compound II-18 (3.32 g, 14.7 mmol) in CH$_2$Cl$_2$ (50 mL) was slowly added a solution of m-chloroperbenzoic acid (70-75%, 3.96 g) in CH$_2$Cl$_2$ (30 mL). The reaction mixture was stirred for 2 h, treated with an additional 0.8 g of m-chloroperbenzoic acid, and stirred for another 2 h. It was then quenched with sat. NaHCO$_3$ (50 mL). The organic layer was separated and washed with sat. NaHCO$_3$ (2×50 mL), and water (1×50 mL), dried (MgSO$_4$) and concentrated to give a crude product that was purified by silica gel column chromatography (solvent gradient: 4:1 hexane/ethyl acetate to 2:1 hexane/ethyl acetate) to yield 3.06 g of compound II-19: $^1$H-NMR (DMSO-d6) δ 8.00-7.95 (m, 2H), 7.60-7.38 (m, 6H), 1.91 (s, 3H), 1.40 (s, 3H).

Additional compounds encompassed by the present invention include those set forth in the following table. This list is meant to be representative only and is not intended to limit the scope of the invention in any way. The reagents and starting materials are commercially available, or readily synthesized by well-known techniques by one of ordinary skill in the arts. All substituents in the synthetic Schemes, unless otherwise indicated, are as previously defined.

TABLE 2

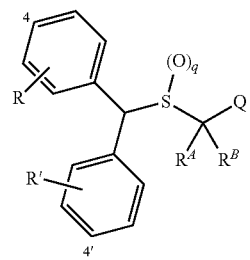

| Compound No. | R | R' | q | R$^A$ | R$^B$ | Q |
|---|---|---|---|---|---|---|
| III-1 | H | H | 0 | H | H | SO$_2$NH$_2$ |
| III-2 | H | H | 1 | H | H | SO$_2$NH$_2$ |
| III-3 | H | H | 1 | H | H | COCH$_3$ |
| III-4 | H | H | 1 | H | H | P(O)(O$^i$Pr)$_2$ |
| III-5 | H | H | 1 | H | H | C(OH)$_2$CF$_3$ |
| III-6 | H | H | 1 | H | H | CH$_2$OH |
| III-7 | H | H | 1 | H | H | CH$_2$OCH$_3$ |
| III-8 | H | H | 1 | H | H | 2-Furyl |
| III-9 | H | H | 1 | H | H | (triazolone) |
| III-10 | H | H | 1 | H | H | 2-thiophene |
| III-11 | 4-F | 4'-F | 1 | H | H | SO$_2$NH$_2$ |
| III-12 | 4-F | 4'-F | 1 | H | H | COCH$_3$ |
| III-13 | 4-F | 4'-F | 1 | H | H | CH$_2$OH |
| III-14 | 4-F | 4'-F | 1 | H | H | CH$_2$OMe |
| III-15 | 4-F | 4'-F | 1 | H | H | CH$_2$O(CH$_2$)$_2$OMe |
| IV-1 | H | H | 0 | H | H | CONHOMe |
| IV-2 | H | H | 1 | H | H | CONHOMe |
| IV-3 | H | H | 1 | H | H | CONHOEt |
| IV-4 | 4-F | 4'-F | 1 | H | H | CONHOMe |
| V-1 | H | H | 1 | H | H | CO-2-thienyl |
| V-2 | H | H | 1 | H | H | C(OH)Me$_2$ |
| V-3 | H | H | 1 | H | H | C(OH)(C≡CH)$_2$ |
| V-4 | 4-F | 4'-F | 1 | H | H | C(OH)Me$_2$ |
| V-5 | 4-F | 4'-F | 1 | H | H | CH(OH)Me |
| VI-1 | H | H | 1 | F | F | CH$_2$OH |
| VI-2 | H | H | 1 | Me | Me | CMe$_2$OH |
| VII-1 | H | H | 0 | Cyclohexyl | | CO$_2$CH$_3$ |
| VII-2 | H | H | 0 | Cyclohexyl | | CONH$_2$ |
| VII-3 | H | H | 1 | Cyclohexyl | | CONH$_2$ |
| VIII-1 | H | H | 0 | Cyclopentyl | | CONH$_2$ |
| VIII-2 | H | H | 1 | Cyclopentyl | | CONH$_2$ |
| IX-1 | H | H | 0 | Cyclobutyl | | CONH$_2$ |
| IX-2 | H | H | 1 | Cyclobutyl | | CONH$_2$ |
| IX-3 | 4-F | 4'-F | 1 | Cyclobutyl | | CONH$_2$ |
| X-1 | H | H | 1 | Cyclopropyl | | CONH$_2$ |

Scheme III

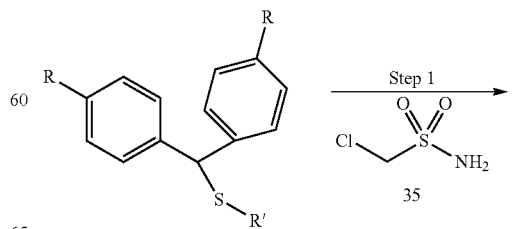

-continued

III-1

III-2 a R=H, R'=C(=NH)NH$_2$·HBr b R=F, R'=C(=NH)NH$_2$·HBr c R=H, R'=H

Reagents for Step 1, compounds 31a and 31b: (i) 10 N NaOH/EtOH/70° C.; (ii) compound 35, reflux 2 h. Step 2: 50% H$_2$O$_2$ in water/HOAc/RT or m-chloroperbenzoic acid, dichloromethane, 0° C.

Reagents for Step 1, compound 31c: NaH/DMF/compound 35/room temperature to 70° C.

Preparation of Compounds 31 and 35

The preparation of compounds 31c (U.S. Pat. No. 4,066, 686) and 35 (El-Hewehi, Z.; Runge, F. *J. Prakt. Chem.* 1962, 16, 297) were described in the literature, and both references are incorporated herein in their entireties.

Example III-1

Synthesis of Compound III-1

To a stirred mixture of NaH (60% in oil, 745 mg, 18.62 mmol) in dry DMF (15 mL) at room temperature and under argon was added dropwise a solution of compound 31c (3.33 g, 16.64 mmol) in dry DMF (3 mL). The mixture was stirred at room temperature for 15 min. The reaction mixture was then treated with compound 35 (2.2 g, 16.98 mmol) followed by heating at 70° C. for 4 h. It was then cooled to room temperature, concentrated at high vacuum, diluted with water and extracted into EtOAc. The combined organic layers were washed successively with water and brine, dried (MgSO$_4$) and concentrated to give a crude product that was purified by flash chromatography (silica gel, hexane:EtOAc::3:2) to yield compound III-1 (3.9 g): $^1$H-NMR (DMSO-d$_6$): δ 7.18-6.8 (series of m, 11H), 6.65 (s, 1H), 5.25 (s, 1H), 2.90 (s, 2H).

Example III-2

Synthesis of Compound III-2

To a solution of the compound III-1 (3.88 g, 13.24 mmol) in acetic acid (25 mL) was added hydrogen peroxide (50% solution in water, 910 µL). The reaction mixture was stirred at room temperature overnight. Solvent was removed and the crude product was stirred in EtOAc, filtered and dried to generate compound III-2 (1.08 g) m.p.: 165-166° C., $^1$H-NMR (DMSO-d$_6$): δ 7.54-7.35 (series of m, 12H), 5.52 (s, 1H), 4.23 (d, 1H), 3.93 (d, 1H). MS: 331.91 (M+Na), Example III-3

Synthesis of Compound III-3

Utilizing compound 31c and chloroacetone in first step, compound III-3 was synthesized; mp.: 81-82° C.; $^1$H-NMR (DMSO-d$_6$): δ 7.56-7.32 (series of m, 10H), 5.34 (s, 1H), 3.66 (dd, 2H), 2.13 (s, 3H). MS: 294.99 (M+Na)

Example III-4

Synthesis of Compound III-4

Utilizing compound 31c and diisopropylbromomethyl phosphonate in first step, compound III-4 was synthesized; mp: 127-128° C., $^1$H-NMR (DMSO-d$_6$): δ 7.53-7.34 (series of m, 10H), 5.42 (s, 1H), 4.58 (m, 2H), 2.94 (m, 2H). MS: 394.79 (M+H).

Example III-5

Synthesis of Compound III-5

Utilizing compound 31c and 3-bromo-1,1,1-trifluoro-propan-2-one in first step, compound III-5 was synthesized; m.p.: 121-122° C.; $^1$H-NMR (DMSO-d$_6$): δ 7.72-7.32 (series of m, 12H), 5.37 (s, 1H), 3.02 (d, 1H), 2.69 (d, 1H). MS: 366.92 (M+Na).

Example III-6

Synthesis of Compound III-6

Utilizing compound 31c and 2-chloroethoxytrimethylsilane in first step, compound III-6 was synthesized; mp.: 134° C., $^1$H-NMR (DMSO-d$_6$): δ 7.64-7.30 (series of m, 10H), 5.24 (s, 1H), 4.94 (m, 1H), 3.69 (m, 2H), 2.64-2.49 (two sets of m, 2H). MS: 260.98 (M+H).

Example III-7

Synthesis of Compound III-7

Utilizing compound 31c and bromoethylmethyl ether in first step, compound III-7 was synthesized; m.p.: 71-72° C.; $^1$H-NMR (DMSO-d$_6$): δ 7.52-7.31 (series of m, 10H), 5.21 (s, 1H), 3.51 (m, 2H), 3.31 (s, 3H), 2.75-2.53 (two m, 2H). MS: 274.95 (M+H), Example III-8

Synthesis of Compound III-8

Utilizing furan-2-yl-methanethiol in place of 31a/b/c, and bromodiphenylmethane in step 1, compound III-8 was synthesized; mp.: 102-103° C., $^1$H-NMR (DMSO-d$_6$): δ 7.71-7.33 (series of m, 11H), 6.45 (s, 1H), 6.44 (d, 1H), 5.29 (s, 1H), 3.97 (d, 1H), 3.71 (d, 1H). MS: 296.89 (M+H).

Example III-9

Synthesis of Compound III-9

Utilizing compound 31c and 3-chloromethyl-1,2,4-triazolin-5-one in step 1, compound III-9 was synthesized; mp.: >300° C.; $^1$H-NMR (DMSO-d$_6$): δ 11.48 (s, 2H), 7.65-7.34

(series of m, 10H), 5.42 (s, 1H) 3.75 (d, J=13.88 Hz, 1H), 3.46 (d, J=13.91 Hz, 1H). MS: 313.93 (M+H). 3-Chloromethyl-1,2,4-triazolin-5-one was described by Cowden, C. J.; Wilson R. D.; Bishop, B. C., Cottrell, I. F.; Davies, A. J.; Dolling, U-H. *Tetrahedron Letters*, 2000, 41, 8661. This reference has been incorporated herein in its entirety.

Example III-10

Synthesis of Compound III-10

Utilizing thien-2-yl-methanethiol and bromodiphenylmethane in step 1, compound III-10 was synthesized; m.p.: 122-124° C.; $^1$H-NMR (DMSO-d$_6$): δ 7.67-7.34 (series of m, 11H), 7.03 (m, 1H), 6.95 (m, 1H), 5.26 (ms, 1H), 4.17 (d, 1H), 3.79 (d, 1H). MS: 312.85 (M+H),

Example III-11

Synthesis of Compound III-11

Utilizing compound 31b and chloromethanesulfonamide in step 1, compound III-11 was synthesized; mp: 92-94° C., $^1$H-NMR (DMSO-d$_6$): δ 7.57-7.26 (two sets of m, 10H), 5.59 (s, 1H), 4.27 (d, 1H), 3.90 (d, 1H). MS: 367.86 (M+Na),

Example III-12

Synthesis of Compound III-12

Utilizing compound 31b and chloroacetone in step 1, compound III-12 was prepared; mp: 96-97° C.; -$^1$H-NMR (DMSO-d$_6$): δ 7.56-7.52 (m, 10H), 7.28-7.05 (m, 4H), 5.40 (s, 1H), 3.76 (d, 1H), 3.61 (d, 1H), 2.15 (s, 3H). MS: 330.95 (M+Na),

Example III-13

Synthesis of Compound III-13

Utilizing compound 31b and 2-chloroethoxytrimethylsilane in step 1, compound III-13 was prepared; mp: 91-92° C.; $^1$H-NMR (DMSO-d$_6$): δ 7.56-7.51 (m, 4H), 7.27-7.21 (m, 4H), 5.33 (s, 1H), 4.97 (t, 1H), 3.70 (m, 2H), 2.67-2.60 (m, 1H), 2.50-2.43 (m, 1H). MS: 318.96 (M+Na).

Example III-14

Synthesis of Compound III-14

Utilizing compound 31b and 2-bromoethylmethyl ether in step 1, compound III-14 was prepared; mp: 83-85° C., $^1$H-NMR (DMSO-d$_6$): δ 7.56-7.04 (2m, 8H), 5.34 (s, 1H), 3.61 (m, 2H), 3.22 (s, 3H), 2.76 (m, 1H), 2.51 (m, 1H). MS: 310.91 (M+H).

Example III-15

Synthesis of Compound III-15

Utilizing compound 31b and 1-bromo-2-(2-methoxyethoxy)ethane in step 1, compound III-15 was prepared; mp: 41-42° C.; $^1$H-NMR (DMSO-d$_6$): δ 7.56-7.22 (two m, 8H), 5.37 (s, 1H), 3.69 (m, 2H), 3.50 (m, 2H), 3.43 (m, 2H), 3.31 (s, 3H), 2.76 (m, 1H), 2.50 (m, 1H). MS: 376.93 (M+Na).

Scheme IV

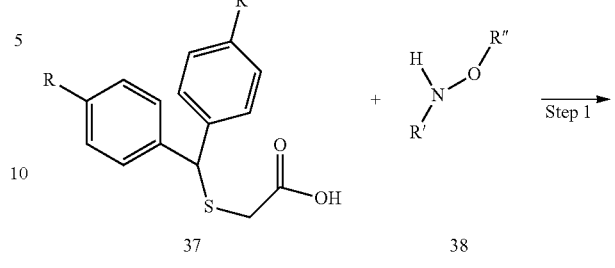

37 a: R = H
b: R = F

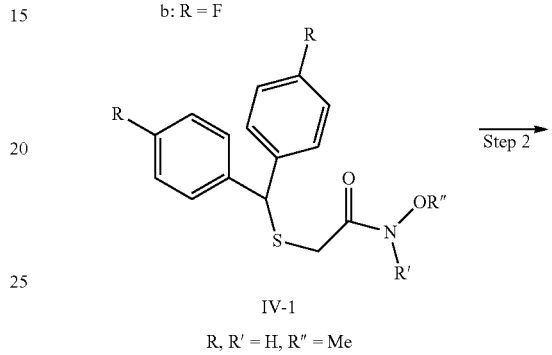

IV-1

R, R′ = H, R″ = Me

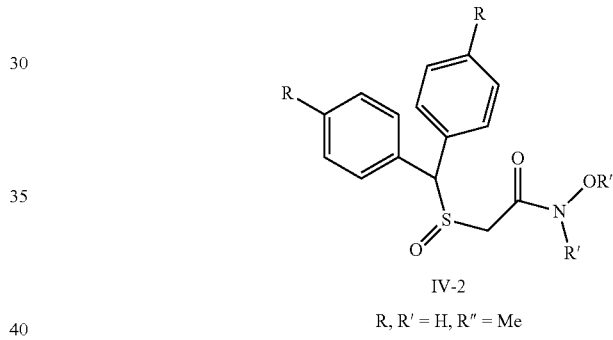

IV-2

R, R′ = H, R″ = Me

Reagents for Step 1: TBTU/DMF/room temperature or HOBT.NH$_3$/EDCI

Reagent for Step 2: 50% H$_2$O$_2$ in water/HOAc/room temperature.

Preparation of Compound 37a

The preparation of compound 37a was described in U.S. Pat. No. 4,006,686, which is incorporated herein in its entirety.

Example IV-1

Synthesis of Compound IV-1

A mixture of compound 37a (7.45 g, 27.79 mmol), O-methyl hydroxylamine hydrochloride (2.75 g, 32.93 mmol), TBTU (11.4 g, 35.5 mmol) and NMM (10 mL) in dry DMF (20 mL) was stirred at room temperature overnight. Excess solvent was removed and the mixture was diluted with EtOAc that was washed successively with water, 2% citric acid, water, 2% NaHCO$_3$, water and brine. Drying (MgSO$_4$) and solvent evaporation gave a crude product that was purified by flash chromatography (silica gel, hexane:EtOAc 2:3) to generate 7.71 g of compound IV-1; $^1$H-NMR (DMSO-d$_6$): δ 11.1 (s, 1H), 7.43-7.22 (series of m, 10H), 5.43 (s, 1H), 3.55 (s, 3H), 2.86 (s, 2H).

Example IV-2

Synthesis of Compound IV-2

Oxidation of the compound IV-1 (7.6 g, 26.48 mmol) with hydrogen peroxide (1 equiv.) in AcOH (25 mL), as described in Example III-2, generated compound IV-2 (5.98 g); mp: 140-141° C.; $^1$H-NMR (DMSO-$d_6$): δ 11.36 (s, 1H), 7.52-7.32 (series of m, 10H), 5.38 (s, 1H), 3.56 (s, 3H), 3.36 (d, 1H), 3.04 (d, 1H). MS: 303.88 (M+H).

Example IV-3

Synthesis of Compound IV-3

Utilizing compound 37a and O-Ethyl hydroxylamine hydrochloride in step 1, compound IV-3 was prepared; mp: 65° C.; $^1$H-NMR (DMSO-$d_6$): δ 11.22 (s, 1H), 7.50-7.34 (series of m, 10H), 5.38 (s, 1H), 3.76 (m, 2H), 3.31 (d, 1H), 3.06 (d, 1H), 1.11 (m, 3H). MS: 317.92 (M+H).

Example IV-4

Synthesis of Compound IV-4

Utilizing compound 37b and O-methyl hydroxylamine hydrochloride in step 1, compound IV-4 was prepared; mp: 103-104° C.; $^1$H-NMR (DMSO-$d_6$): δ 11.34 (s, 1H), 7.56-7.51 (m, 4H), 7.28-7.24 (m, 4H), 5.45 (s, 1H), 3.56 (s, 3H), 3.40 (d, J=13.53 Hz, 1H), 2.99 (d, J=13.55 Hz, 1H). MS: 361.89 (M+Na).

Reagents for Step 1: RMgBr or NaBH$_4$ (1.1-6 eqv.)/THF/0° C.—reflux.
Reagents for Step 2: 50% H$_2$O$_2$ in water/HOAc/RT
Preparation of Compound 42b
Compound 42b was prepared as described in U.S. Pat. No. 4,006,686, which is incorporated herein in its entirety.

Example V-1

Synthesis of Compound V-1

Utilizing compound 42b and 2-thiophenylmagnesium bromide (1M in THF, 3.2 eqv.), compound 44a was generated, which was then oxidized to give compound V-1; mp: 130-131° C.; $^1$H-NMR (DMSO-$d_6$): δ 8.09 (d, 1H), 8.08 (d, 1H), 7.84-7.24 (series of m, 11H), 5.51 (s, 1H), 4.17 (s, 2H). MS: 340.84 (M+H)

Example V-2

Synthesis of the Compound V-2

A solution of compound 42a (the intermediate from the preparation of compound III-3, 6.4 g, 25 mmol) in anhydrous THF (60 mL) was added dropwise to a solution of methyl magnesium bromide (1.4 M in THF: toluene, 22 mL, 30.8 mmol) at 0° C. The reaction mixture was stirred at 0° C. for an additional hour, quenched with saturated ammonium chloride solution, and extracted into EtOAc. The combined organic layers were washed successively with water and brine, dried (MgSO$_4$) and concentrated to generate compound 43a. It was then taken in HOAc (25 mL) and oxidized with hydrogen peroxide (50% in water, 1.7 mL), as described before, to generate 4.31 g of compound V-2; mp: 121-122° C.; $^1$H-NMR

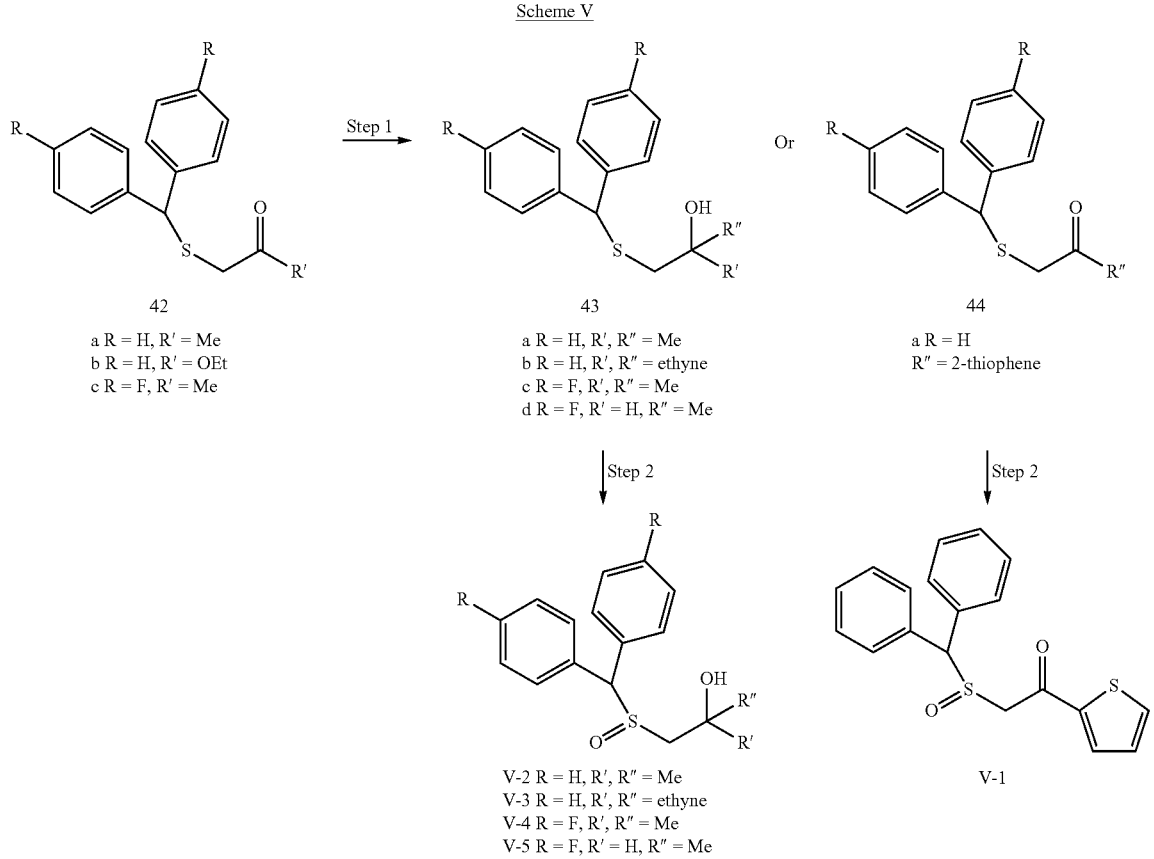

Scheme V

Reagents for Step 1: RMgBr or NaBH$_4$ (1.1-6 eqv.)/THF/0° C.-reflux.
Reagents for Step 2: 50% H$_2$O$_2$ in water/HOAc/RT (DMSO-d$_6$): δ 7.53-7.30 (series of m, 10H), 5.22 (s, 1H), 4.86 (s, 1H), 2.71 (d, 1H), 2.44 (d, 1H), 1.18 (s, 3H), 1.13 (s, 3H). MS: 288.96 (M+H).

Example V-3

Synthesis of Compound V-3

Utilizing compound 42b and acetylenemagnesium bromide (0.5M in THF, 6 eqv) in step 1, compound V-3 was generated; $^1$H-NMR (DMSO-d$_6$): δ 7.54-7.31 (series of m, 101H), 6.99 (s, 1H), 5.32 (s, 1H), 3.69 (two s, 2H), 3.15 (d, 1H), 2.74 (d, 1H). MS: 308.88 (M+H),

Example V-4

Synthesis of Compound V-4

Utilizing compound 42c (the intermediate from Example III-12) and methyl magnesium bromide (3M in ether, 1.1 eqv), compound V-4 (foam) was generated; $^1$H-NMR (DMSO-d$_6$): δ 7.56-7.21 (two m, 8H), 5.31 (s, 1H), 4.87 (s, 1H), 2.71 (d, 1H), 2.39 (d, 1H), 1.29 (s, 3H), 1.14 (s, 3H). MS: 324.95 (M+H).

Example V-5

Synthesis of the Compound V-5

To a solution of compound 42c (4.85 g, 16.60 mmol, the intermediate from Example III-12) in methanol (85 mL) was added sodium borohydride (660 mg, 17.44 mmol) in portions. The reaction mixture was then stirred at room temperature for 0.5 h, quenched with ice-water and extracted into EtOAc. The combined organic layers were washed with brine, dried (magnesium sulfate), and concentrated to generate compound 43d (oil, 4.62 g) that was oxidized to generate compound V-5 (mixture of diastereomers); mp: 96-98° C., $^1$H-NMR (DMSO-d$_6$): δ 7.56-7.21 (two m, 8H), 5.38 (s, 0.72H), 5.28 (s, 0.28H), 5.05 (m, 0.28H), 4.98 (m, 0.72H), 3.95 (m, 1H), 2.50 (m, 2H), 1.13 (d, 2.16H), 1.09 (d, 0.84H). MS: 310.92 (M+H).

Reagents for Step 1: NaH/DMF/ethyl bromodifluoroacetate (compound 32)/room temperature—70° C., 4 h.

Reagents for Step 2: Lithium aluminum hydride ("LAH") (1M in Et$_2$O)/THF/0° C., 1.5 h for compound 46; MeMgBr for compound 47.

Reagents for Step 3: m-Chloroperbenzoic acid ("m-CPBA"), dichloromethane, 0° C.

Preparation of Compound 31c

The preparation of compound 31c was described in U.S. Pat. No. 4,066,686, which has been incorporated herein in its entirety.

Synthesis of the Compound 46

Step 1: A solution of compound 31c (9.24 g, 46.2 mmol) in dry DMF (3 mL) was slowly added to a stirred mixture of NaH (60% in oil, 2.2 g, 55 mmol) in dry DMF (15 mL, room temperature, argon). The mixture was stirred at room temperature for 15 min, treated with compound 32 (11.41 g, 61 mmol) and heated at 70° C. for 4 h. The reaction mixture was then cooled to room temperature, concentrated at high vacuum, quenched with ice-water and extracted into EtOAc. The combined organic layers were washed successively with water and brine, dried (MgSO$_4$) and concentrated to generate compound 45 (12.34 g) that was directly used in the next step without any further purification.

Step 2: Thus, a solution of lithium aluminum hydride (1M in Et$_2$O) was slowly added to a solution of compound 45 (6.08 g, 18.88 mmol) in dry THF (50 mL, 0° C., argon). The mixture was stirred at 0° C. for 1.5 h, treated successively (carefully) with EtOAc (5 mL), water (5 mL), and 10% H$_2$SO$_4$ (20 mL). The mixture was then extracted into EtOAc. The combined organic layers were washed successively with water (twice) and brine, dried (MgSO$_4$), and concentrated to give a crude product that was purified by flash chromatography (silica gel, hexane:EtOAc 4:1) to generate compound 46 (syrup, 2.87 g); $^1$H-NMR (DMSO-d$_6$): δ 7.47-7.22 (3 m, 10H), 5.86 (t, 1H), 5.78 (s, 1H), 3.70 (m, 2H).

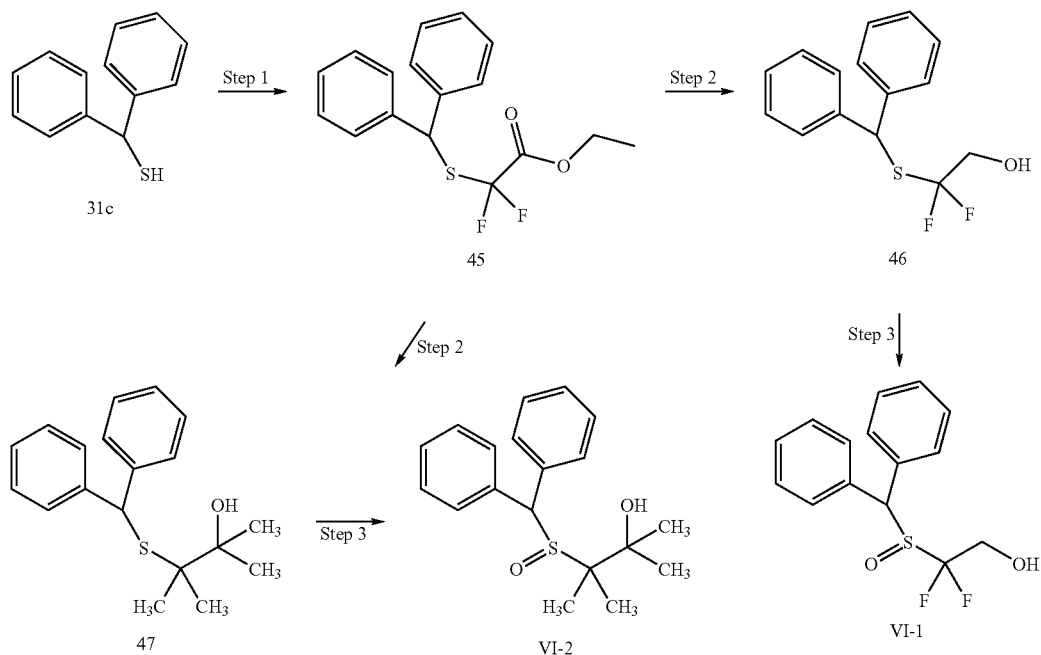

Scheme VI

Example VI-1

Synthesis of Compound VI-1

Following the procedure as described in Example II-19, compound 46 (2.68 g, 9.57 mmol) was oxidized with m-CPBA (77%, 2.36 g, 10.53 mmol) to generate compound VI-1 (2.08 g), mp: 77-79° C., $^1$H-NMR (DMSO-$d_6$): δ 7.58-7.32 (two m, 10H), 6.05 (m, 1H), 5.68 (s, 1H), 3.99-3.70 (two m, 2H). MS: 318.96 (M+H).

Example VI-2

Synthesis of Compound VI-2

Step 2: A solution of compound 45 (5.7 g, 17.7 mmol) in dry THF (40 mL) was added dropwise to a solution of methyl magnesium bromide (1.4 M in toluene, 65 mL, 91 mmol) under argon at room temperature. The reaction mixture was then stirred for 6 h, quenched with saturated ammonium chloride solution, and extracted into EtOAc. The combined organic layers were washed successively with water and brine, dried (MgSO$_4$) and concentrated to give a crude product that was purified by flash chromatography (silica gel, hexane:EtOAc 1:1) to provide compound 47 (766 mg) that was utilized in the next step; $^1$H-NMR (DMSO-$d_6$): δ 7.55-7.26 (series of m, 10H), 5.6 (s, 1H), 4.84 (s, 1H), 1.19 (two overlapping s, 6H), 1.09 (s, 3H).

Step 3: Thus, oxidation of compound 47 (0.76 g, 2.53 mmol) with m-CPBA (77%, 0.625 g, 2.78 mmol), following the procedure described in Example III-2, generated compound VI-2 (0.291 g); mp: 103-104° C.; $^1$H-NMR (DMSO-$d_6$): δ 7.55-7.24 (two m, 10H), 5.60 (s, 1H), 4.84 (s, 1H), 1.19 (s, 6H), 1.09 (s, 3H), 0.90 (s, 3H). MS: 316.95 (M+H).

Scheme VII

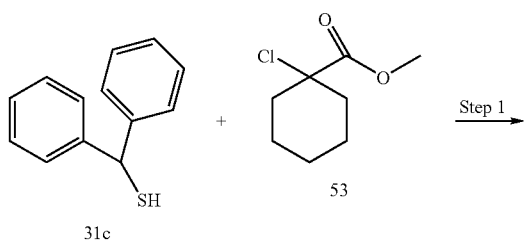

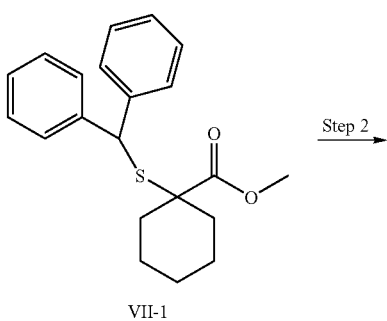

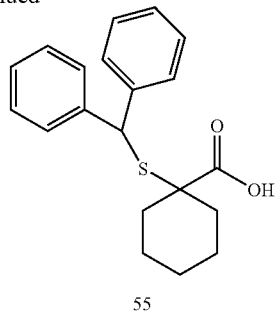

Reagents for Step 1: NaH/DMF/room temperature.
Reagents for Step 2: 1N NaOH/EtOH/reflux.
Reagents for Step 3: HOBT.NH$_3$/EDCI/DMF/room temperature.
Reagents for Step 4: 50% H$_2$O$_2$ in water/HOAc/room temperature.

Example VII-1

Synthesis of Compound VII-1

A solution of compound 31c (8.89 g, 44.45 mmol) in dry DMF (20 mL) was added dropwise to a stirred mixture of NaH (60% in oil, 2.2 g, 55 mmol) in dry DMF (40 mL, under argon, room temperature). The mixture was stirred for 15 min, treated with compound 53 (8 mL, 50.3 mmol) and stirred overnight. Excess solvent was removed and the residue was quenched with water followed by extraction into EtOAc. The combined organic layers were washed successively with water (twice) and brine, dried (MgSO$_4$) and concentrated to give a residue that was purified by flash chromatography (silica gel, hexane:EtOAc 3:2) to generate compound VII-1 (oil, 6.68 g); $^1$H-NMR (DMSO-$d_6$): δ 7.44-7.20 (m, 10H), 5.21 (m, 10H), 5.21 (s, 1H), 3.6 (s, 3H), 2.7 (m, 1H), 2.16 (m, 1H), 1.98-1.15 (series of m, 8H).

Example VII-2

Synthesis of Compound VII-2

A mixture of the compound VII-1 (6.68 g, 19.64 mmol), NaOH (1N, 100 mL) and EtOH (100 mL) was kept under reflux for 3 h. The mixture was cooled to room temperature, concentrated and washed with ether. The basic aqueous layer was neutralized with conc. HCl and extracted into EtOAc. The combined organic layers were washed successively with water (twice) and brine, dried (MgSO$_4$), and concentrated to yield compound 55 that was directly used in the next step without further purification.

Thus, a mixture of compound 55 (4.96 g, 15.21 mmol), HOBT.NH$_3$ complex (5 g, 32.89 mmol followed by an additional amount of 2.5 g, 16.44 mmol after 2 h), EDCI (3.5 g, 18.3 mmol followed by an additional amount of 1.75 g, 9.1 mmol after 3 h) in DMF (50 mL) was stirred at room temperature overnight, diluted with dichloromethane, washed successively with water, 2% citric acid, water, 2% NaHCO$_3$, water and brine, and dried (MgSO$_4$). Solvent evaporation generated a crude product that was purified by flash chromatography (silica gel, hexane:EtOAc::1:2) to yield compound VII-2 (2.42 g); $^1$H-NMR (DMSO-d$_6$): δ 7.44-7.06 (series of m, 10H), 6.98 (br s, 2H), 5.30 (s, 1H), 3.03 (m, 1H), 2.43 (m, 1H), 1.83-1.11 (series of m, 8H).

Example VII-3

Synthesis of Compound VII-3

To a solution of the compound VII-2 (2.2 g, 6.76 mmol) in AcOH (10 mL) was added hydrogen peroxide (50% solution in water, 470 μL). The reaction mixture was stirred at room temperature for 5 h, filtered and concentrated to give a crude product that was purified by flash chromatography (silica, EtOAc) to generate compound VII-3 (0.593 g) mp: 155-156° C., $^1$H-NMR (DMSO-d$_6$): δ 7.55-7.30 (series of m, 11H), 7.07 (s, 1H), 5.14 (s, 1H), 2.73 (m, 1H), 2.63 (m, 1H), 1.82-1.19 (series of m, 8H). MS: 342 (M+Na).

Example VIII-1

Synthesis of Compound VIII-1

A mixture of compound 57 (116 mg, 0.79 mmol and 304 mg, 2.08 mmol, respectively, in two batches) and compound 58 (1 eqv. in each case) was heated at 100° C. for 1 h and cooled to room temperature to give an adduct that was subjected to subsequent amidation as described in Scheme VII, Step 3, to generate compound VIII-1 (0.346 g from two batches); $^1$H-NMR (DMSO-d$_6$): δ 7.49-7.27 (series of m, 11H), 7.04 (s, 1H), 5.23 (s, 1H), 2.02-1.35 (3 m, 8H).

Example VIII-2

Synthesis of the Compound VIII-2

Following the procedure described in Example III-2, compound VIII-1 (342 mg, 1.09 mmol) was oxidized with hydrogen peroxide (75 μL) in AcOH (5 mL) to generate compound VIII-2 (0.282 g); mp: 129-130° C.; $^1$H-NMR (DMSO-d$_6$): 7.47-7.28 (m, 11H), 7.15 (s, 1H), 5.13 (s, 1H), 1.93-1.26 (3m, 8H). MS: 328 (M+H)

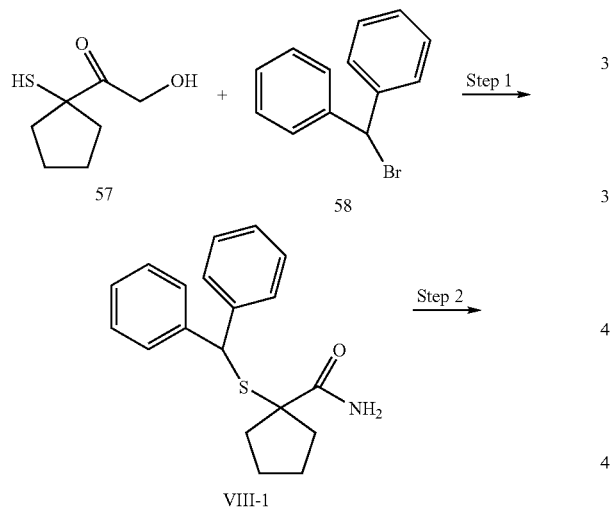

Scheme VIII

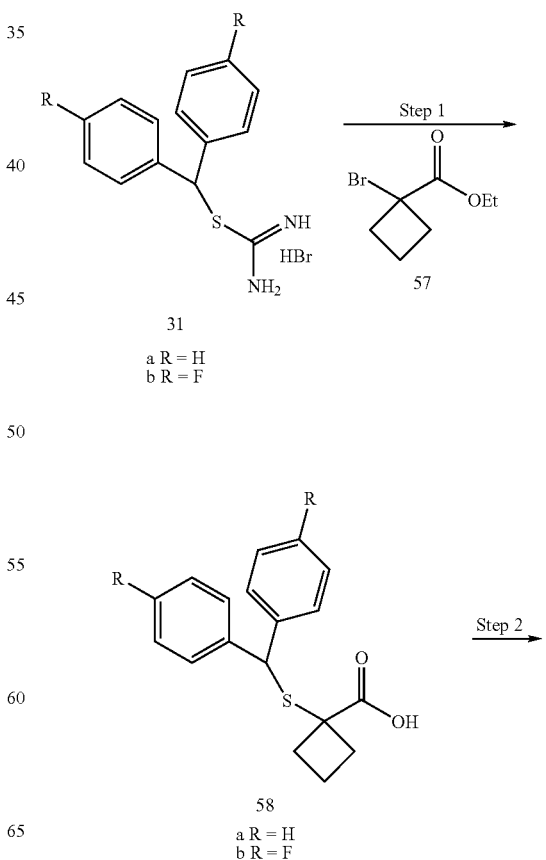

Scheme IX

Reagents for Step 1: a) 100° C.; b): HOBT.NH$_3$/TBTU/DMF/room temperature.
Reagents for Step 2: 50% H$_2$O$_2$ in water/HOAc/0° C. to room temperature.
Preparation of Compound 57
The preparation of compound 57 was described by Seebach, D.; Teschner, M. *Chem. Ber.* 1976, 109, 1601, which is incorporated herein in its entirety.

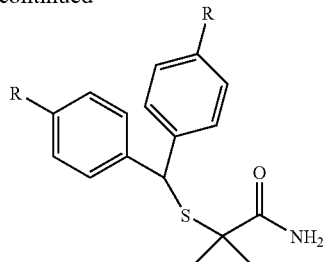

IX-1 R = H
59b R = F

Step 3 ↓

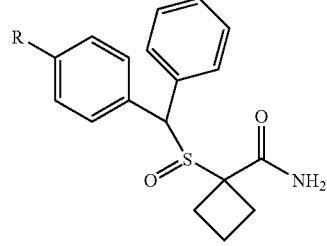

IX-2 R = H
IX-3 R = F

Reagents for Step 1: a) 10 N NaOH/EtOH/70° C.; b) compound 57, 70° C., overnight.
Reagents for Step 2: HOBT.NH$_3$/TBTU/NMM/DMF/room temperature.
Reagents for Step 3: 50% H$_2$O$_2$ in water/HOAc/room temperature.

Example IX-1

Synthesis of the Compound IX-1

A mixture of compound 31a (2 g, 6.19 mmol), 10 N NaOH (3 mL, 30 mmol) and water (3 mL) was stirred under argon at 70° C. for 15 min, treated with compound 57 (1 mL, 6.17 mmol) followed by heating at 70° C. overnight, and cooled to room temperature. It was then extracted into ether and the combined organic layers were washed successively with water and brine, dried (MgSO$_4$) and concentrated to generate compound 58a (1.46 g) that was directly taken to next step without further purifications. Thus, a mixture of compound 58a (1.45 g, 4.8 mmol), HOBT.NH$_3$ complex (1.63 g, 10.72 mmol), TBTU (1.87 g, 5.8 mmol), and NMM (2 mL) in dry DMF (10 mL) was stirred at room temperature overnight, diluted with EtOAc and washed successively with water, 2% citric acid, water, 2% NaHCO$_3$, water and brine. Drying (MgSO$_4$) and solvent evaporation generated a crude product that was purified by flash chromatography (silica gel, hexane: EtOAc 3:7) to yield compound IX-1 (0.395 g); $^1$H-NMR (DMSO-d$_6$): δ 7.42-7.20 (3 m, 10H), 6.97 (two overlapping broad s, 2H), 5.37 (s, 1H), 2.62 (s, 2H), 0.97 (m, 2H), 0.53 (m, 2H).

Example IX-2

Synthesis of Compound IX-2

Following the procedure described in Example III-2, compound IX-1 (384 mg, 1.29 mmol) was oxidized with hydrogen peroxide (90 μL) in AcOH (3 mL) to generate compound IX-2 (0.342 g); mp 158-159° C.; $^1$H-NMR (DMSO-d$_6$): δ 7.5-7.3 (m, 10H), 6.9 (two broad overlapping s, 2H), 5.23 (s, 1H), 3.13 (d, 1H), 2.31 (d, 1H), 1.23-0.62 (4 m, 4H). MS: 336 (M+Na).

Example IX-3

Synthesis of Compound IX-3

Utilizing compound 31b and compound 57 in step 1 and following the procedure as described above, compound IX-3 was generated; mp: 162° C.; $^1$H-NMR (DMSO-d$_6$): δ 7.54-7.50 (m, 4H), 7.26-7.21 (m, 4H), 6.97 (two broad overlapping broad s, 2H), 5.32 (s, 1H), 3.2 (d, 1H), 2.19 (d, 1H), 1.20-0.69 (4 m, 4H). MS: 350 (M+H)

Scheme X

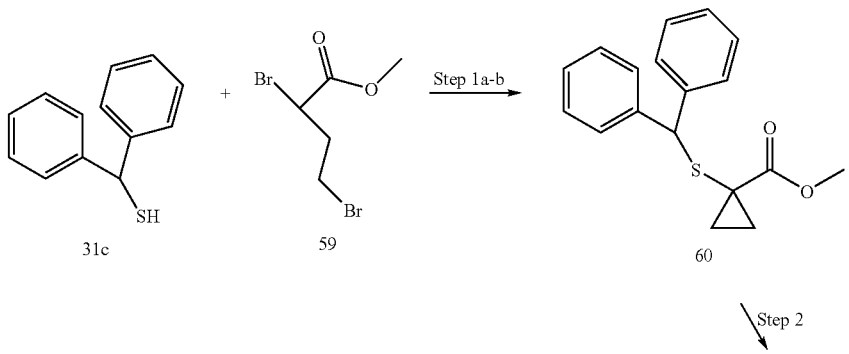

-continued

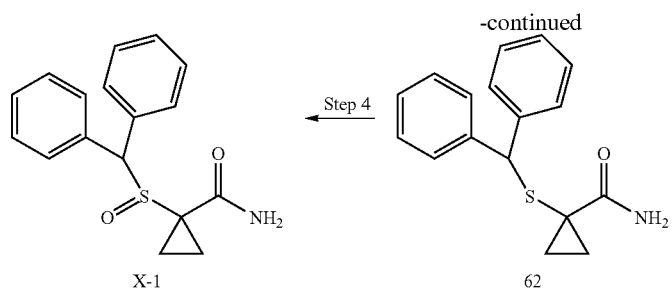

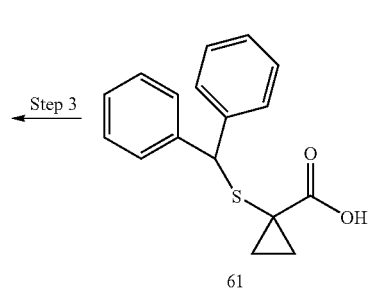

Reagents in Step 1: a) K$_2$CO$_3$/toluene/room temperature to 80° C. b) K$_2$CO$_3$/Bu$_4$NHSO$_4$/Toluene/80° C.
Reagents in Step 2: 1N NaOH/MeOH/reflux.
Reagents in Step 3: HOBT.NH$_3$/EDCI/DMF/RT.
Reagents in Step 4: 50% H$_2$O$_2$ in water/HOAc/room temperature.

Preparation of Compound 59

Preparation of compound 59 was described by Hoffmann, H. M. R.; Eggert, U.; Walenta, A.; Weineck, E.; Schomburg, D.; Wartchow, R.; Allen, F. H. *J. Org. Chem.* 1989, 54, 6096, which is incorporated herein by reference in its entirety.

Preparation of Compound 60

A mixture of the compound 31c (3.66 g, 18.3 mmol), compound 59 (6.3 g, 24.23 mmol), anhydrous K$_2$CO$_3$ (7.5 g, 54.34 mmol) in anhydrous toluene (50 mL) was stirred at room temperature for 96 h and then at 80° C. for 3 h. n-Bu$_4$NHSO$_4$ (450 mg) was added to the reaction mixture and stirring was continued at 80° C. for another 72 h. Additional quantities of K$_2$CO$_3$ (3 g), Bu$_4$NHSO$_4$ (150 mg), and toluene (20 mL) were then added to the reaction mixture and heating (at 80° C.) was continued for another 96 h. After cooling to room temperature, the reaction mixture was filtered and residue was washed with diethyl ether. The combined filtrate and washings were concentrated to give the crude product, 60, (5.17 g) which was directly used for the next step without further purifications.

Preparation of Compound 62

A mixture of compound 60 (5.15 g, 17.28 mmol), NaOH (1N, 100 mL), methanol (100 mL) was kept under reflux for 4 h, cooled to room temperature, and concentrated to remove excess methanol. Basic layer was acidified with conc. HCl and extracted into EtOAc. The combined organic layers were washed with brine, dried (MgSO$_4$), and concentrated to generate compound 61 (4.45 g) that was directly used in the next step.

Thus, a mixture of compound 61 (4.43 g, 15.65 mmol), HOBT.NH$_3$ complex (5.3 g, 34.86 mmol), EDCI (3.5 g, 18.3 mmol), DMAP (380 mg) in DMF (30 mL) was stirred at room temperature overnight, diluted with dichloromethane, successively washed successively with water, 2% citric acid, water, 2% NaHCO$_3$, water and brine, and dried (MgSO$_4$). Solvent evaporation gave a crude product that was purified by flash chromatography (silica gel, hexane:EtOAc 1:1) to generate the product (2.38 g); $^1$H-NMR (DMSO-d$_6$): δ 7.45-7.21 (3 m, 12H), 5.37 (s, 1H), 1.76 (m, 2H), 0.82 (m, 2H).

Example X-1

Synthesis of Compound X-1

Compound 62 (2.34 g, 8.26 mmol) was oxidized with hydrogen peroxide (570 μL) in AcOH (12 mL) to generate compound X-1 (1.81 g); mp: 148-149° C., $^1$H-NMR (DMSO-d$_6$): δ 7.5-7.31 (m, 11H), 7.25 (s, 1H), 5.51 (s, 1H), 1.0 (m, 2H), 0.63 (m, 2H). MS: 322 (M+Na).

Utility

The present invention provides a method of treating diseases and conditions in a subject in need thereof comprising administering to said subject a therapeutically effective amount of a compound of the present invention. For example, the compounds of the present invention may be useful for the treatment of diseases, such as excessive sleepiness, promotion and/or improvement of wakefulness (preferably improvement of wakefulness in patients with excessive sleepiness associated with narcolepsy, sleep apnea (preferably obstructive sleep apnea/hypopnea) and shift work disorder), treatment of Parkinson's disease, Alzheimer's disease, cerebral ischemia, stroke, eating disorders, attention deficit disorder ("ADD"), attention deficit hyperactivity disorder ("ADHD"), depression, schizophrenia, fatigue (preferably fatigue associated with cancer or neurological diseases, such as multiple sclerosis and chronic fatigue syndrome), stimulation of appetite and weight gain and improvement of cognitive dysfunction.

Methodology: Evaluation of Wake Promoting Activity in Rats

The methodology utilized for evaluating wake promoting activity of test compounds is based on that described by Edgar and Seidel, *Journal of Pharmacology and Experimental Therapeutics,* 283:757-769, 1997, and incorporated herein in its entirety by reference.

Animal Surgery. Adult, male Wistar rats (275-320 g from Charles River Laboratories, Wilmington, Mass.) were anesthetized (Nembutal, 45 mg/kg, ip.) and surgically prepared with implants for recording of chronic EEG (encephalographic) and EMG (electromyographic) recording. The EEG implants were made from commercially available components (Plastics One, Roanoke, Va.). EEG signals were recorded from stainless steel screw electrodes: 2 frontal (+3.0 mm AP from bregma, ±2.0 mm ML), and 2 occipital (−4.0 mm AP from bregma, ±2.0 mm ML). Two Teflon-coated stainless steel wires were positioned under the nuchal trapezoid muscles for EMG recording. All electrode leads were inserted into a connector pedestal and the pedestal affixed to the skull by application dental acrylic. Antibiotic was administered post surgically and antibiotic cream was applied to the wound edges to prevent infection. At least one week elapsed between surgery and recording.

Recording environment. Postsurgically, rats were housed in pairs in an isolated room. Food and water were available ad libitum, ambient temperature was 21° C., and humidity was 55%. At least 24 hrs prior to recording, they were placed in Nalgene containers (31×31×31 cm) with a wire-grid top, and entry to the room was prohibited during the day of recording except for dosing. The containers were placed on a rack with two shelves, 4 containers per shelf. Fluorescent overhead room lights were set to a 24 hr. light/dark cycle (on at 7 AM, off at 7 PM). Light levels inside the containers were 38 and 25 lux for the top and bottom shelves respectively. Background white-noise (68 db inside the containers) was present in the room to mask ambient sounds.

Data acquisition. EEG and EMG signals were led via cables to a commutator (Plastics One) and then to pre-amplifiers (model 1700, A-M Systems, Carlsborg, Wash.). EEG and EMG signals were amplified (10K and 1K respectively) and band pass filtered between 0.3 and 500 Hz for EEG and between 10 and 500 Hz for EMG. These signals were digitized at 128 samples per second using ICELUS sleep research software (M. Opp, U. Texas; see Opp, Physiology and Behavior 63:67-74, 1998, and Imeri, Mancia, and Opp, Neuroscience 92:745-749, 1999, incorporated by reference herein in their entirety) running under Labview 5.1 software and data acquisition hardware (PCI-MIO-16E-4; National Instruments, Austin, Tex.). On the day of dosing, data was recorded for 6 to 10 hours beginning at 11 AM.

Drug administration and study design. Compounds were evaluated on groups of from 4 to 8 rats carried out over one or two separate test sessions. Each animal was tested with a different compound or vehicle for up to 10 weeks with at least 7 days between successive tests. A vehicle group was included in all experiments, and each animal received vehicle every $4^{th}$ test. Test compounds were suspended in sterile 0.25% methylcellulose (pH=6.2; Upjohn Co., Kalamazoo, Mich.) at 30 mg/mL. Unless otherwise noted, compounds were administered at a single dose of 100 mg/kg. Dosing was carried out at noon, while the rats were predominantly asleep. Each rat was lifted out of its container, given an intraperitoneal injection in a volume of 5 mL/kg, and replaced. Dosing required approximately 30 sec per rat.

Sleep/wake scoring. Sleep and wake activity were determined using a procedure involving manual scoring using the ICELUS software, followed by application of an autoscoring program written in Microsoft Excel (Microsoft, Inc., Redmond, Wash.) The ICELUS program displays the EEG and EMG data in blocks of 6 sec along with the EEG frequency spectrum (FFT) amplitudes. Arousal state was scored as awake, rapid eye-movement (REM), or slow-wave or non-REM sleep according to visual analysis of EEG frequency and amplitude characteristics and EMG activity (Opp and Krueger, 1994; Van Gelder, et al., 1991; Edgar, et al., 1991, 1997; Seidel, et al, 1995, incorporated by reference herein in their entirety). Essentially, waking activity consists of relatively low-amplitude EEG activity with relatively lower power in the frequency band from 0.5-6 Hz, accompanied by moderate to high level EMG activity. In a particular waking state ("theta-waking"), EEG power can be relatively focused in the 6-9 Hz (theta) range, but significant EMG activity is always present. NREM sleep is characterized by relative high-amplitude EEG activity with relatively greater power in the low frequency band from 0.5-6 Hz, accompanied by little or no EMG activity. REM sleep is characterized by moderate and constant amplitude EEG focused in the theta (6-9 Hz) range, similar to waking theta, but with no EMG activity.

To convert the raw data to sleep/wake stage scores, normally the first hour of activity (prior to dosing) is manually scored into sleep, wake, or REM states. Subsequent activity is evaluated using a computer algorithm which takes into account FFT amplitudes, theta-band activity, and EMG activity for each 6 second epoch. An iterative procedure is used to adjust 3 different parameter thresholds until the first hour of data scored by the computer algorithm matches as closely as possible with the manual values. These parameter values are then used to score the remaining activity. The data are then reduced to "wake" (wake+waking theta activity) or "sleep" (REM+non-REM) for each 6 sec epoch. The time spent awake was then calculated for each 5 and 30 min interval relative to the specific time of dosing (approximately 12:00 noon).

Data Analysis and Statistics.

Two basic outcome measures were used to ascertain whether a compound exhibited wake-enhancing activity. The first was the percent time spent awake (0-100%) for each 30 min period following dosing. The second was the sum in minutes of the time spent awake for the first 6 half-hour periods following dosing (3 hr AUC; maximum 180 min).

For purposes of ascertaining activity of a test compound, wake activity values were compared against corresponding vehicle values. The vehicle values were of two types. The first type was the corresponding within-experiment vehicle, that is, a value derived from the vehicle group run concurrently with the test compound. A second reference vehicle value was also used for comparison, which consisted of the mean 3 hr AUC value calculated from 234 animals in 59 separate experiments carried out during the same time period as the evaluations of the test compounds (mean±SD=69.22±20.12; 95% confidence limits=66.63-71.81). Two-tailed, unpaired t-tests were performed on the wake time values for drug versus vehicle treated animals, and compounds with $p \leq 0.05$ were deemed significantly wake-promoting. A test compound was considered active as a wake promoting agent if it met one or more of the following three criteria.

(i) The 3 hr AUC value for the test compound was significantly greater ($p \leq 0.05$) than the mean wake value for the reference vehicle group (N=234).

(ii) The 3 hr AUC value for the test compound was significantly greater ($p \leq 0.05$) than the corresponding value for the within-experiment vehicle group.

(iii) One or more of the half-hour wake time values from 0.5 to 2 hrs after dosing were significantly greater ($p \leq 0.05$) in the test compound group compared to the within-experiment vehicle group.

Results.

Compounds of the invention either have demonstrated or are expected to demonstrate utility for wake promoting activity.

References. The following references, to the extent that they provide exemplary procedural or other details supplementary to those set forth herein, are specifically incorporated in their entirety herein by reference:

Touret, et al., *Neuroscience Letters*, 189:43-46, 1995.
Van Gelder, R. N. et al., *Sleep* 14:48-55, 1991.
Edgar, D. M., *J. Pharmacol. Exp. Ther.* 282:420-429, 1997.
Edgar and Seidel, *J. Pharmacol. Exp. Ther.*, 283:757-69, 1997.
Hernant et al., *Psychopharmacology*, 103:28-32, 1991.
Lin et al., *Brain Research*, 591:319-326, 1992.
Opp and Krueger, *American Journal of Physiology* 266: R688-95, 1994
Panckeri et al., *Sleep*, 19(8):626-631, 1996.
Seidel, W. F., et al., *J. Pharmacol. Exp. Ther.* 275:263-273, 1995.
Shelton et al., *Sleep* 18(10):817-826, 1995.
Welsh, D. K., et al., *Physiol. Behav.* 35:533-538, 1985.

Dosage and Formulation.

The compounds of the present invention can be administered for therapeutic purposes by any means that results in the contact of the active agent with the agent's site of action in a subject. The compounds may be administered by any conventional means available for use in conjunction with pharmaceuticals, either as individual therapeutic agents or in a combination with other therapeutic agents, such as, for example, analgesics, or in combination with antidepressants, including but are not limited to tricyclic antidepressants ("TCAs"), Selective Serotonin Reuptake Inhibitors ("SSRIs"), Serotonin and Noradrenalin Reuptake Inhibitors ("SNRIs"), Dopamine Reuptake Inhibitors ("DRIs"), Noradrenalin Reuptake Inhibitors ("NRUs"), Dopamine, Serotonin and Noradrenalin Reuptake Inhibitors ("DSNRIs") and Monoamine Oxidase Inhibitors ("MAOIs) including reversible inhibitors of monoamine oxidase type A (RIMAs). The compounds of the present invention are preferably administered in therapeutically effective amounts for the treatment of the diseases and disorders described herein.

A therapeutically effective amount can be readily determined by the attending diagnostician, as one skilled in the art, by the use of conventional techniques. The effective dose will vary depending upon a number of factors, including the pharmacodynamics of the active agent, the type and extent of progression of the disease or disorder, the age, weight and health of the particular patient, the formulation of the active and its mode and frequency of administration, and the desired effect with a minimization of side effects. Typically, the compounds are administered at lower dosage levels, with a gradual increase until the desired effect is achieved.

Typical dose ranges are from about 0.01 mg/kg to about 100 mg/kg of body weight per day, with a preferred dose from about 0.01 mg/kg to 10 mg/kg of body weight per day. A typical daily dose for adult humans can range from about 1 to about 1000 mg of the active agent, particularly from about 1 to about 400 mg, and including 25, 50, 85, 100, 150, 170, 200, 255, 250, 255, 340, 400, 425, 500, 600, 700, 750, 800, and 900 mg doses, and equivalent doses for a human child.

The compounds may be administered in one or more unit dose forms, and they may be administered in a single daily dose or in two, three or four doses per day. The unit dose ranges from about 1 to about 1000 mg, particularly from about 1 to about 400 mg, and including 25, 50, 85, 100, 150, 170, 200, 255, 250, 255, 340, 400, 425, 500, 600, 700, 750, 800, and 900 mg unit doses, and equivalent unit doses for a human child. In particular, the unit dosages range from about 1 to about 500 mg administered one to four times a day, preferably from about 10 mg to about 300 mg, two times a day. In an alternate method of describing an effective dose, an oral unit dose is one that is necessary to achieve a blood serum level of about 0.05 to 20 µg/ml in a subject, and preferably about 1 to 20 µg/ml.

The compounds of the present invention may be formulated into pharmaceutical compositions by admixture with one or more pharmaceutically acceptable excipients. The active agent may be present in about 0.5-95% by weight of the composition. The excipients are selected on the basis of the chosen route of administration and standard pharmaceutical practice, as described, for example, in *Remington: The Science and Practice of Pharmacy*, 20$^{th}$ ed.; Gennaro, A. R., Ed.; Lippincott Williams & Wilkins: Philadelphia, Pa., 2000.

The compositions can be prepared for administration by oral means, including tablets, pills, powders, capsules, troches and the like; parenteral means, including intravenous, intramuscular, and subcutaneous means; topical or transdermal means, including patches, creams, ointments, lotions, pastes, gels, solutions, suspensions, aerosols, and powders and the like; transmucosal means, including nasal, rectal, vaginal, sublingual and buccal means; ophthalmic or inhalation means. Preferably the compositions are prepared for oral administration, particularly in the form of tablets, capsules or syrups; parenteral administration, particularly in the form of liquid solutions, suspensions or emulsions; intranasal administration, particularly in the form of powders, nasal drops, or aerosols; or for topical use, such as patches, creams, ointments, and lotions.

For oral administration, the tablets, pills, powders, capsules, troches and the like can contain one or more of the following: diluents or fillers such as starch, or cellulose; binders such as microcrystalline cellulose, gelatins, or polyvinylpyrrolidone; disintegrants such as starch or cellulose derivatives; lubricants such as talc or magnesium stearate; glidants such as colloidal silicon dioxide; sweetening agents such as sucrose or saccharin; and flavoring agents such as peppermint or cherry flavoring. Capsules may contain any of the above ingredients, and may also contain a semi-solid or liquid carrier, such as a polyethylene glycol. The solid oral dosage forms may have coatings of sugar, shellac, or enteric agents. Liquid preparations may be in the form of aqueous or oily suspensions, solutions, emulsions, syrups, elixirs, etc., or may be provided as a dry product for reconstitution with water or other suitable vehicle before use. Such liquid preparations may contain conventional additives such as surfactants, suspending agents, emulsifying agents, diluents, sweetening and flavoring agents, dyes and preservatives.

The compositions may also be administered parenterally. The pharmaceutical forms acceptable for injectable use include, for example, sterile aqueous solutions, or suspensions. Aqueous carriers include mixtures of alcohols and water, buffered media, and the like. Nonaqueous solvents include alcohols and glycols, such as ethanol, and polyethylene glycols; oils, such as vegetable oils; fatty acids and fatty acid esters, and the like. Other components can be added including surfactants; such as hydroxypropylcellulose; isotonic agents, such as sodium chloride; fluid and nutrient replenishers; electrolyte replenishers; agents which control the release of the active compounds, such as aluminum monostearate, and various co-polymers; antibacterial agents, such as chlorobutanol, or phenol; buffers; suspending agents; thickening agents; and the like. The parenteral preparations can be enclosed in ampules, disposable syringes or multiple dose vials. Other potentially useful parenteral delivery systems for the active compounds include ethylene-vinyl acetate copolymer particles, osmotic pumps, implantable infusion systems, and liposomes.

Other possible modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for topical use are in the form of an ointment, cream, or gel. Typically these forms include a carrier, such as petrolatum, lanolin, stearyl alcohol, polyethylene glycols, or their combinations, and either an emulsifying agent, such as sodium lauryl sulfate, or a gelling agent, such as tragacanth. Formulations suitable for transdermal administration can be provided as discrete patches, as in a reservoir or microreservoir system, adhesive diffusion-controlled system or a matrix dispersion-type system. Formulations for buccal administration include, for example lozenges or pastilles and may also include a flavored base, such as sucrose or acacia, and other excipients such as glycocholate. Formulations suitable for rectal administration are preferably provided as unit-dose suppositories, with a solid based carrier, such as cocoa butter, and may include a salicylate.

The compositions of the present invention may be formulated to control and/or delay the release of the active agent(s). Such controlled-, delayed-, sustained-, or extended-release compositions are well-known in the art, and may include, for example, reservoir or matrix diffusion products, as well as dissolution systems. Some compositions may utilize, for example biocompatible, biodegradable lactide polymer, lactide/glycolide copolymer, or polyoxyethylene-polyoxypropylene copolymers as excipients.

As those skilled in the art will appreciate, numerous modifications and variations of the present invention are possible in light of the above teachings. It is therefore understood that within the scope of the appended claims, the invention may be practiced otherwise than as specifically described herein, and the scope of the invention is intended to encompass all such variations.

What is claimed is:

1. A compound of formula (I):

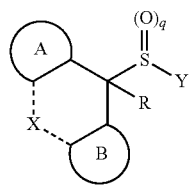

wherein
rings A and B, together with the carbon atoms to which they are attached, are each independently selected from a 6-membered aromatic carbocyclic ring, wherein said rings are optionally substituted with one to three $R^{20}$ groups;

X is not present, or is O, $S(O)_y$, $NR^{10}$, $C_2$ alkylene, $C_{2-3}$ alkenylene, C(=O), $C(R^{21})_2NR^{10}$, $C(R^{21})$=N, N=C $(R^{21})$, C(=O)N($R^{10}$), or $NR^{10}C$(=O); wherein said alkylene and alkenylene groups are optionally substituted with one to three $R^{20}$ groups;

R is H or $C_1$-$C_6$ alkyl;
Y is selected from:
a) $C_1$-$C_6$ alkylene-$R^1$;
b) $C_1$-$C_6$ alkylene-$R^2$;
c) $(C_1$-$C_4$ alkylene$)_m$-Z-$(C_1$-$C_4$ alkylene$)_n$-$R^1$;
d) $C_1$-$C_6$ alkylene-O(CH$_2$)$_p$OR$^{21}$,
e) $C_1$-$C_6$ alkyl substituted with one or two OR$^{21}$ groups; provided that Y cannot be $(CH_2)_{1-4}OR^{21}$; and
f) $CH_2CR^{21}$=C($R^{21}$)$_2$;
wherein said alkyl and alkylene groups are optionally substituted with one to three $R^{20}$ groups;

Z is O, $NR^{10A}$, $S(O)_y$, $CR^{21}$=$CR^{21}$, C=C($R^{21}$)$_2$, C≡C, $C_6$-$C_{10}$ arylene, 5-10 membered heteroarylene, $C_3$-$C_6$ cycloalkylene, or 3-6 membered heterocycloalkylene; wherein said arylene, heteroarylene, cycloalkylene, and heterocycloalkylene groups are optionally substituted with one to three $R^{20}$ groups;

$R^1$ is selected from $NR^{12}R^{13}$, $NR^{21}C$(=O)$R^{14}$, C(=O) $R^{15}$, OC(=O)$R^{11}$, $NR^{21}S(O)_2R^{11}$, $S(O)_2NR^{12}R^{13}$, $NR^{21}S(O)_2NR^{12}R^{13}$, and PO(OR$^{21}$)$_2$;

$R^2$ is a 5-6 membered heteroaryl;

$R^{10}$ and $R^{10A}$ at each occurrence are independently selected from H, $C_1$-$C_6$ alkyl, $C_6$-$C_{10}$ aryl, C(=O)$R^{15}$, and $S(O)_y$ $R^{14}$; wherein said alkyl and aryl groups are optionally substituted with one to three $R^{20}$ groups;

$R^{11}$ at each occurrence is independently selected from H and $C_1$-$C_6$ alkyl; wherein said alkyl is optionally substituted with one to three $R^{20}$ groups;

$R^{12}$ and $R^{13}$ at each occurrence are each independently selected from H, $C_1$-$C_6$ alkyl, and $C_6$-$C_{10}$ aryl, or $R^{12}$ and $R^{13}$, together with the nitrogen to which they are attached, form a 3-7 membered heterocycloalkyl ring selected from pyrrolidinyl, piperidinyl, and morpholinyl;

wherein said alkyl and aryl groups are optionally substituted with one to three $R^{20}$ groups;

$R^{14}$ at each occurrence is independently selected from $C_1$-$C_6$ alkyl, $C_6$-$C_{10}$ aryl, and arylalkyl; wherein said alkyl, aryl and arylalkyl groups are optionally substituted with one to three $R^{20}$ groups;

$R^{15}$ at each occurrence is independently selected from $C_1$-$C_6$ alkyl, $C_6$-$C_{10}$ aryl, arylalkyl, and thienyl; wherein said alkyl, aryl, arylalkyl, and thienyl groups are optionally substituted with one to three $R^{20}$ groups;

$R^{20}$ at each occurrence is independently selected from F, Cl, Br, I, OR$^{21}$, OR$^{25}$, NR$^{23}$R$^{24}$, NHOH, NO$_2$, CN, CF$_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, 5 or 6 membered heteroaryl, arylalkyl, =O, C(=O)R$^{22}$, CO$_2$R$^{21}$, OC(=O)R$^{22}$, C(=O) NR$^{23}$R$^{24}$, NR$^{21}$C(=O)R$^{22}$, NR$^{21}$CO$_2$R$^{22}$, OC(=O) NR$^{23}$R$^{24}$, NR$^{21}$C(=O)R$^{22}$, NR$^{21}$C(=S)R$^{22}$, and S(O)$_y$ R$^{22}$;

$R^{21}$ at each occurrence is independently selected from H and $C_1$-$C_6$ alkyl;

$R^{22}$ at each occurrence is independently selected from $C_1$-$C_6$ alkyl, and $C_6$-$C_{10}$ aryl;

$R^{23}$ and $R^{24}$ at each occurrence are each independently selected from H, $C_1$-$C_6$ alkyl, and $C_6$-$C_{10}$ aryl, or $R^{23}$ and $R^{24}$, together with the nitrogen to which they are attached, form a 3-7 membered heterocycloalkyl ring;

$R^{25}$ at each occurrence is independently the residue of an amino acid after the hydroxyl group of the carboxyl group is removed;

m is 0 or 1;
n is 0 or 1;
p is 1, 2, 3, or 4;
q is 1;
y is 0, 1, or 2;
with the following provisos:
1) Y cannot be

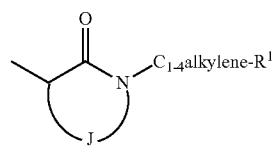

wherein J is $C_2$-$C_4$ alkylene or $C_1$-$C_3$ alkylene-CO—;
2) when X is not present, then $R^1$ cannot be $NR^{12}R^{13}$, and Y cannot be $C_1$-$C_6$ alkylene-$R^2$;
or a stereoisomeric form, mixture of stereoisomeric forms or a pharmaceutically acceptable salt thereof.

2. A compound as defined in claim 1, wherein X is not present.

3. A compound as defined in claim 1, wherein rings A and B are each phenylene.

4. A compound as defined in claim 1, wherein R is $C_1$-$C_4$ alkyl.

5. A compound as defined in claim 1, wherein Y is $C_1$-$C_6$ alkylene-$R^2$.

6. A compound as defined in claim 1, of the structure of formula (III):

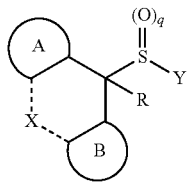

(III)

wherein
rings A and B, together with the carbon atoms to which they are attached, are each phenylene,
  wherein said rings are optionally substituted with one to three $R^{20}$ groups;
X is not present, or is O, $S(O)_y$, or $NR^{10}$;
R is H or $C_1$-$C_4$ alkyl;
Y is selected from:
  a) $C_1$-$C_6$ alkylene-$R^1$;
  b) $C_1$-$C_6$ alkylene-$R^2$;
  c) $(C_1$-$C_4$ alkylene$)_m$-$Z^1$—$(C_1$-$C_4$ alkylene$)_n$-$R^1$, or $C_1$-$C_4$ alkylene-$Z^2$—$C_1$-$C_4$ alkylene-$R^1$;
  d) $C_1$-$C_6$ alkylene-O(CH$_2$)$_p$OR$^{21}$,
  e) CH$_2$C(OH)(CH$_3$)$_2$, CH$_2$C(CH$_3$)$_2$OH, CH$_2$C(OH)$_2$CF$_3$, CH$_2$C(OH)(C≡CH)$_2$, or CH$_2$CH(OH)CH$_3$, and
  f) CH$_2$CR$^{21}$=C(R$^{21}$)$_2$;
    wherein said alkyl and alkylene groups are optionally substituted with one to three $R^{20}$ groups;
$Z^1$ is $CR^{21}$=$CR^{21}$, C=C(R$^{21}$)$_2$, C≡C, or phenylene;
  wherein said phenylene group is optionally substituted with one to three $R^{20}$ groups;
$Z^2$ is O, $NR^{10A}$, or $S(O)_y$;
$R^1$ is selected from $NR^{12}R^{13}$, $NR^{21}C(=O)R^{14}$, $C(=O)R^{15}$, $NR^{21}S(O)_2R^{11}$, $S(O)_2NR^{12}R^{13}$, and $PO(OR^{21})_2$;
$R^2$ is pyridyl, furyl, thienyl, or a 5-membered heteroaryl group containing 1-3 nitrogen atoms;
$R^{10}$ and $R^{10A}$ at each occurrence are independently selected from H, $C_1$-$C_6$ alkyl, $C_6$-$C_{10}$ aryl, $C(=O)R^{15}$, and $S(O)_yR^{14}$; wherein said alkyl and aryl groups are optionally substituted with one to three $R^{20}$ groups;
$R^{11}$ at each occurrence is independently selected from H, and $C_1$-$C_6$ alkyl; wherein said alkyl is optionally substituted with one to three $R^{20}$ groups;
$R^{12}$ and $R^{13}$ at each occurrence are each independently selected from H and $C_1$-$C_6$ alkyl, or $R^{12}$ and $R^{13}$, together with the nitrogen to which they are attached, form a 5-6 membered heterocycloalkyl selected from pyrrolidinyl, piperidinyl, and morpholinyl;
  wherein said alkyl and heterocycloalkyl groups are optionally substituted with one to three $R^{20}$ groups;
$R^{14}$ at each occurrence is independently selected from $C_1$-$C_6$ alkyl, $C_6$-$C_{10}$ aryl, and arylalkyl;
wherein said alkyl, aryl and arylalkyl groups are optionally substituted with one to three $R^{20}$ groups;
$R^{15}$ at each occurrence is independently selected from $C_1$-$C_6$ alkyl, $C_6$-$C_{10}$ aryl, arylalkyl, and thienyl; wherein said alkyl, aryl, arylalkyl, and thienyl groups are optionally substituted with one to three $R^{20}$ groups;
$R^{20}$ at each occurrence is independently selected from F, Cl, Br, I, $OR^{21}$, $OR^{25}$, $NR^{23}R^{24}$, NHOH, $NO_2$, CN, $CF_3$, $C_1$-$C_6$ alkyl, $C_3$-$C_6$ spirocycloalkyl, $C_2$-$C_6$ alkenyl, $C_2$-$C_6$ alkynyl, $C_3$-$C_7$ cycloalkyl, 3-7 membered heterocycloalkyl, phenyl, 5 or 6 membered heteroaryl, arylalkyl, =O, $C(=O)R^{22}$, $CO_2R^{21}$, $OC(=O)R^{22}$, $C(=O)NR^{23}R^{24}$, $NR^{21}C(=O)R^{22}$, $NR^{21}CO_2R^{22}$, $OC(=O)NR^{23}R^{24}$, $NR^{21}C(=O)R^{22}$, $NR^{21}C(=S)R^{22}$, and $S(O)_yR^{22}$;
$R^{21}$ at each occurrence is independently selected from H and $C_1$-$C_6$ alkyl;
$R^{22}$ at each occurrence is independently selected from $C_1$-$C_6$ alkyl, and phenyl;
$R^{23}$ and $R^{24}$ at each occurrence are each independently selected from H and $C_1$-$C_6$ alkyl, or $R^{23}$ and $R^{24}$, together with the nitrogen to which they are attached, form a 5-6 membered heterocycloalkyl;
$R^{25}$ at each occurrence is independently the residue of an amino acid after the hydroxyl group of the carboxyl group is removed;
m is 0 or 1;
n is 0 or 1;
p is 1, 2, 3, or 4;
q is 1;
y is 0, 1, or 2;
with the following provisos:
  when X is not present, then $R^1$ cannot be $NR^{12}R^{13}$ and Y cannot be $C_1$-$C_6$ alkylene-$R^2$;
or a stereoisomeric form, mixture of stereoisomeric forms or a pharmaceutically acceptable salt thereof.

7. A compound as defined in claim 6, wherein rings A and B are each phenylene.

8. A compound as defined in claim 7, wherein X is not present.

9. A compound as defined in claim 7, wherein R is $C_1$-$C_4$ alkyl and Y is $C_1$-$C_6$ alkylene-$R^1$.

10. A compound as defined in claim 1, of the structure of formula (IV):

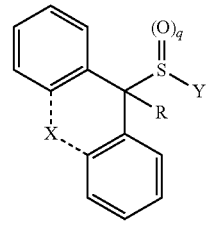

(IV)

wherein
the phenylene rings are each independently optionally substituted with one to three $R^{20}$ groups;
X is not present;
R is H or $C_1$-$C_4$ alkyl;
Y is selected from:
  a) $C_1$-$C_6$ alkylene-$R^1$;
  b) $C_1$-$C_4$ alkylene-O(CH$_2$)$_p$OR$^{21}$,
  c) CH$_2$C(OH)(CH$_3$)$_2$, CH$_2$C(CH$_3$)$_2$OH, CH$_2$C(OH)$_2$CF$_3$, CH$_2$C(OH)(C≡CH)$_2$, or CH$_2$CH(OH)CH$_3$, and
  d) CH$_2$CR$^{21}$=C(R$^{21}$)$_2$;
    wherein said alkylene groups are optionally substituted with an $R^{20}$ group;
$R^1$ is selected from $NR^{21}C(=O)R^{14}$, $C(=O)R^{15}$, $NR^{21}S(O)_2R^{11}$, $S(O)_2NR^{12A}R^{13A}$, and $PO(OR^{21})_2$;
$R^{11}$ at each occurrence is independently $C_1$-$C_6$ alkyl;
$R^{12A}$ and $R^{13A}$ at each occurrence are each independently selected from H and $C_1$-$C_6$ alkyl;
$R^{14}$ at each occurrence is independently $C_1$-$C_6$ alkyl;

R<sup>15</sup> at each occurrence is independently selected from C<sub>1</sub>-C<sub>6</sub> alkyl, and thienyl;

R<sup>20</sup> at each occurrence is independently selected from F, Cl, Br, I, OR<sup>21</sup>, OR<sup>25</sup>, NR<sup>23</sup>R<sup>24</sup>, NHOH, NO<sub>2</sub>, CN, CF<sub>3</sub>, C<sub>1</sub>-C<sub>6</sub> alkyl, C<sub>3</sub>-C<sub>6</sub> spirocycloalkyl, C<sub>2</sub>-C<sub>6</sub> alkenyl, C<sub>2</sub>-C<sub>6</sub> alkynyl, C<sub>3</sub>-C<sub>7</sub> cycloalkyl, 3-7 membered heterocycloalkyl, phenyl, 5 or 6 membered heteroaryl, arylalkyl, =O, C(=O)R<sup>22</sup>, CO<sub>2</sub>R<sup>21</sup>, OC(=O)R<sup>22</sup>, C(=O)NR<sup>23</sup>R<sup>24</sup>, NR<sup>21</sup>C(=O)R<sup>22</sup>, NR<sup>21</sup>CO<sub>2</sub>R<sup>22</sup>, OC(=O)NR<sup>23</sup>R<sup>24</sup>, NR<sup>21</sup>C(=O)R<sup>22</sup>, NR<sup>21</sup>C(=S)R<sup>22</sup>, and S(O)<sub>y</sub>R<sup>22</sup>;

R<sup>21</sup> at each occurrence is independently selected from H and C<sub>1</sub>-C<sub>6</sub> alkyl;

R<sup>22</sup> at each occurrence is independently selected from C<sub>1</sub>-C<sub>6</sub> alkyl, and phenyl;

R<sup>23</sup> and R<sup>24</sup> at each occurrence are each independently selected from H and C<sub>1</sub>-C<sub>6</sub> alkyl, or R<sup>23</sup> and R<sup>24</sup>, together with the nitrogen to which they are attached, form a 5-6 membered heterocycloalkyl;

R<sup>25</sup> at each occurrence is independently the residue of an amino acid after the hydroxyl group of the carboxyl group is removed;

p is 1, 2, 3, or 4;

q is 1;

y is 0, 1, or 2;

or a stereoisomeric form, mixture of stereoisomeric forms or a pharmaceutically acceptable salt thereof.

11. A compound as defined in claim 1, of the structure of formula (V):

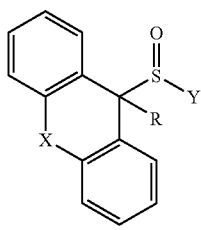

(V)

wherein the phenylene rings are each independently optionally substituted with one to three R<sup>20</sup> groups;

X is O, S(O)<sub>y</sub>, NR<sup>10</sup>, C<sub>2</sub> alkylene, or C<sub>2</sub> alkenylene, wherein said alkylene and alkenylene groups are optionally substituted with an R<sup>20</sup> group;

R is H or C<sub>1</sub>-C<sub>4</sub> alkyl;

Y is selected from:
 a) C<sub>1</sub>-C<sub>6</sub> alkylene-R<sup>1</sup>; and
 b) CH<sub>2</sub>CR<sup>21</sup>=C(R<sup>21</sup>)<sub>2</sub>;

R<sup>1</sup> is selected from pyrrolidinyl, piperidinyl, morpholinyl, NR<sup>21</sup>C(=O)R<sup>14</sup>, and NR<sup>21</sup>S(O)<sub>2</sub>R<sup>11</sup>;

R<sup>10</sup> is independently selected from H, C<sub>1</sub>-C<sub>6</sub> alkyl, C<sub>6</sub>-C<sub>10</sub> aryl, C(=O)R<sup>14</sup>, and S(O)<sub>y</sub>R<sup>14</sup>; wherein said alkyl and aryl groups are optionally substituted with one to three R<sup>20</sup> groups;

R<sup>11</sup> at each occurrence is independently C<sub>1</sub>-C<sub>6</sub> alkyl;

R<sup>14</sup> at each occurrence is independently C<sub>1</sub>-C<sub>6</sub> alkyl;

R<sup>20</sup> at each occurrence is independently selected from F, Cl, Br, I, OR<sup>21</sup>, OR<sup>25</sup>, NR<sup>23</sup>R<sup>24</sup>, NHOH, NO<sub>2</sub>, CN, CF<sub>3</sub>, C<sub>1</sub>-C<sub>6</sub> alkyl, C<sub>3</sub>-C<sub>6</sub> spirocycloalkyl, C<sub>2</sub>-C<sub>6</sub> alkenyl, C<sub>2</sub>-C<sub>6</sub> alkynyl, C<sub>3</sub>-C<sub>7</sub> cycloalkyl, 3-7 membered heterocycloalkyl, phenyl, 5 or 6 membered heteroaryl, arylalkyl, =O, C(=O)R<sup>22</sup>, CO<sub>2</sub>R<sup>21</sup>, OC(=O)R<sup>22</sup>, C(=O)NR<sup>23</sup>R<sup>24</sup>, NR<sup>21</sup>C(=O)R<sup>22</sup>, NR<sup>21</sup>CO<sub>2</sub>R<sup>22</sup>, OC(=O)NR<sup>23</sup>R<sup>24</sup>, NR<sup>21</sup>C(=O)R<sup>22</sup>, NR<sup>21</sup>C(=S)R<sup>22</sup>, and S(O)<sub>y</sub>R<sup>22</sup>;

R<sup>21</sup> at each occurrence is independently selected from H and C<sub>1</sub>-C<sub>6</sub> alkyl;

R<sup>22</sup> at each occurrence is independently selected from C<sub>1</sub>-C<sub>6</sub> alkyl, and phenyl;

R<sup>23</sup> and R<sup>24</sup> at each occurrence are each independently selected from H and C<sub>1</sub>-C<sub>6</sub> alkyl, or R<sup>23</sup> and R<sup>24</sup>, together with the nitrogen to which they are attached, form a 5-6 membered heterocycloalkyl;

R<sup>25</sup> at each occurrence is independently the residue of an amino acid after the hydroxyl group of the carboxyl group is removed;

y is 0, 1, or 2;

or a stereoisomeric form, mixture of stereoisomeric forms or a pharmaceutically acceptable salt thereof.

12. A compound of claim 1, of the structure of formula (VI):

(VI)

wherein

Ar<sup>1</sup> and Ar<sup>2</sup> are each independently phenyl optionally substituted with one to three R<sup>20</sup> groups;

R is H or C<sub>1</sub>-C<sub>4</sub> alkyl;

Y is selected from:
 a) C<sub>1</sub>-C<sub>6</sub> alkylene-R<sup>1</sup>;
 b) C<sub>1</sub>-C<sub>6</sub> alkylene-O(CH<sub>2</sub>)<sub>p</sub>OR<sup>21</sup>, and
 c) CH<sub>2</sub>C(OH)(CH<sub>3</sub>)<sub>2</sub>, CH<sub>2</sub>C(CH<sub>3</sub>)<sub>2</sub>OH, CH<sub>2</sub>C(OH)<sub>2</sub>CF<sub>3</sub>, CH<sub>2</sub>C(OH)(C≡CH)<sub>2</sub>, or CH<sub>2</sub>CH(OH)CH<sub>3</sub>;

R<sup>1</sup> is selected from C(=O)R<sup>15</sup>, S(O)<sub>2</sub>NR<sup>12A</sup>R<sup>13A</sup>, and PO(OR<sup>21</sup>)<sub>2</sub>;

R<sup>11</sup> at each occurrence is independently C<sub>1</sub>-C<sub>6</sub> alkyl;

R<sup>12A</sup> and R<sup>13A</sup> at each occurrence are each independently selected from H and C<sub>1</sub>-C<sub>6</sub> alkyl;

R<sup>15</sup> at each occurrence is independently selected from C<sub>1</sub>-C<sub>6</sub> alkyl, and thienyl;

R<sup>20</sup> at each occurrence is independently selected from F, Cl, Br, I, OR<sup>21</sup>, OR<sup>25</sup>, NR<sup>23</sup>R<sup>24</sup>, NHOH, NO<sub>2</sub>, CN, CF<sub>3</sub>, C<sub>1</sub>-C<sub>6</sub> alkyl, C<sub>3</sub>-C<sub>6</sub> spirocycloalkyl, C<sub>2</sub>-C<sub>6</sub> alkenyl, C<sub>2</sub>-C<sub>6</sub> alkynyl, C<sub>3</sub>-C<sub>7</sub> cycloalkyl, 3-7 membered heterocycloalkyl, phenyl, 5 or 6 membered heteroaryl, arylalkyl, =O, C(=O)R<sup>22</sup>, CO<sub>2</sub>R<sup>21</sup>, OC(=O)R<sup>22</sup>, C(=O)NR<sup>23</sup>R<sup>24</sup>, NR<sup>21</sup>C(=O)R<sup>22</sup>, NR<sup>21</sup>CO<sub>2</sub>R<sup>22</sup>, OC(=O)NR<sup>23</sup>R<sup>24</sup>, NR<sup>21</sup>C(=O)R<sup>22</sup>, NR<sup>21</sup>C(=S)R<sup>22</sup>, and S(O)<sub>y</sub>R<sup>22</sup>;

R<sup>21</sup> at each occurrence is independently selected from H and C<sub>1</sub>-C<sub>6</sub> alkyl;

R<sup>22</sup> at each occurrence is independently selected from C<sub>1</sub>-C<sub>6</sub> alkyl, and phenyl;

R<sup>23</sup> and R<sup>24</sup> at each occurrence are each independently selected from H and C<sub>1</sub>-C<sub>6</sub> alkyl, or R<sup>23</sup> and R<sup>24</sup>, together with the nitrogen to which they are attached, form a 5-6 membered heterocycloalkyl;

R<sup>25</sup> at each occurrence is independently the residue of an amino acid after the hydroxyl group of the carboxyl group is removed;

p is 1, 2, 3, or 4;

y is 0, 1, or 2;

or a stereoisomeric form, mixture of stereoisomeric forms or a pharmaceutically acceptable salt thereof.

13. A compound as defined in claim 12, wherein $Ar^1$ and $Ar^2$ are each independently phenyl optionally substituted with one to three $R^{20}$ groups;

R is H or $C_1$-$C_4$ alkyl;

Y is selected from:
 a) $C_1$-$C_4$ alkylene-$R^1$;
 b) $CH_2CH_2O(CH_2)_2OCH_3$, and
 c) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, $R^1$ is selected from $C(=O)R^{15}$, $S(O)_2NR^{12A}R^{13A}$, and $PO(OR^{21})_2$;

$R^{11}$ at each occurrence is independently $C_1$-$C_4$ alkyl;

$R^{12A}$ and $R^{13A}$ at each occurrence are each independently selected from H and $C_1$-$C_4$ alkyl;

$R^{15}$ at each occurrence is independently selected from $C_1$-$C_4$ alkyl, and thienyl;

$R^{20}$ at each occurrence is independently selected from F, Cl, Br, I, $OR^{21}$, $OR^{25}$, $NR^{23}R^{24}$, NHOH, $NO_2$, CN, $CF_3$, $C_3$-$C_6$ spirocycloalkyl, $=O$, $C(=O)R^{22}$, $CO_2R^{21}$, $C(=O)NR^{23}R^{24}$, and $NR^{21}C(=O)R^{22}$;

$R^{21}$ at each occurrence is independently selected from H and $C_1$-$C_4$ alkyl;

$R^{22}$ at each occurrence is independently $C_1$-$C_4$ alkyl;

$R^{23}$ and $R^{24}$ at each occurrence are each independently selected from H and $C_1$-$C_4$ alkyl, or $R^{23}$ and $R^{24}$, together with the nitrogen to which they are attached, form a 5-6 membered heterocycloalkyl;

$R^{25}$ at each occurrence is independently the residue of an amino acid after the hydroxyl group of the carboxyl group is removed;

or a stereoisomeric form, mixture of stereoisomeric forms or a pharmaceutically acceptable form thereof.

14. A compound selected in accordance with the following Table 2:

TABLE 2

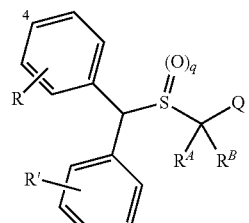

| Compound No. | R | R' | q | $R^A$ | $R^B$ | Q |
|---|---|---|---|---|---|---|
| III-1 | H | H | 0 | H | H | $SO_2NH_2$ |
| III-2 | H | H | 1 | H | H | $SO_2NH_2$ |
| III-3 | H | H | 1 | H | H | $COCH_3$ |
| III-4 | H | H | 1 | H | H | $P(O)(O^iPr)_2$ |
| III-5 | H | H | 1 | H | H | $C(OH)_2CF_3$ |
| III-8 | H | H | 1 | H | H | 2-Furyl |
| III-9 | H | H | 1 | H | H | ![triazolone] |
| III-10 | H | H | 1 | H | H | 2-thiophene |
| III-11 | 4-F | 4'-F | 1 | H | H | $SO_2NH_2$ |
| III-12 | 4-F | 4'-F | 1 | H | H | $COCH_3$ |
| III-13 | 4-F | 4'-F | 1 | H | H | $CH_2OH$ |
| III-14 | 4-F | 4'-F | 1 | H | H | $CH_2OMe$ |

TABLE 2-continued

| Compound No. | R | R' | q | $R^A$ | $R^B$ | Q |
|---|---|---|---|---|---|---|
| III-15 | 4-F | 4'-F | 1 | H | H | $CH_2O(CH_2)_2OMe$ |
| V-1 | H | H | 1 | H | H | CO-2-thienyl |
| V-2 | H | H | 1 | H | H | $C(OH)Me_2$ |
| V-3 | H | H | 1 | H | H | $C(OH)(C\equiv CH)_2$ |
| V-4 | 4-F | 4'-F | 1 | H | H | $C(OH)Me_2$ |
| V-5 | 4-F | 4'-F | 1 | H | H | $CH(OH)Me$ |
| VI-1 | H | H | 1 | F | F | $CH_2OH$ |
| VI-2 | H | H | 1 | Me | Me | $CMe_2OH$ |
| VII-1 | H | H | 0 | Cyclohexyl | | $CO_2CH_3$ | or a stereoisomeric form, mixture of stereoisomeric forms or a pharmaceutically acceptable salt thereof.

15. A pharmaceutical composition comprising a compound of claim 1 in admixture with one or more pharmaceutically acceptable excipients.

16. A compound as defined in claim 1, wherein Y is selected from:
 a) $C_1$-$C_6$ alkylene-$R^1$;
 b) $C_1$-$C_6$ alkylene-$R^2$;
 c) $(C_1$-$C_4$alkylene$)_m$-Z-$(C_1$-$C_4$alkylene$)_n$-$R^1$;
 d) $C_1$-$C_6$alkylene-$O(CH_2)_pOR^{21}$;
 e) $C_1$-$C_6$ alkyl substituted with one or two $OR^{21}$ groups; provided that Y cannot be $(CH_2)_{1-4}OR^{21}$; and
 f) $CH_2CR^{21}=C(R^{21})_2$;

wherein said alkyl and alkylene groups are unsubstituted.

17. A compound as defined in claim 16, wherein R is $C_1$-$C_6$ alkyl.

18. A compound as defined in claim 6, wherein Y is selected from:
 a) $C_1$-$C_6$ alkylene-$R^1$;
 b) $C_1$-$C_6$ alkylene-$R^2$;
 c) $(C_1$-$C_4$ alkylene$)_m$-$Z^1$-$(C_1$-$C_4$alkylene$)_n$-$R^1$, or $C_1$-$C_4$ alkylene-$Z^2$-$C_1$-$C_4$ alkylene-$R^1$,
 d) $C_1$-$C_6$alkylene-$O(CH_2)_pOR^{21}$;
 e) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, and
 f) $CH_2CR^{21}=C(R^{21})_2$, or $CH_2CR^{21}=C(R^{21})_2$;

wherein said alkyl and alkylene groups are unsubstituted.

19. A compound as defined in claim 18, wherein R is $C_1$-$C_6$ alkyl.

20. A compound as defined in claim 10, wherein Y is selected from:
 a) $C_1$-$C_6$ alkylene-$R^1$;
 b) $C_1$-$C_6$alkylene-$O(CH_2)_pOR^{21}$,
 c) $CH_2C(OH)(CH_3)_2$, $CH_2C(CH_3)_2OH$, $CH_2C(OH)_2CF_3$, $CH_2C(OH)(C\equiv CH)_2$, or $CH_2CH(OH)CH_3$, and
 d) $CH_2CR^{21}=C(R^{21})_2$ or;

wherein said alkyl and alkylene groups are unsubstituted.

21. A compound as defined in claim 20, wherein R is $C_1$-$C_6$ alkyl.

22. A compound as defined in claim 11, wherein R is $C_1$-$C_6$ alkyl.

* * * * *